(12) United States Patent
Follmann et al.

(10) Patent No.: US 8,378,092 B2
(45) Date of Patent: Feb. 19, 2013

(54) CHLOROTHIOPHENE-AMIDES AS INHIBITORS OF COAGULATION FACTORS XA AND THROMBIN

(75) Inventors: Markus Follmann, Wülfrath (DE); Volkmar Wehner, Frankfurt am Main (DE); Jerome Meneyrol, Paris (FR); Jean-Michel Altenburger, Paris (FR); Frédéric Petit, Paris (FR); Gilbert Lassalle, Paris (FR); Jean-Pascal Herault, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/858,991

(22) Filed: Aug. 18, 2010

(65) Prior Publication Data

US 2011/0112075 A1 May 12, 2011

Related U.S. Application Data

(63) Continuation of application No. PCT/EP2009/000903, filed on Feb. 10, 2009.

(30) Foreign Application Priority Data

Feb. 21, 2008 (EP) .................................. 08290279

(51) Int. Cl.
*C07D 345/00* (2006.01)
*C07D 517/00* (2006.01)
(52) U.S. Cl. .... 540/1; 540/598; 514/217.05; 514/232.2; 514/235.5; 514/253.11; 514/316; 514/254.01; 514/254.02; 544/130; 544/364; 544/372; 544/131; 544/369; 544/85; 546/187
(58) Field of Classification Search ............... 514/232.2, 514/235.5, 253.11, 254.01, 254.02, 316; 540/598; 546/187; 544/130, 131, 364, 369, 544/372, 85
See application file for complete search history.

(56) References Cited

U.S. PATENT DOCUMENTS

| 5,750,520 | A | 5/1998 | Danilewicz et al. |
| 6,313,242 | B1 | 11/2001 | Reddy |
| 2006/0166985 | A1 | 7/2006 | Borthwick et al. |
| 2007/0129371 | A1 | 6/2007 | Nakamoto et al. |

FOREIGN PATENT DOCUMENTS

| WO | WO 01/38309 A1 | 5/2001 |
| WO | WO 2004/052851 A1 | 6/2004 |
| WO | WO 2004/058728 A1 | 7/2004 |
| WO | WO 2007/056056 A2 | 5/2007 |

OTHER PUBLICATIONS

Patani et al in Chemical Reviews 1996, 96, 3147-3176.*
Falorni et al. in Tetrahedron Letters 39(1998), 9241-9244.*
Baettig U et al., "The Design and Synthesis of Thrombin Inhibitors: Analogues of MD805 Containing Non-Polar Surrogates for Arginine at the P1 Position", *Bioorganic & Medicinal Chemistry Letters* 10(14):1563-1566 (Jul. 17, 2000).
International Search Report dated May 27, 2009 received from the European Patent Office from related International Application No. PCT/EP2009/000903.
Spyropoulos A.C., "Investigational Treatments of Venous Thromboembolism", *Expert Opin. Investig. Drugs* 16(4):431-440 (2007).
J.G. Cannon Chapter Nineteen in Burger's Medicinal Chemistry and Drug Discovery, Fifth Edition, vol. I: *Principles and Practice, Wiley-Interscience* 784:783-802 (1995).
Schäfer S. et al., "Failure is an Option: Learning from Unsuccessful Proof-of-Concept Trials", *Drug Discovery Today* 13(21/22):913-916 (Nov. 2008).
Dörwald F.Z., "Side Reactions in Organic Synthesis—A Guide to Successful Synthesis Design", *Wiley-VCH Verlag GmbH & Co. Weinheim* (2005).
International Search Report dated May 20, 2009 received from the European Patent Office from related International Application No. PCT/EP2009/000902 and U.S. Appl. No. 12/858,981.

* cited by examiner

*Primary Examiner* — Brandon Fetterolf
*Assistant Examiner* — Jean Cornet
(74) *Attorney, Agent, or Firm* — Scully, Scott, Murphy & Presser, P.C.

(57) ABSTRACT

The present invention relates to compounds of the formula I,

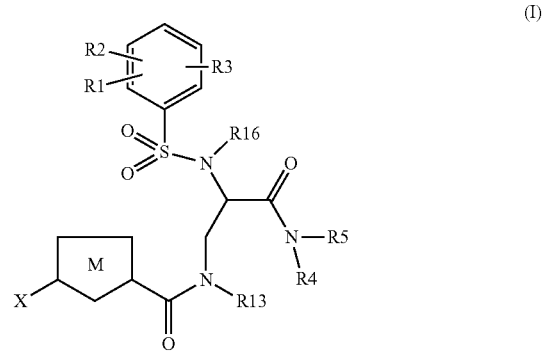

wherein R1; R2; R3; R4; R5, R13, R16, X and M have the meanings indicated in the claims. The compounds of formula I are valuable pharmacologically active compounds. They exhibit a strong anti-thrombotic effect and are suitable, for example, for the therapy and prophylaxis of cardio-vascular disorders like thromboembolic diseases or restenoses. They are reversible inhibitors of the blood clotting enzymes factor Xa (FXa) and thrombin and can in general be applied in conditions in which an undesired activity of factor Xa and/or thrombin are present or for the cure or prevention of which an inhibition of factor Xa and thrombin are intended. The invention furthermore relates to processes for the preparation of compounds of the formula I, their use, in particular as active ingredients in pharmaceuticals, and pharmaceutical preparations comprising them.

9 Claims, No Drawings

CHLOROTHIOPHENE-AMIDES AS INHIBITORS OF COAGULATION FACTORS XA AND THROMBIN

FIELD OF THE INVENTION

The present invention relates to compounds of the formula I,

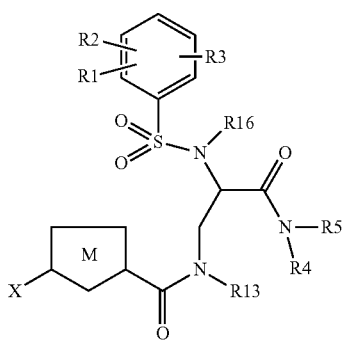

wherein R1; R2; R3; R4; R5, R13, R16, X and M have the meanings indicated below. The compounds of formula I are valuable pharmacologically active compounds. They exhibit a strong anti-thrombotic effect and are suitable, for example, for the therapy and prophylaxis of cardio-vascular disorders like thromboembolic diseases or restenoses. They are reversible inhibitors of the blood clotting enzymes factor Xa (FXa) and thrombin and can in general be applied in conditions in which an undesired activity of factor Xa and/or thrombin are present or for the cure or prevention of which an inhibition of factor Xa and thrombin are intended. The invention furthermore relates to processes for the preparation of compounds of the formula I, their use, in particular as active ingredients in pharmaceuticals, and pharmaceutical preparations comprising them.

BACKGROUND OF THE INVENTION

Normal haemostasis is the result of a complex balance between the processes of clot initiation, formation and clot dissolution. The complex interactions between blood cells, specific plasma proteins and the vascular surface maintain the fluidity of blood unless injury and blood loss occurs. Many significant disease states are related to abnormal haemostasis. For example, local thrombus formation due to rupture of atherosclerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

Thrombotic diseases remain one of the leading causes of death in developed countries despite the availability of anticoagulants such as warfarin, heparin and low molecular weight heparins, and antiplatelet agents such as aspirin and clopidogrel. The oral anticoagulant warfarin inhibits the post-translational maturation of coagulation factors VII, IX, and X and prothrombin and has proven effective in both venous and arterial thrombosis. However, warfarin's usage is limited because of its narrow therapeutic index, slow onset of therapeutic effect, numerous dietary and drug interactions, and a need for monitoring and dose adjustment. This notwithstanding, warfarin remains the standard orally administered anticoagulant available. Patients on warfarin therapy require regular monitoring in part because of its narrow therapeutic index and interactions with food and other drugs. Injectable agents that are also widely used include low molecular weight heparins and the synthetic pentasaccharide fondaparinux. Thus, discovering and developing safe and efficacious oral anticoagulants for the prevention and treatment of a wider range of thrombotic diseases has become increasingly important.

A key strategy for the discovery and development of new anticoagulants has been the targeting of specific enzymes within the blood coagulation cascade. One approach is to inhibit thrombin and thrombin generation by targeting the inhibition of coagulation factor Xa (fXa). Preparations of beta-amino acid-, aspartic acid- and diaminopropionic-benzamides or preparations of heterocycles containing ethylenediamine moiety as activated blood coagulation factor Xa inhibitors were described in International Patent Applications WO 01/038309 and WO 2004/058728. WO2007/056056 discloses similar compounds useful for treating cellular proliferative diseases and disorders by modulating the activity of one or more mitotic kinesins.

Factor Xa, a trypsin-like serine protease, is crucial to the conversion of prothrombin to thrombin, the final enzyme in the coagulation cascade that is responsible for fibrin clot formation. Preclinical animal models have suggested that inhibiting fXa and/or thrombin has the potential for providing excellent antithrombotic efficacy. Even more it has been suggested that dual inhibitors could result in an improved activity when compared to single point inhibition of the coagulation cascade.

DESCRIPTION OF THE INVENTION

The present invention satisfies the above needs by providing compounds of formula I, which exhibit both factor Xa and thrombin inhibitory activity.

Thus, the present invention relates to compounds of the formula I,

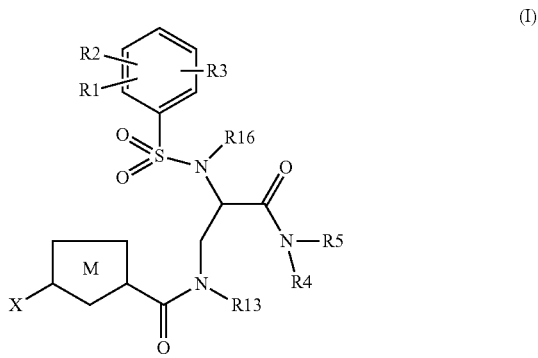

wherein

is a thiophenyl residue,
X is halogen, methyl or ethynyl,

R1, R2 and R3 are independent of one another are identical or different and are a hydrogen atom, —($C_0$-$C_3$)-alkylene-C(O)—R10, —($C_0$-$C_3$)-alkylene-C(O)—NH—R6, —($C_0$-$C_3$)-alkylene-C(O)—N(R21)-R22, —($C_0$-$C_3$)-alkylene-C(O)—O—R10, halogen, —O—($C_1$-$C_4$)-alkyl, —O—($C_1$-$C_3$)-fluoroalkyl, —($C_0$-$C_4$)-alkylene-($C_1$-$C_3$)-fluoroalkyl, —($C_1$-$C_3$)-alkylene-S(O)—R10, —($C_1$-$C_5$)-alkylene-S(O)$_2$—N(R14)-R15, —($C_1$-$C_3$)-alkylene-S(O)$_2$—R10, —($C_0$-$C_5$)-alkylene-($C_3$-$C_8$)-cycloalkyl-R23, —($C_1$-$C_4$)-alkyl, wherein alkyl is unsubstituted or substituted one, two or three times by R8, —($C_0$-$C_4$)-alkylene-aryl, wherein aryl is selected out of the group phenyl, naphthyl, biphenylyl, anthryl or fluorenyl, wherein aryl is mono-, di- or trisubstituted independently of one another by R8, or —($C_0$-$C_4$)-alkylene-heterocyclyl, wherein heterocyclyl is selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8, R4 and R5 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —SO$_t$—R10, wherein t is 1 or 2,
5) —($C_0$-$C_6$)-alkylene-aryl, wherein aryl is as defined above and alkylene and aryl independently from one another are unsubstituted or mono-, di- or trisubstituted by R7,
6) —($C_1$-$C_3$)-fluoroalkyl,
7) —O—($C_1$-$C_4$)-alkyl or
8) —($C_0$-$C_6$)-alkylene-heterocyclyl, wherein heterocyclyl is as defined above and alkylene and heterocyclyl independently from one another are unsubstituted or mono-, di- or trisubstituted by R7, provided that R4 and R5 are not each a hydrogen atom, or R4 and R5 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen, wherein said heterocyclic ring is unsubstituted or mono-, di- or trisubstituted independently of one another by R7, R6 is 1) heterocyclyl, wherein heterocyclyl is as defined above and is un-substituted or mono-, di- or trisubstituted independently of one another by R8 or
2) aryl, which is as defined above wherein aryl is mono-, di- or trisubstituted independently of one another by R8, R7 is halogen, —NO$_2$, =O, —CF$_3$, —($C_0$-$C_3$)-alkylene-C(O)—O—R10, —C(O)—R10, —CN, —OH, —NH$_2$, —C(O)—N(R10)-R20, —N(R10)-R20, =F$_2$, —O—($C_1$-$C_3$)-fluoroalkyl, —($C_0$-$C_4$)-alkylene-($C_1$-$C_3$)-fluoroalkyl, —($C_1$-$C_8$)-alkyl, wherein alkyl is unsubstituted or mono-, di- or trisubstituted independently of one another by halogen, NH$_2$, —OH or —O—($C_1$-$C_6$)-alkyl,
—($C_0$-$C_3$)-alkylene-($C_3$-$C_8$)-cycloalkyl, —O—($C_1$-$C_6$)-alkyl, wherein alkyl is unsubstituted or mono-, di- or trisubstituted independently of one another by halogen, NH$_2$, —OH or a methoxy residue, or
—($C_0$-$C_3$)-alkylene-heterocyclyl, wherein heterocyclyl is as defined above and is unsubstituted mono-, di- or trisubstituted independently of one another by R10, R8 is halogen, —NO$_2$, —CN, =O, —OH, —CF$_3$, —C(O)—O—R10, —C(O)—N(R21)-R22, —N(R21)-R22, —($C_3$-$C_8$)-cycloalkyl, —($C_0$-$C_3$)-alkylene-O—R10, —Si—(CH$_3$)$_3$, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10, —($C_1$-$C_8$)-alkyl, —($C_1$-$C_8$)-alkoxy, phenyl, phenyloxy-, —($C_1$-$C_3$)-fluoroalkyl, —O—R9, —($C_0$-$C_4$)-alkyl-C(O)—O—C(R9, R11)-O—C(O)—R12, —NH—C(O)—NH—R10, —NH—C(O)—NH—R6, —N(R21)-C(O)—R22, —O—CF$_3$, —NH—C(O)—O—R10, or —($C_0$-$C_4$)-alkyl-C(O)—O—C(R9, R11)-O—C(O)—O—R12, R9 and R11 are the same or different and are independently of one another hydrogen, —($C_1$-$C_6$)-alkyl, or together with the carbon atom to which they are bonded form a 3- to 6 membered carbocyclic ring, which is unsubstituted or substituted one, two or three times by R10, R10 and R20 are the same or different and are independently of one another hydrogen atom, halogen, —($C_1$-$C_6$)-alkyl, —($C_0$-$C_4$)-alkyl-OH, —($C_1$-$C_3$)-fluoroalkyl, —($C_0$-$C_4$)-alkyl-O—($C_1$-$C_4$)-alkyl, —($C_0$-$C_5$)-alkyl-($C_3$-$C_8$)-cycloalkyl, —($C_0$-$C_2$)-alkylene-aryl, wherein aryl is as defined above and aryl is unsubstituted or substituted one, two or three times of each other by —($C_1$-$C_6$)-alkyl, halogen or —($C_3$-$C_8$)-cycloalkyl, or —($C_0$-$C_2$)-alkylene-heterocyclyl, wherein heterocyclyl is as defined above and heterocyclyl is unsubstituted or substituted one, two or three times independent of each other by —($C_1$-$C_6$)-alkyl, halogen or —($C_3$-$C_8$)-cycloalkyl, R12 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or R10, R13 is hydrogen atom, —OH or —O—($C_1$-$C_4$)-alkyl, R14 and R15 are the same or different and are independently of one another hydrogen atom or —($C_1$-$C_4$)-alkyl, R16 is hydrogen atom, —OH or —O—($C_1$-$C_4$)-alkyl, R21 and R22 are the same or different and are independently of one another
1) hydrogen atom,
2) —($C_1$-$C_6$)-alkyl, wherein alkyl is unsubstituted or mono-, di- or trisubstituted independently of one another by R8,
3) —($C_0$-$C_6$)-alkylene-($C_3$-$C_8$)-cycloalkyl,
4) —$SO_t$—R10, wherein t is 1 or 2,
5) —($C_0$-$C_6$)-alkylene-aryl, wherein aryl is as defined above and alkylene and aryl independently from one another are unsubstituted or mono-, di- or trisubstituted by R8,
6) —($C_1$-$C_3$)-fluoroalkyl,
7) —O—R12 or
8) —($C_0$-$C_6$)-alkylene-heterocyclyl, wherein heterocyclyl is as defined above and alkylene and heterocyclyl independently from one another are unsubstituted or mono-, di- or trisubstituted by R8, or R21 and R22 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen, wherein said heterocyclic ring is unsubstituted or mono-, di- or trisubstituted independently of one another by R8, and R23 is hydrogen atom, —OH or —O—($C_1$-$C_4$)-alkyl, in all its stereoisomeric forms and mixtures thereof in any ratio, and its physiologically tolerable salts.

2) Thus, the present invention also relates to compounds of the formula I, wherein

is a thiophenyl residue,

X is halogen, methyl or ethynyl,

R1 is —($C_0$-$C_3$)-alkylene-C(O)—R10, —($C_0$-$C_3$)-alkylene-C(O)—NH—R6, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl, —($C_1$-$C_4$)-alkyl, wherein alkyl is unsubstituted or substituted one, two or three times by R8,
—($C_0$-$C_5$)-alkylene-($C_3$-$C_8$)-cycloalkyl-R23, —($C_0$-$C_4$)-alkylene-aryl, wherein aryl is selected out of the group phenyl, naphthyl, biphenylyl, anthryl or fluorenyl, wherein aryl is mono-, di- or trisubstituted independently of one another by R8, or
—($C_0$-$C_4$)-alkylene-heterocyclyl, wherein heterocyclyl is selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8, R2 and R3 are independent of one another are identical or different and are a hydrogen atom, —($C_0$-$C_3$)-alkylene-C(O)—R10, —($C_0$-$C_3$)-alkylene-C(O)—NH—R6, —($C_0$-$C_3$)-alkylene-C(O)—O—R10, —O—($C_1$-$C_4$)-alkyl, —O—($C_1$-$C_3$)-fluoroalkyl, halogen, —($C_0$-$C_4$)-alkylene-($C_1$-$C_3$)-fluoroalkyl, —($C_0$-$C_5$)-alkylene-($C_3$-$C_8$)-cycloalkyl-R23,
—($C_1$-$C_4$)-alkyl, wherein alkyl is unsubstituted or substituted one, two or three times by R8,
—($C_0$-$C_4$)-alkylene-aryl, wherein aryl is as defined above and is mono-, di- or trisubstituted independently of one another by R8, or
—($C_0$-$C_4$)-alkylene-heterocyclyl, wherein heterocyclyl is as defined above and is unsubstituted or mono-, di- or trisubstituted independently of one another by R8, R4 and R5 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —$SO_t$—R10, wherein t is 1 or 2, 5) —(C$_0$-C$_6$)-alkylene-aryl, wherein aryl is as defined above and alkylene and aryl independently from one another are unsubstituted or mono-, di- or trisubstituted by R7,
6) —(C$_1$-C$_3$)-fluoroalkyl,
7) —O—(C$_1$-C$_4$)-alkyl or
8) —(C$_0$-C$_6$)-alkylene-heterocyclyl, wherein heterocyclyl is as defined above and alkylene and heterocyclyl independently from one another are unsubstituted or mono-, di- or trisubstituted by R7, provided that R4 and R5 are not each a hydrogen atom, or R4 and R5 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen, wherein said heterocyclic ring is unsubstituted or mono-, di- or trisubstituted independently of one another by R7, R6 is 1) heterocyclyl, wherein heterocyclyl is as defined above and is un-substituted or mono-, di- or trisubstituted independently of one another by R8 or
2) aryl, which is as defined above wherein aryl is mono-, di- or trisubstituted independently of one another by R8, R7 is halogen, —NO$_2$, =O, —CF$_3$, —(C$_0$-C$_3$)-alkylene-C(O)—O—R10, —C(O)—R10, —CN, —OH, —NH$_2$, —C(O)—N(R10)-R20, —N(R10)-R20, =F$_2$, —O—(C$_1$-C$_3$)-fluoroalkyl, —(C$_0$-C$_4$)-alkylene-(C$_1$-C$_3$)-fluoroalkyl, —(C$_1$-C$_8$)-alkyl, wherein alkyl is unsubstituted or mono-, di- or trisubstituted independently of one another by halogen, NH$_2$, —OH or —O—(C$_1$-C$_6$)-alkyl,
—(C$_0$-C$_3$)-alkylene-(C$_3$-C$_8$)-cycloalkyl, —O—(C$_1$-C$_6$)-alkyl, wherein alkyl is unsubstituted or mono-, di- or trisubstituted independently of one another by halogen, NH$_2$, —OH or a methoxy residue, or
—(C$_0$-C$_3$)-alkylene-heterocyclyl, wherein heterocyclyl is as defined above and is unsubstituted mono-, di- or trisubstituted independently of one another by R10, R8 is halogen, —NO$_2$, —CN, =O, —OH, —CF$_3$, —C(O)—O—R10, —(C$_3$-C$_8$)-cycloalkyl, —(C$_0$-C$_3$)-alkylene-O—R10, —Si—(CH$_3$)$_3$, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10, —(C$_1$-C$_8$)-alkyl, —(C$_1$-C$_8$)-alkoxy, phenyl, phenyloxy-, —O—R9, —(C$_1$-C$_3$)-fluoroalkyl, —(C$_0$-C$_4$)-alkyl-C(O)—O—C(R9, R11)-O—C(O)—R12, —NH—C(O)—NH—R10, —NH—C(O)—NH—R6, —O—CF$_3$, —NH—C(O)—O—R10, or —(C$_0$-C$_4$)-alkyl-C(O)—O—C(R9, R11)-O—C(O)—O—R12, R9 and R11 are the same or different and are independently of one another hydrogen, —(C$_1$-C$_6$)-alkyl, or together with the carbon atom to which they are bonded form a 3- to 6 membered carbocyclic ring, which is unsubstituted or substituted one, two or three times by R10, R10 and R20 are the same or different and are independently of one another hydrogen atom, halogen, —(C$_1$-C$_6$)-alkyl, —(C$_0$-C$_4$)-alkyl-OH, —(C$_1$-C$_3$)-fluoroalkyl, —(C$_0$-C$_4$)-alkyl-O—(C$_1$-C$_4$)-alkyl, —(C$_0$-C$_5$)-alkyl-(C$_3$-C$_8$)-cycloalkyl, —(C$_0$-C$_2$)-alkylene-aryl, wherein aryl is as defined above and aryl is unsubstituted or substituted one, two or three times independent of each other by —(C$_1$-C$_6$)-alkyl, halogen or —(C$_3$-C$_8$)-cycloalkyl, or —(C$_0$-C$_2$)-alkylene-heterocyclyl, wherein heterocyclyl is as defined above and heterocyclyl is unsubstituted or substituted one, two or three times independent of each other by —(C$_1$-C$_6$)-alkyl, halogen or —(C$_3$-C$_8$)-cycloalkyl, R12 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R10, R13 is hydrogen atom, —OH or —O—(C$_1$-C$_4$)-alkyl,
R16 is hydrogen atom, —OH or —O—(C$_1$-C$_4$)-alkyl, and
R23 is hydrogen atom, —OH or —O—(C$_1$-C$_4$)-alkyl, in all its stereoisomeric forms and mixtures thereof in any ratio, and its physiologically tolerable salts.

3) Thus, the present invention also relates to compounds of the formula I, wherein

is a thiophenyl residue,
X is halogen, methyl or ethynyl,
R1 is —(C$_0$-C$_3$)-alkylene-C(O)—R10, —(C$_0$-C$_3$)-alkylene-C(O)—NH—R6, halogen, —(C$_0$-C$_3$)-alkylene-C(O)—O—R10, —O—(C$_1$-C$_4$)-alkyl, —O—(C$_1$-C$_3$)-fluoroalkyl, —(C$_0$-C$_4$)-alkylene-(C$_1$-C$_3$)-fluoroalkyl or —(C$_1$-C$_4$)-alkyl, wherein alkyl is unsubstituted or substituted one, two or three times by R8,
R2 is —(C$_0$-C$_3$)-alkylene-C(O)—R10, —(C$_0$-C$_3$)-alkylene-C(O)—NH—R6, halogen, —(C$_0$-C$_3$)-alkylene-C(O)—O—R10, —O—(C$_1$-C$_4$)-alkyl, —O—(C$_1$-C$_3$)-fluoroalkyl, —(C$_0$-C$_4$)-alkylene-(C$_1$-C$_3$)-fluoroalkyl or —(C$_1$-C$_4$)-alkyl, wherein alkyl is unsubstituted or substituted one, two or three times by R8,
—(C$_0$-C$_5$)-alkylene-(C$_3$-C$_8$)-cycloalkyl-R23, —(C$_0$-C$_4$)-alkylene-aryl, wherein aryl is selected out of the group phenyl, naphthyl, biphenylyl, anthryl or fluorenyl, wherein aryl is mono-, di- or trisubstituted independently of one another by R8, or
—(C$_0$-C$_4$)-alkylene-heterocyclyl, wherein heterocyclyl is selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8, R3 is a hydrogen atom, —($C_0$-$C_3$)-alkylene-C(O)—R10, —($C_0$-$C_3$)-alkylene-C(O)—NH—R6, —($C_0$-$C_3$)-alkylene-C(O)—O—R10, —O—($C_1$-$C_4$)-alkyl, —O—($C_1$-$C_3$)-fluoroalkyl, halogen, —($C_0$-$C_4$)-alkylene-($C_1$-$C_3$)-fluoroalkyl, —($C_0$-$C_5$)-alkylene-($C_3$-$C_8$)-cycloalkyl-R23, or —($C_1$-$C_4$)-alkyl, wherein alkyl is unsubstituted or substituted one, two or three times by R8, R4 and R5 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —$SO_t$—R10, wherein t is 1 or 2,
5) —($C_0$-$C_6$)-alkylene-aryl, wherein aryl is as defined above and alkylene and aryl independently from one another are unsubstituted or mono-, di- or trisubstituted by R7,
6) —($C_1$-$C_3$)-fluoroalkyl,
7) —O—($C_1$-$C_4$)-alkyl or
8) —($C_0$-$C_6$)-alkylene-heterocyclyl, wherein heterocyclyl is as defined above and alkylene and heterocyclyl independently from one another are unsubstituted or mono-, di- or trisubstituted by R7,
provided that R4 and R5 are not each a hydrogen atom, or
R4 and R5 together with the nitrogen atom to which they are bonded form a 4- to 10-membered mono- or bicyclic heterocyclic ring, which is selected from 2-oxa-5-aza-bicyclo[2.2.1]heptane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R7, R6 is 1) heterocyclyl, wherein heterocyclyl is as defined above and is un-substituted or mono-, di- or trisubstituted independently of one another by R8 or
2) aryl, which is as defined above wherein aryl is mono-, di- or trisubstituted independently of one another by R8, R7 is halogen, —$NO_2$, =O, —$CF_3$, —($C_0$-$C_3$)-alkylene-C(O)—O—R10, —C(O)—R10, —CN, —OH, —$NH_2$, —C(O)—N(R10)-R20, —N(R10)-R20, =$F_2$, —O—($C_1$-$C_3$)-fluoroalkyl, —($C_0$-$C_4$)-alkylene-($C_1$-$C_3$)-fluoroalkyl, —($C_1$-$C_8$)-alkyl, wherein alkyl is unsubstituted or mono-, di- or trisubstituted independently of one another by halogen, $NH_2$, —OH or —O—($C_1$-$C_6$)-alkyl,
—($C_0$-$C_3$)-alkylene-($C_3$-$C_8$)-cycloalkyl, —O—($C_1$-$C_6$)-alkyl, wherein alkyl is unsubstituted or mono-, di- or trisubstituted independently of one another by halogen, $NH_2$, —OH or a methoxy residue, or
—($C_0$-$C_3$)-alkylene-heterocyclyl, wherein heterocyclyl is as defined above and is unsubstituted mono-, di- or trisubstituted independently of one another by R10, R8 is halogen, —$NO_2$, —CN, =O, —OH, —$CF_3$, —C(O)—O—R10, —($C_3$-$C_8$)-cycloalkyl, —($C_0$-$C_3$)-alkylene-O—R10, —Si—($CH_3$)$_3$, —N(R10)-S(O)$_u$—R10, wherein u is 1 or 2, —S—R10, —$SO_r$—R10, wherein r is 1 or 2, —S(O)$_v$—N(R10)-R20, wherein v is 1 or 2, —C(O)—R10, —($C_1$-$C_8$)-alkyl, —($C_1$-$C_8$)-alkoxy, phenyl, phenyloxy-, —O—$CF_3$, —($C_1$-$C_3$)-fluoroalkyl, —NH—C(O)—NH—R6 or —NH—C(O)—O—R10, R10 and R20 are the same or different and are independently of one another hydrogen atom, halogen, —($C_1$-$C_6$)-alkyl, —($C_0$-$C_4$)-alkyl-OH, —($C_1$-$C_3$)-fluoroalkyl, —($C_0$-$C_4$)-alkyl-O—($C_1$-$C_4$)-alkyl, —($C_0$-$C_5$)-alkyl-($C_3$-$C_8$)-cycloalkyl, —($C_0$-$C_2$)-alkylene-aryl, wherein aryl is as defined above and aryl is unsubstituted or substituted one, two or three times independent of each other by —($C_1$-$C_6$)-alkyl, halogen or —($C_3$-$C_8$)-cycloalkyl, or —($C_0$-$C_2$)-alkylene-heterocyclyl, wherein heterocyclyl is as defined above and heterocyclyl is unsubstituted or substituted one, two or three times independent of each other by —($C_1$-$C_6$)-alkyl, halogen or —($C_3$-$C_8$)-cycloalkyl, R13 is hydrogen atom, —OH or —O—($C_1$-$C_4$)-alkyl,
R16 is hydrogen atom, —OH or —O—($C_1$-$C_4$)-alkyl, and
R23 is hydrogen atom, —OH or —O—($C_1$-$C_4$)-alkyl,
in all its stereoisomeric forms and mixtures thereof in any ratio, and its physiologically tolerable salts.

The present invention also relates to compounds of the formula I, wherein

is a thiophenyl residue,
X is halogen,
R1 is when anchored in the 2-position hydrogen atom, halogen, —O—($C_1$-$C_4$)-alkyl, —O—($C_1$-$C_3$)-fluoroalkyl, —($C_0$-$C_4$)-alkylene-($C_1$-$C_3$)-fluoroalkyl, —($C_0$-$C_5$)-alkylene-($C_3$-$C_8$)-cycloalkyl-R23 or —($C_1$-$C_4$)-alkyl,
R2 is when anchored in the 3-position hydrogen atom, —($C_0$-$C_3$)-alkylene-C(O)—R10, —($C_0$-$C_3$)-alkylene-C(O)—NH—R6, halogen, —($C_0$-$C_3$)-alkylene-C(O)—N(R21)-R22, —($C_0$-$C_3$)-alkylene-C(O)—O—R10, —O—($C_1$-$C_4$)-alkyl, —O—($C_1$-$C_3$)-fluoroalkyl, —($C_0$-$C_4$)- alkylene-($C_1$-$C_3$)-fluoroalkyl, —($C_1$-$C_3$)-alkylene-S(O)—R10, —($C_1$-$C_5$)-alkylene-S(O)$_2$—N(R14)-R15, —($C_1$-$C_3$)-alkylene-S(O)$_2$—R10, —($C_0$-$C_5$)-alkylene-($C_3$-$C_8$)-cycloalkyl-R23, —($C_1$-$C_4$)-alkyl, wherein alkyl is unsubstituted or substituted one, two or three times by R8, —($C_0$-$C_4$)-alkylene-phenyl, wherein phenyl is mono-, di- or trisubstituted independently by R8, or —($C_0$-$C_4$)-alkylene-heterocyclyl, wherein heterocyclyl is selected out of the group azabenzimidazolyl, azepinyl, azetidinyl, aziridinyl, benzimidazolyl, benzofuranyl, benzothienyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, chromanyl, chromenyl, decahydro-quinolinyl, 4,5-dihydrooxa-zolinyl, dioxazolyl, dioxazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketomorpholinyl, ketopiperidinyl, ketopiperazinyl, ketopyrrolidinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, purinyl, pyranyl, pyrazinyl, pyrazolidinyl, pyrazolinyl, pyrazolyl, pyridazinyl, pyridoimidazolyl, 2-pyridone, 4-pyridone, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thioketomorpholinyl, thioketopiperidinyl, thioketopiperazinyl, thioketopyrrolidinyl, thiomorpholinyl, thiophenolyl, thiophenyl, 1,2,3-triazinyl, 1,2,4-triazinyl, 1,3,5-triazinyl, 1,2,3-triazolyl, 1,2,4-triazolyl, 1,2,5-triazolyl and 1,3,4-triazolyl, and wherein said heterocyclyl is unsubstituted or mono-, di- or trisubstituted independently of one another by R8, R1 and R2 together with the carbon atoms to which they are each bonded form a bicyclic aryl or heterocyclic ring selected from the group alpha-naphthyl, beta-naphthyl, quinolyl, isoquinolyl and indolyl, R3 is when anchored in the 6-position hydrogen atom or halogen, when anchored in the 5-position hydrogen atom or halogen, or when anchored in the 4-position hydrogen atom —($C_0$-$C_4$)-alkylene-phenyl, wherein phenyl is mono-, di- or trisubstituted independently by R8, or —($C_0$-$C_4$)-alkylene-heterocyclyl, wherein heterocyclyl is selected out of the group azabenzimidazolyl, azepinyl, azetidinyl, aziridinyl, benzimidazolyl, benzofuranyl, benzothienyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, chromanyl, chromenyl, decahydro-quinolinyl, 4,5-dihydrooxa-zolinyl, dioxazolyl, dioxazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyridyl N-oxide, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thiomorpholinyl, thiophenolyl, thiophenyl, 1,2,3-triazinyl, 1,2,4-triazinyl, 1,3,5-triazinyl, 1,2,3-triazolyl, 1,2,4-triazolyl, 1,2,5-triazolyl and 1,3,4-triazolyl, and wherein said heterocyclyl is unsubstituted or mono-, di- or trisubstituted independently of one another by R8, R4 and R5 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —SO$_t$—R10, wherein t is 1 or 2,
5) —($C_0$-$C_6$)-alkylene-aryl, wherein alkylene and aryl independently from one another are unsubstituted or mono-, di- or trisubstituted by R7,
6) —($C_1$-$C_3$)-fluoroalkyl,
7) —O—($C_1$-$C_4$)-alkyl or
8) —($C_0$-$C_6$)-alkylene-heterocyclyl, wherein heterocyclyl and alkylene independently from one another are unsubstituted or mono-, di- or trisubstituted by R7, provided that R4 and R5 are not each a hydrogen atom, or
R4 and R5 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen, wherein said heterocyclic ring is unsubstituted or mono-, di- or trisubstituted independently of one another by R7, R6 is 1) heterocyclyl, wherein heterocyclyl is un-substituted or mono-, di- or trisubstituted independently of one another by R8 or
2) aryl, wherein aryl is mono-, di- or trisubstituted independently of one another by R8, R7 is halogen, —$NO_2$, =O, —$CF_3$, —($C_0$-$C_3$)-alkylene-C(O)—O—R10, —C(O)—R10, —CN, —OH, —$NH_2$, —C(O)—N(R10)-R20, —N(R10)-R20, =$F_2$, —O—($C_1$-$C_3$)-fluoroalkyl, —($C_0$-$C_4$)-alkylene-($C_1$-$C_3$)-fluoroalkyl, —($C_1$-$C_8$)-alkyl, wherein alkyl is unsubstituted or mono-, di- or trisubstituted independently of one another by halogen, $NH_2$, —OH or —O—($C_1$-$C_6$)-alkyl,
—($C_0$-$C_3$)-alkylene-($C_3$-$C_8$)-cycloalkyl, —O—($C_1$-$C_6$)-alkyl, wherein alkyl is unsubstituted or mono-, di- or trisubstituted independently of one another by halogen, $NH_2$, —OH or a methoxy residue, or
—($C_0$-$C_3$)-alkylene-heterocyclyl, wherein heterocyclyl is as defined above and is unsubstituted mono-, di- or trisubstituted independently of one another by R10, R8 is halogen, —$NO_2$, —CN, —OH, —$CF_3$, —C(O)—O—R10, —C(O)—N(R21)-R22, —N(R21)-R22, —($C_3$-$C_8$)-cycloalkyl, —($C_0$-$C_3$)-alkylene-O—R10, —Si—$(CH_3)_3$, —N(R10)-S(O)$_u$—R10, wherein u is 1 or 2, —S—R10, —$SO_r$—R10, wherein r is 1 or 2, —S(O)$_v$—N(R10)-R20, wherein v is 1 or 2, —C(O)—R10, —($C_1$-$C_8$)-alkyl, —($C_1$-$C_8$)-alkoxy, phenyl, phenyloxy-, —($C_1$-$C_3$)-fluoroalkyl, —O—R9, —($C_0$-$C_4$)-alkyl-C(O)—O—C(R9, R11)-O—C(O)—R12, —NH—C(O)—NH—R10, —NH—C(O)—NH—R6, —N(R21)-C(O)—R22, —O—$CF_3$, —NH—C(O)—O—R10, or —($C_0$-$C_4$)-alkyl-C(O)—O—C(R9, R11)-O—C(O)—O—R12, R9 and R11 are the same or different and are independently of one another hydrogen atom, —($C_1$-$C_6$)-alkyl, or together with the carbon atom to which they are bonded form a 3- to 6 membered carbocyclic ring, which is unsubstituted or substituted one, two or three times by R10, R10 and R20 are the same or different and are independently of one another hydrogen atom, —($C_1$-$C_6$)-alkyl, —($C_0$-$C_4$)-alkyl-OH, —($C_1$-$C_3$)-fluoroalkyl, —($C_0$-$C_4$)-alkyl-O—($C_1$-$C_4$)-alkyl, —($C_0$-$C_5$)-alkyl-($C_3$-$C_8$)-cycloalkyl, —($C_0$-$C_2$)-alkylene-aryl, wherein aryl is unsubstituted or substituted one, two or three times independent of each other by —($C_1$-$C_6$)-alkyl, halogen or —($C_3$-$C_8$)-cycloalkyl, or —($C_0$-$C_2$)-alkylene-heterocyclyl, wherein heterocyclyl is unsubstituted or substituted one, two or three times independent of each other by —($C_1$-$C_6$)-alkyl, halogen or —($C_3$-$C_8$)-cycloalkyl, R12 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or R10, R13 is hydrogen atom or —($C_1$-$C_4$)-alkyl, R14 and R15 are the same or different and are independently of one another hydrogen atom or —($C_1$-$C_4$)-alkyl, R16 is hydrogen atom or —($C_1$-$C_4$)-alkyl, R21 and R22 are the same or different and are independently of one another
1) hydrogen atom,
2) —($C_1$-$C_6$)-alkyl, wherein alkyl is unsubstituted or mono-, di- or trisubstituted independently of one another by R8,
3) —($C_0$-$C_6$)-alkylene-($C_3$-$C_8$)-cycloalkyl,
4) —$SO_t$—R10, wherein t is 1 or 2,
5) —($C_0$-$C_6$)-alkylene-aryl, wherein alkylene and aryl independently from one another are unsubstituted or mono-, di- or trisubstituted by R8,
6) —($C_1$-$C_3$)-fluoroalkyl,
7) —O—R12 or
8) —($C_0$-$C_6$)-alkylene-heterocyclyl, wherein alkylene and heterocyclyl independently from one another are unsubstituted or mono-, di- or trisubstituted by R8, or R21 and R22 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen, wherein said heterocyclic ring is unsubstituted or mono-, di- or trisubstituted independently of one another by R8, and R23 is hydrogen atom or —($C_0$-$C_3$)-alkylene-O—R10, in all its stereoisomeric forms and mixtures thereof in any ratio, and its physiologically tolerable salts.

4) Thus, the present invention also relates to compounds of the formula Ia,

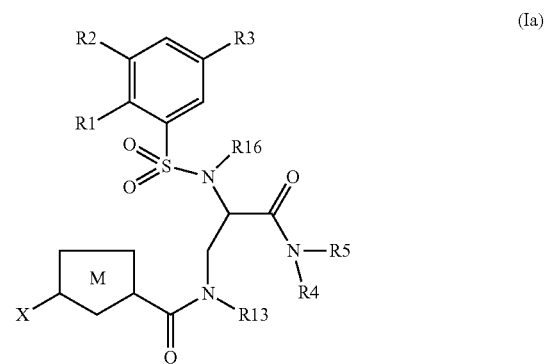

(Ia)

wherein

is a thiophenyl residue,

X is halogen, methyl or ethynyl,

R1 is —($C_0$-$C_3$)-alkylene-C(O)—R10, —($C_0$-$C_3$)-alkylene-C(O)—NH—R6, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl or —($C_1$-$C_4$)-alkyl, wherein alkyl is unsubstituted or substituted one, two or three times by R8, R2 is —($C_0$-$C_3$)-alkylene-C(O)—R10, —($C_0$-$C_3$)-alkylene-C(O)—NH—R6, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl or —($C_1$-$C_4$)-alkyl, wherein alkyl is unsubstituted or substituted one, two or three times by R8,
—($C_0$-$C_5$)-alkylene-($C_3$-$C_8$)-cycloalkyl-R23, —($C_0$-$C_4$)-alkylene-aryl, wherein aryl is selected out of the group phenyl, naphthyl, biphenylyl, anthryl or fluorenyl, wherein aryl is mono-, di- or trisubstituted independently of one another by R8, or
—($C_0$-$C_4$)-alkylene-heterocyclyl, wherein heterocyclyl is selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8, R3 is a hydrogen atom, —($C_0$-$C_3$)-alkylene-C(O)—R10, —($C_0$-$C_3$)-alkylene-C(O)—NH—R6, —($C_0$-$C_3$)-alkylene-C(O)—O—R10, —O—($C_1$-$C_4$)-alkyl, —O—($C_1$-$C_3$)-fluoroalkyl, halogen, —($C_0$-$C_4$)-alkylene-($C_1$-$C_3$)-fluoroalkyl, —($C_0$-$C_5$)-alkylene-($C_3$-$C_8$)-cycloalkyl-R23, or —($C_1$-$C_4$)-alkyl, wherein alkyl is unsubstituted or substituted one, two or three times by R8, R4 and R5 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —SO$_t$—R10, wherein t is 1 or 2,
5) —($C_0$-$C_6$)-alkylene-aryl, wherein aryl is as defined above and alkylene and aryl independently from one another are unsubstituted or mono-, di- or trisubstituted by R7,
6) —($C_1$-$C_3$)-fluoroalkyl,
7) —O—($C_1$-$C_4$)-alkyl or
8) —($C_0$-$C_6$)-alkylene-heterocyclyl, wherein heterocyclyl is as defined above and alkylene and heterocyclyl independently from one another are unsubstituted or mono-, di- or trisubstituted by R7, provided that R4 and R5 are not each a hydrogen atom, or R4 and R5 together with the nitrogen atom to which they are bonded form a 4- to 10-membered mono- or bicyclic heterocyclic ring, which is selected from 2-oxa-5-aza-bicyclo[2.2.1]heptane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R7, R6 is 1) heterocyclyl, wherein heterocyclyl is as defined above and is un-substituted or mono-, di- or trisubstituted independently of one another by R8 or
2) aryl, which is as defined above wherein aryl is mono-, di- or trisubstituted independently of one another by R8, R7 is halogen, —NO$_2$, =O, —CF$_3$, —($C_0$-$C_3$)-alkylene-C(O)—O—R10, —C(O)—R10, —CN, —OH, —NH$_2$, —C(O)—N(R10)-R20, —N(R10)-R20, =F$_2$, —O—($C_1$-$C_3$)-fluoroalkyl, —($C_0$-$C_4$)-alkylene-($C_1$-$C_3$)-fluoroalkyl, —($C_1$-$C_8$)-alkyl, wherein alkyl is unsubstituted or mono-, di- or trisubstituted independently of one another by halogen, NH$_2$, —OH or —O—($C_1$-$C_6$)-alkyl,
—($C_0$-$C_3$)-alkylene-($C_3$-$C_8$)-cycloalkyl, —O—($C_1$-$C_6$)-alkyl, wherein alkyl is unsubstituted or mono-, di- or trisubstituted independently of one another by halogen, NH$_2$, —OH or a methoxy residue, or
—($C_0$-$C_3$)-alkylene-heterocyclyl, wherein heterocyclyl is as defined above and is unsubstituted mono-, di- or trisubstituted independently of one another by R10, R8 is halogen, —NO$_2$, —CN, =O, —OH, —CF$_3$, —C(O)—O—R10, —($C_3$-$C_8$)-cycloalkyl, —($C_0$-$C_3$)-alkylene-O—R10, —Si—(CH$_3$)$_3$, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10, —($C_1$-$C_8$)-alkyl, —($C_1$-$C_8$)-alkoxy, phenyl, phenyloxy-, —O—CF$_3$, —($C_1$-$C_3$)-fluoroalkyl, —NH—C(O)—NH—R6 or —NH—C(O)—O—R10, R10 and R20 are the same or different and are independently of one another hydrogen atom, halogen, —($C_1$-$C_6$)-alkyl, —($C_0$-$C_4$)-alkyl-OH, —($C_1$-$C_3$)-fluoroalkyl, —($C_0$-$C_4$)-alkyl-O—($C_1$-$C_4$)-alkyl, —($C_0$-$C_5$)-alkyl-($C_3$-$C_8$)-cycloalkyl, —($C_0$-$C_2$)-alkylene-aryl, wherein aryl is as defined above and aryl is unsubstituted or substituted one, two or three times independent of each other by —($C_1$-$C_6$)-alkyl, halogen or —($C_3$-$C_8$)-cycloalkyl, or —($C_0$-$C_2$)- alkylene-heterocyclyl, wherein heterocyclyl is as defined above and heterocyclyl is unsubstituted or substituted one, two or three times independent of each other by —(C$_1$-C$_6$)-alkyl, halogen or —(C$_3$-C$_8$)-cycloalkyl, R13 is hydrogen atom, —OH or —O—(C$_1$-C$_4$)-alkyl,
R16 is hydrogen atom, —OH or —O—(C$_1$-C$_4$)-alkyl, and
R23 is hydrogen atom, —OH or —O—(C$_1$-C$_4$)-alkyl,
in all its stereoisomeric forms and mixtures thereof in any ratio, and its physiologically tolerable salts.

5) Thus, the present invention also relates to compounds of the formula Ia, wherein

is a thiophenyl residue,

X is halogen, methyl or ethynyl,

R1 is —(C$_0$-C$_3$)-alkylene-C(O)—R10, halogen, —(C$_0$-C$_3$)-alkylene-C(O)—O—R10, —O—(C$_1$-C$_4$)-alkyl, —O—(C$_1$-C$_3$)-fluoroalkyl, —(C$_0$-C$_4$)-alkylene-(C$_1$-C$_3$)-fluoroalkyl or —(C$_1$-C$_4$)-alkyl, wherein alkyl is unsubstituted or substituted one, two or three times by R8, R2 is —(C$_0$-C$_3$)-alkylene-C(O)—R10, halogen, —(C$_0$-C$_3$)-alkylene-C(O)—O—R10, —O—(C$_1$-C$_4$)-alkyl, —O—(C$_1$-C$_3$)-fluoroalkyl, —(C$_0$-C$_4$)-alkylene-(C$_1$-C$_3$)-fluoroalkyl or —(C$_1$-C$_4$)-alkyl, wherein alkyl is unsubstituted or substituted one, two or three times by R8, —(C$_0$-C$_4$)-alkylene-aryl, wherein aryl is selected out of the group phenyl, naphthyl, biphenylyl, anthryl or fluorenyl, wherein aryl is mono-, di- or trisubstituted independently of one another by R8, or —(C$_0$-C$_4$)-alkylene-heterocyclyl, wherein heterocyclyl is selected out of the group morpholinyl, oxadiazolyl, 1,2,4-oxadiazolyl, 1,3,4-oxadiazolyl, 1,4-oxazepanyl, piperidinyl, pyrazolyl, pyridyl, pyrrolidinyl or thiazolyl, and wherein said heterocyclyl is unsubstituted or mono-, di- or trisubstituted independently of one another by R8, R3 is a hydrogen atom, —(C$_0$-C$_3$)-alkylene-C(O)—R10, —(C$_0$-C$_3$)-alkylene-C(O)—O—R10, —O—(C$_1$-C$_4$)-alkyl, —O—(C$_1$-C$_3$)-fluoroalkyl, halogen, —(C$_0$-C$_4$)-alkylene-(C$_1$-C$_3$)-fluoroalkyl or —(C$_1$-C$_4$)-alkyl, wherein alkyl is unsubstituted or substituted one, two or three times by R8, R4 and R5 are the same or different and are independently of one another
1) hydrogen atom,
2) —(C$_1$-C$_6$)-alkyl, wherein alkyl is unsubstituted or mono-, di- or trisubstituted independently of one another by R7,
3) —(C$_0$-C$_6$)-alkylene-(C$_3$-C$_8$)-cycloalkyl,
4) —SO$_t$—R10, wherein t is 1 or 2,
5) —(C$_0$-C$_6$)-alkylene-aryl, wherein aryl is as defined above and alkylene and aryl independently from one another are unsubstituted or mono-, di- or trisubstituted by R7,
6) —(C$_1$-C$_3$)-fluoroalkyl,
7) —O—(C$_1$-C$_4$)-alkyl or
8) —(C$_0$-C$_6$)-alkylene-heterocyclyl, wherein heterocyclyl is as defined above and alkylene and heterocyclyl independently from one another are unsubstituted or mono-, di- or trisubstituted by R7,
provided that R4 and R5 are not each a hydrogen atom, or
R4 and R5 together with the nitrogen atom to which they are bonded form a 4- to 10-membered mono- or bicyclic heterocyclic ring, which is selected from 2-oxa-5-aza-bicyclo[2.2.1]heptane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R7, R7 is halogen, —NO$_2$, =O, —CF$_3$, —(C$_0$-C$_3$)-alkylene-C(O)—O—R10, —C(O)—R10, —CN, —OH, —NH$_2$, —C(O)—N(R10)-R20, —N(R10)-R20, =F$_2$, —O—(C$_1$-C$_3$)-fluoroalkyl, —(C$_0$-C$_4$)-alkylene-(C$_1$-C$_3$)-fluoroalkyl, —(C$_1$-C$_8$)-alkyl, wherein alkyl is unsubstituted or mono-, di- or trisubstituted independently of one another by halogen, NH$_2$, —OH or —O—(C$_1$-C$_6$)-alkyl,
—(C$_0$-C$_3$)-alkylene-(C$_3$-C$_8$)-cycloalkyl, —O—(C$_1$-C$_6$)-alkyl, wherein alkyl is unsubstituted or mono-, di- or trisubstituted independently of one another by halogen, NH$_2$, —OH or a methoxy residue, or
—(C$_0$-C$_3$)-alkylene-heterocyclyl, wherein heterocyclyl is as defined above and is unsubstituted mono-, di- or trisubstituted independently of one another by R10, R8 is halogen, —NO$_2$, —CN, =O, —OH, —CF$_3$, —C(O)—O—R10, —(C$_3$-C$_8$)-cycloalkyl, —(C$_0$-C$_3$)-alkylene-O—R10, —Si—(CH$_3$)$_3$, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10, —(C$_1$-C$_8$)-alkyl, —(C$_1$-C$_8$)-alkoxy, phenyl, phenyloxy-, —O—CF$_3$, —(C$_1$-C$_3$)-fluoroalkyl or —NH—C(O)—O—R10, R10 and R20 are the same or different and are independently of one another hydrogen atom, halogen, —(C$_1$-C$_6$)-alkyl, —(C$_0$-C$_4$)-alkyl-OH, —(C$_1$-C$_3$)-fluoroalkyl, —(C$_0$-C$_4$)-alkyl-O—(C$_1$-C$_4$)-alkyl, —(C$_0$-C$_5$)-alkyl-(C$_3$-C$_8$)-cycloalkyl, —(C$_0$-C$_2$)-alkylene-aryl, wherein aryl is as defined above and aryl is unsubstituted or substituted one, two or three times independent of each other by —(C$_1$-C$_6$)-alkyl, halogen or —(C$_3$-C$_8$)-cycloalkyl, or —(C$_0$-C$_2$)-alkylene-heterocyclyl, wherein heterocyclyl is as defined above and heterocyclyl is unsubstituted or substituted one, two or three times independent of each other by —(C$_1$-C$_6$)-alkyl, halogen or —(C$_3$-C$_8$)-cycloalkyl, R13 is hydrogen atom, —OH or —O—(C$_1$-C$_4$)-alkyl,
R16 is hydrogen atom, —OH or —O—(C$_1$-C$_4$)-alkyl, and
R23 is hydrogen atom, —OH or —O—(C$_1$-C$_4$)-alkyl,
in all its stereoisomeric forms and mixtures thereof in any ratio, and its physiologically tolerable salts.

6) Thus, the present invention also relates to compounds of the formula Ia, wherein

is a thiophenyl residue,

X is halogen,

R1 is —O—$(C_1-C_4)$-alkyl, —O—$(C_1-C_3)$-fluoroalkyl, —$(C_0-C_3)$-alkylene-$(C_1-C_3)$-fluoroalkyl or —$(C_1-C_4)$-alkyl, R2 is halogen or —$(C_0-C_4)$-alkylene-heterocyclyl, wherein heterocyclyl is selected out of the group morpholinyl, oxadiazolyl, 1,2,4-oxadiazolyl, 1,3,4-oxadiazolyl, 1,4-oxazepanyl, piperidinyl, pyrazolyl, pyridyl, pyrrolidinyl or thiazolyl, and wherein said heterocyclyl is unsubstituted or mono-, di- or trisubstituted independently of one another by R8, R3 is a hydrogen atom, halogen or —$(C_1-C_4)$-alkyl, R4 and R5 are the same or different and are independently of one another
1) hydrogen atom,
2) —$(C_1-C_4)$-alkyl, wherein alkyl is unsubstituted or mono-substituted by R7,
3) —$(C_0-C_4)$-alkylene-$(C_3-C_6)$-cycloalkyl,
provided that R4 and R5 are not each a hydrogen atom, or R4 and R5 together with the nitrogen atom to which they are bonded form a 4- to 10-membered mono- or bicyclic heterocyclic ring, which is selected from 2-oxa-5-aza-bicyclo[2.2.1]heptane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R7, R7 is halogen, =O, —$(C_0-C_3)$-alkylene-C(O)—O—R10, —C(O)—R10, —OH, —NH$_2$, =F$_2$, —O—$(C_1-C_3)$-fluoroalkyl, —$(C_0-C_3)$-alkylene-$(C_1-C_3)$-fluoroalkyl, —$(C_1-C_8)$-alkyl, wherein alkyl is unsubstituted or mono-, di- or trisubstituted independently of one another by halogen, NH$_2$, —OH or —O—$(C_1-C_6)$-alkyl,
—$(C_0-C_3)$-alkylene-$(C_3-C_8)$-cycloalkyl, —O—$(C_1-C_6)$-alkyl, wherein alkyl is unsubstituted or mono-, di- or trisubstituted independently of one another by halogen, NH$_2$, —OH or a methoxy residue, or
—$(C_0-C_3)$-alkylene-heterocyclyl, wherein heterocyclyl is selected from morpholinyl, oxadiazolyl, piperidinyl or pyrrolidinyl and is unsubstituted or mono-substituted by R10, R8 is halogen, =O or —$(C_1-C_4)$-alkyl, R10 and R20 are the same or different and are independently of one another hydrogen atom, halogen, —$(C_1-C_6)$-alkyl, or —$(C_0-C_3)$-alkyl-$(C_3-C_6)$-cycloalkyl, and R13 and R16 are each hydrogen atom, in all its stereoisomeric forms and mixtures thereof in any ratio, and its physiologically tolerable salts.

As used herein, the term alkyl is to be understood in the broadest sense to mean hydrocarbon residues which can be linear, i.e. straight-chain or branched. All these statements also apply if an alkyl group occurs as a substituent on another residue, for example in an alkyloxy residue, an alkyloxycarbonyl residue or an arylalkyl residue. Examples of "—$(C_1-C_8)$-alkyl" or "—$(C_1-C_8)$-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl. The term "—$(C_0-C_6)$-alkyl" or "—$(C_0-C_8)$-alkylene" is an alkyl residue containing 1, 2, 3, 4, 5, 6, 7 or 8 carbon atoms. The term "—$C_0$-alkyl" or "—$C_0$-alkylene" is a covalent bond.

Examples of —$(C_3-C_8)$-cycloalkyl cyclic alkyl residues are cycloalkyl residues containing 3, 4, 5, 6, 7 or 8 ring carbon atoms like cyclopropyl, cyclobutyl, cyclopentyl, cyclohexyl, cycloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom.

The term "a monocyclic or bicyclic 6- to 14-membered aryl" or "aryl" are understood as meaning aromatic hydrocarbon radicals containing from 6 to 14 carbon atoms in the ring. Examples of aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The term "-heterocyclyl" refers to a heterocycle in which one or more of the 4 to 15 ring carbon atoms are replaced by heteroatoms such as nitrogen, oxygen or sulfur. Examples are acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The term "R9 and R11 together with the carbon atom to which they are bonded form a 3- to 6 membered carbocyclic ring" refer to structures, which are selected from cyclopropyl, cyclobutyl, cyclopentyl or cyclohexyl.

The term

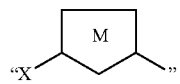

used in formulae I and Ia is a thiophenyl selected from the group

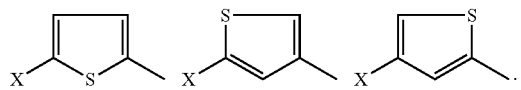

The term "R4 and R5 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen" refers to residues, which are selected from compounds such as 2-oxa-5-aza-bicyclo[2.2.1]heptane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazine, thiadiazole, thiazolidine, thiazoline, thiomorpholine, thiophene, 1,2,3-triazine, 1,2,4-triazine, 1,3,5-triazine, 1,2,3-triazole or 1,2,4-triazole.

The term "=O" refers to residues such as carbonyl (—C(O)—), sulfinyl (—S(O)—) or nitroso (—N=O).

The term "—(C$_1$-C$_3$)-fluoroalkyl" is a partial or totally fluorinated alkyl-residue, which can be derived from residues such as —CF$_3$, —CHF$_2$, —CH$_2$F, —CHF—CF$_3$, —CHF—CHF$_2$, —CHF—CH$_2$F, —CH$_2$—CF$_3$, —CH$_2$—CHF$_2$, —CH$_2$—CH$_2$F, —CF$_2$—CF$_3$, —CF$_2$—CHF$_2$, —CF$_2$—CH$_2$F, —CH$_2$—CHF—CF$_3$, —CH$_2$—CHF—CHF$_2$, —CH$_2$—CHF—CH$_2$F, —CH$_2$—CH$_2$—CF$_3$, —CH$_2$—CH$_2$—CHF$_2$, —CH$_2$—CH$_2$—CH$_2$F, —CH$_2$—CF$_2$—CF$_3$, —CH$_2$—CF$_2$—CHF$_2$, —CH$_2$—CF$_2$—CH$_2$F, —CHF—CHF—CF$_3$, —CHF—CHF—CHF$_2$, —CHF—CHF—CH$_2$F, —CHF—CH$_2$—CF$_3$, —CHF—CH$_2$—CHF$_2$, —CHF—CH$_2$—CH$_2$F, —CHF—CF$_2$—CF$_3$, —CHF—CF$_2$—CHF$_2$, —CHF—CF$_2$—CH$_2$F, —CF$_2$—CHF—CF$_3$, —CF$_2$—CHF—CHF$_2$, —CF$_2$—CHF—CH$_2$F, —CF$_2$—CH$_2$—CF$_3$, —CF$_2$—CH$_2$—CHF$_2$, —CF$_2$—CH$_2$—CH$_2$F, —CF$_2$—CF$_3$, —CF$_2$—CF$_2$—CHF$_2$ or —CF$_2$—CF$_2$—CH$_2$F.

The term "=F$_2$" is a fluoro-ethene.

Halogen is fluorine, chlorine, bromine or iodine, preferably fluorine, chlorine or bromine, particularly preferably chlorine or fluorine.

Optically active carbon atoms present in the compounds of the formulae I or Ia can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formulae I or Ia and it comprises all ratios of the stereoisomers in the mixtures. In case the compounds of the formulae I or Ia can be present as E isomers or Z isomers (or cis isomers or trans isomers) the invention relates both to pure E isomers and pure Z isomers and to E/Z mixtures in all ratios. The invention also comprises all tautomeric forms of the compounds of the formulae I or Ia.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formulae I or Ia can also be obtained by employing stereochemically uniform starting materials or by using stereoselective reactions.

Physiologically tolerable salts of the compounds of formulae I or Ia are nontoxic salts that are physiologically acceptable, in particular pharmaceutically utilizable salts. Such salts of compounds of the formula I or Ia containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formulae I or Ia, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formulae I or Ia, which simultaneously contain a basic group and an acidic group, for example a guanidino group and a carboxyl group, can also be present as zwitterions (betaines), which are likewise included in the present invention.

Salts of compounds of the formulae I or Ia can be obtained by customary methods known to those skilled in the art, for example by combining a compound of the formulae I or Ia with an inorganic or organic acid or base in a solvent or dispersant, or from other salts by cation exchange or anion exchange. The present invention also includes all salts of the compounds of the formulae I or Ia which, because of low physiologically tolerability, are not directly suitable for use in pharmaceuticals but are suitable, for example, as intermediates for carrying out further chemical modifications of the compounds of the formulae I or Ia or as starting materials for the preparation of physiologically tolerable salts.

The present invention furthermore includes all solvates of compounds of the formulae I or Ia for example hydrates or adducts with alcohols.

The invention also includes derivatives and modifications of the compounds of the formula I, for example prodrugs, protected forms and other physiologically tolerable derivatives, as well as active metabolites of the compounds of the formulae I or Ia. The invention relates in particular to prodrugs and protected forms of the compounds of the formulae I or Ia, which can be converted into compounds of the formulae I or Ia under physiological conditions. Suitable prodrugs for the compounds of the formulae I or Ia, i.e. chemically modified derivatives of the compounds of the formulae I or Ia having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443 which are all incorporated herein by reference. Suitable prodrugs for the compounds of the formulae I or Ia are especially acyl prodrugs and carbamate prodrugs of acylatable nitrogen-containing groups such as amino groups and the guanidino group and also ester prodrugs and amide prodrugs of carboxylic acid groups which may be present in compounds of the formulae I or Ia. In the acyl prodrugs and carbamate prodrugs one or more, for example one or two, hydrogen atoms on nitrogen atoms in such groups are replaced with an acyl group or a carbamate, preferably a —($C_1$-$C_6$)-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, ($C_1$-$C_{18}$)-alkyl, ($C_3$-$C_8$)-cycloalkyl, ($C_3$-$C_8$)-cycloalkyl-($C_1$-$C_4$)-alkyl-, ($C_6$-$C_{14}$)-aryl, Heterocyclyl-, ($C_6$-$C_{14}$)-aryl-($C_1$-$C_4$)-alkyl- or Heterocyclyl-($C_1$-$C_4$)-alkyl- and in which $R^{p2}$ has the meanings indicated for $R^{p1}$ with the exception of hydrogen.

The compounds of the formulae I or Ia can be prepared by utilizing procedures and techniques, which per se are well known and appreciated by one of ordinary skill in the art. Starting materials or building blocks for use in the general synthetic procedures that can be applied in the preparation of the compounds of formulae I or Ia are readily available to one of ordinary skill in the art. In many cases they are commercially available or have been described in the literature. Otherwise they can be prepared from readily available precursor compounds analogously to procedures described in the literature, or by procedures or analogously to procedures described in this application.

In general, compounds of the formulae I or Ia can be prepared, for example in the course of a convergent synthesis, by linking two or more fragments which can be derived retrosynthetically from the formula I and Ia.

The present invention also relates to processes of preparation by which the compounds of the formula I and Ia are obtainable.

In the preparation of the compounds of the formula I and Ia it can generally be advantageous or necessary in the course of the synthesis to protect functional groups, which could lead to undesired reactions or side reactions in a synthesis step. Protecting groups (or blocking groups) that may be present on functional groups include allyl, tert.-butyl, benzyl, allyloxycarbonyl (Alloc), tert-butoxycarbonyl (Boc), benzyloxycarbonyl (Z) and 9-fluorenylmethoxycarbonyl (Fmoc) as protecting groups for amino and amidino groups. Ester, alkyl, aryl and silyl protecting groups may be used to block hydroxyl groups. Carboxylic acids may be protected as esters for example methyl, ethyl and benzyl.

In particular, in the preparation of the compounds of the formula I and Ia building blocks can be connected by performing one or more condensation reactions and/or addition reactions such as amide couplings, e.g. by forming an amide bond between a carboxylic acid group of one building block and an amino group of another building block or sulfonamide couplings, e.g. by forming a sulfonamide bond between a sulfonyl chloride group of one building block and an amino group of another building block. For example, compounds of the formula I and Ia can be prepared retro-synthetically by coupling of building blocks of the formulae II, III, IV to suitable protected central core V.

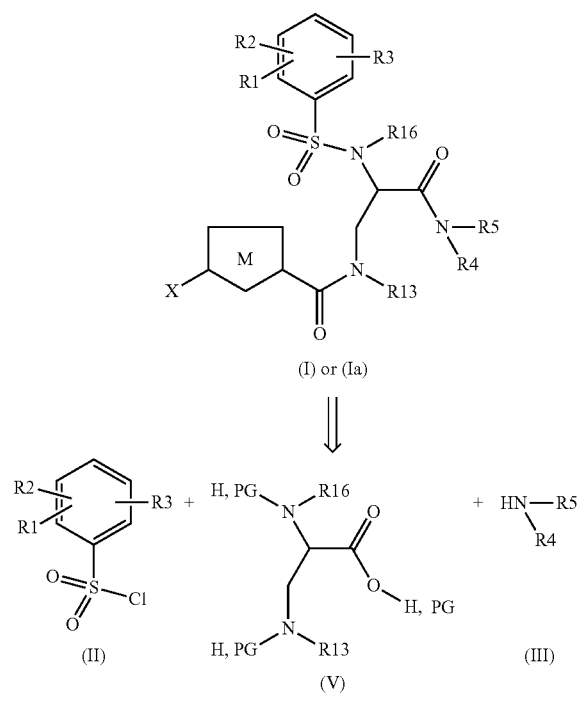

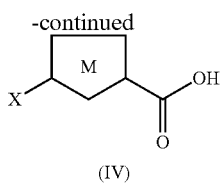

(IV)

These reactions can be carried out in any order depending on the protecting groups employed.

Various general methods for the formation of an amide bond that can be employed in the synthesis of the compounds of formula I and Ia are just so well known to those skilled in the art, for example from peptide chemistry. An amide coupling step can favorably be carried out by employing a free carboxylic acid, e.g. a compound of the formula IV, activating that carboxylic acid group, preferably in situ, by means of a customary coupling reagent such as a carbodiimide like dicyclohexylcarbodiimide (DCC) or diisopropylcarbodiimide (DIC), or an N,N'-carbonyldiazole like N,N'-carbonyldiimidazole, or a uronium salt like O-((cyano(ethoxycarbonyl)methylene)amino)-1,1,3,3-tetramethyluronium tetrafluoroborate (TOTU) or O-(7-azabenzotriazol-1-yl)-1,1,3,3-tetramethyluronium hexafluorophosphate (HATU), or a chloroformic acid ester like ethyl chloroformate or isobutyl chloroformate, or tosyl chloride, or propylphosphonic acid anhydride, or others, and then reacting the activated carboxylic acid derivative with an amino compound of the formula V. An amide bond can also be formed by reacting an amino compound with a carboxylic acid halide, in particular a carboxylic acid chloride, which can be prepared in a separate step or in situ from a carboxylic acid and, for example, thionyl chloride, or an carboxylic acid ester or thioester, for example a methyl ester, ethyl ester, phenyl ester, nitrophenyl ester, pentafluorophenyl ester, methylthio ester, phenylthio ester or pyridin-2-ylthio ester, i.e. with a compound of the formula IV.

The activation reactions and coupling reactions are usually performed in the presence of an inert solvent (or diluent), for example in the presence of an aprotic solvent like dimethylformamide (DMF), tetrahydrofuran (THF), dichloromethane (DCM), dimethyl-sulfoxide (DMSO), hexamethyl phosphoric triamide (HMPT), 1,2-dimethoxyethane (DME), dioxane, or others, or in a mixture of such solvents. Depending on the specific process, the reaction temperature may be varied over a wide range and be, for example, from about −20° C. to the boiling temperature of the solvent or diluent. Also depending on the specific process, it may be necessary or advantageous to add in a suitable amount of one or more auxiliary agents, for example a base like a tertiary amine, such as triethylamine or diisopropylethylamine, or an alkali metal alcoholate, such as sodium methoxide or potassium tert-butoxide, for adjusting the pH or neutralizing an acid that is formed or for liberating the free base of an amino compound that is employed in the form of an acid addition salt, or an N-hydroxyazole like 1-hydroxybenzotriazole, or a catalyst like 4-dimethylaminopyridine. Details on methods for the preparation of activated carboxylic acid derivatives and the formation of amide bonds and ester bonds as well as source literature are given in various standard references like, for example, J. March, Advanced Organic Chemistry, 4th ed., John Wiley & Sons, 1992.

Protecting groups (PG) that may still be present in the products obtained in the coupling reaction are then removed by standard procedures. For example, tert-butyl protecting groups, in particular a tert-butoxycarbonyl group which is used for protection of an amino group, can be deprotected, i.e. converted into the amino group, by treatment with strong acids (e.g. hydrochloric acid, trifluoroacetic acid). Methyl esters which are used for protection of an acid group may be converted into the free acid by treatment with strong bases (e.g. LiOH, NaOH, KOH) or strong acids (e.g. HCl) in the presence of water. As already explained, after the coupling reaction also functional groups can be generated from suitable precursor groups. In addition, a conversion into a physiologically tolerable salt can then be carried out by known processes.

In general, a reaction mixture containing a final compound of the formula I or Ia or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

The compounds of the formula I and Ia, which on account of their chemical structure occur in enantiomeric or diastereomeric forms, can be prepared in enantiomeric pure form employing enantiomerically pure starting material or can be resolved into the pure enantiomers by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups.

The compounds of the formula I and Ia can be isolated either in free form or, in the case of the presence of acidic or basic groups, converted into physiologically tolerable salts.

The preparation of physiologically tolerable salts of compounds of the formula I and Ia capable of salt formation, including their stereoisomeric forms, is carried out in a manner known per se. With basic reagents such as hydroxides, carbonates, hydrogen carbonates, alkoxides and also ammonia or organic bases, for example trimethyl- or triethylamine, ethanolamine or triethanolamine or alternatively basic amino acids, for example lysine, ornithine or arginine, the carboxylic acids form stable alkali metal, alkaline earth metal or optionally substituted ammonium salts. If the compounds of the formula I and Ia contain basic groups, stable acid addition salts can be prepared using strong acids e.g. both inorganic and organic acids such as hydrochloric, hydrobromic, sulfuric, phosphoric, methanesulfonic, benzenesulfonic, p-toluenesulfonic, 4-bromo-benzenesulfonic, cyclohexylamidosulfonic, trifluoromethyl-sulfonic, acetic, oxalic, tartaric, succinic or trifluoroacetic acid are suitable.

Compounds I and Ia of this application may especially be prepared by coupling of an acid IV or activated version thereof (active ester, acid halide) to 3-amino-2-tert-butoxycarbonylamino-propionic acid VI or 3-amino-2-tert-butoxycarbonylamino-propionic acid methyl ester VIa (scheme 1) leading to intermediates of formula VII and VIIa.

The starting compounds of the formulae IV and VI or VIa and other compounds which are employed in the synthesis of the compounds of formula I and Ia for introducing certain structural units, are commercially available or can be readily prepared from commercially available compounds or by analogous procedures described below or in the literature which is readily available to those skilled in the art.

Scheme 1.

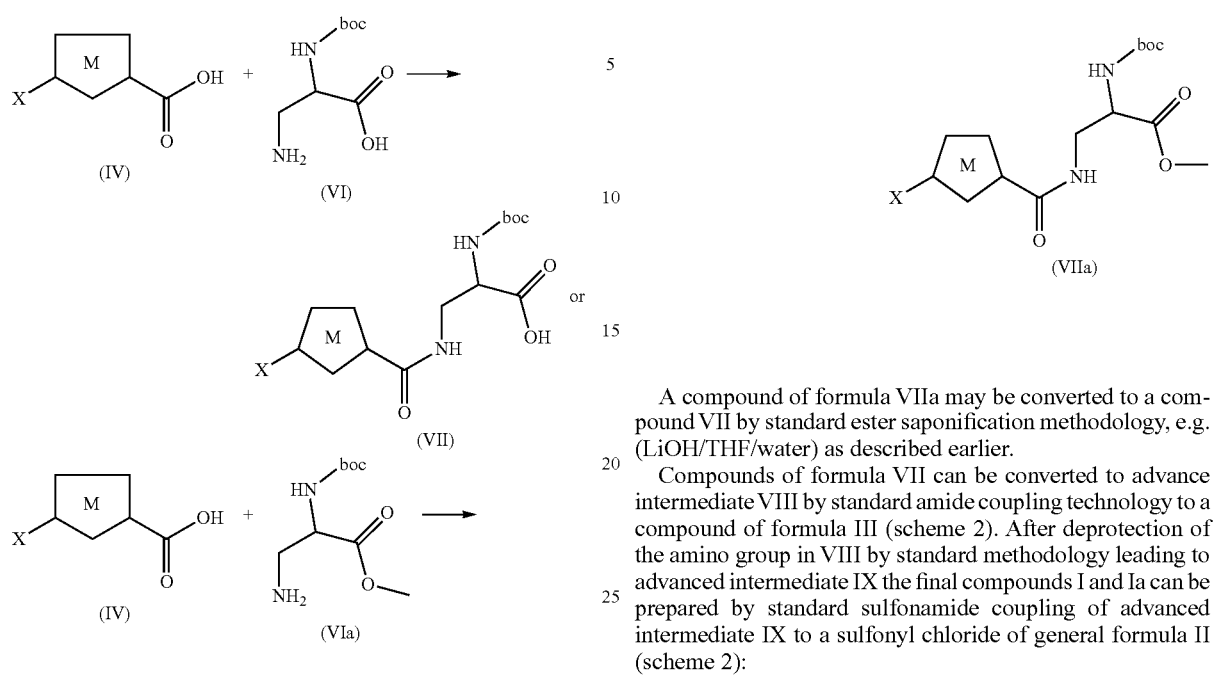

A compound of formula VIIa may be converted to a compound VII by standard ester saponification methodology, e.g. (LiOH/THF/water) as described earlier.

Compounds of formula VII can be converted to advance intermediate VIII by standard amide coupling technology to a compound of formula III (scheme 2). After deprotection of the amino group in VIII by standard methodology leading to advanced intermediate IX the final compounds I and Ia can be prepared by standard sulfonamide coupling of advanced intermediate IX to a sulfonyl chloride of general formula II (scheme 2):

Scheme 2:

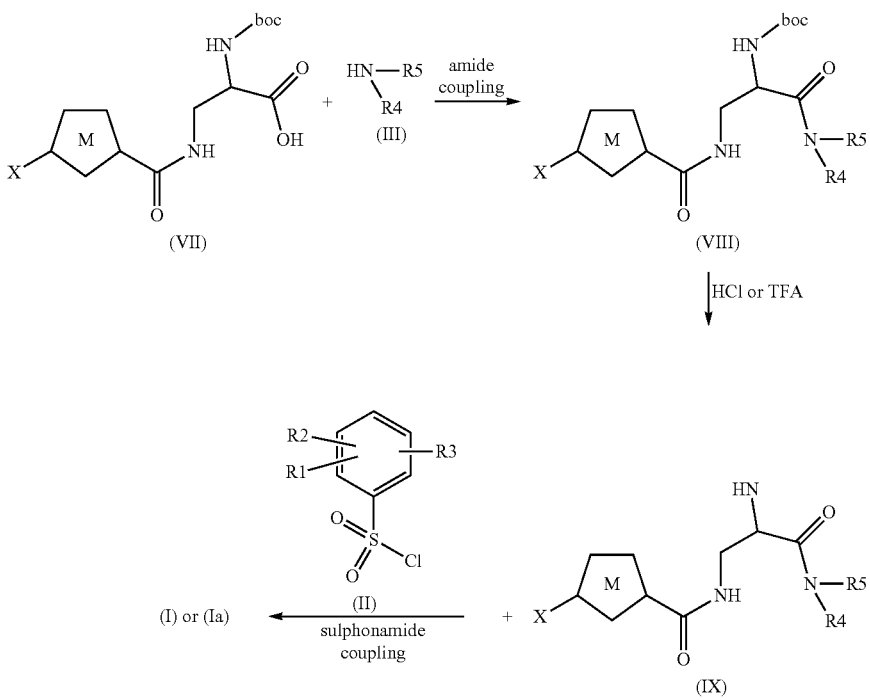

Alternatively compounds of formula VIIa can be deprotected leading to advanced intermediate X and then be converted by means of a sulfonamide coupling employing a sulfonyl chloride of formula II to advanced intermediate XI. The ester moiety present in compounds of formula XI may then be saponified under standard conditions and the resulting acid be coupled to an amine of general formula III as depicted in scheme 3 leading to final compounds I and Ia.

Scheme 3:

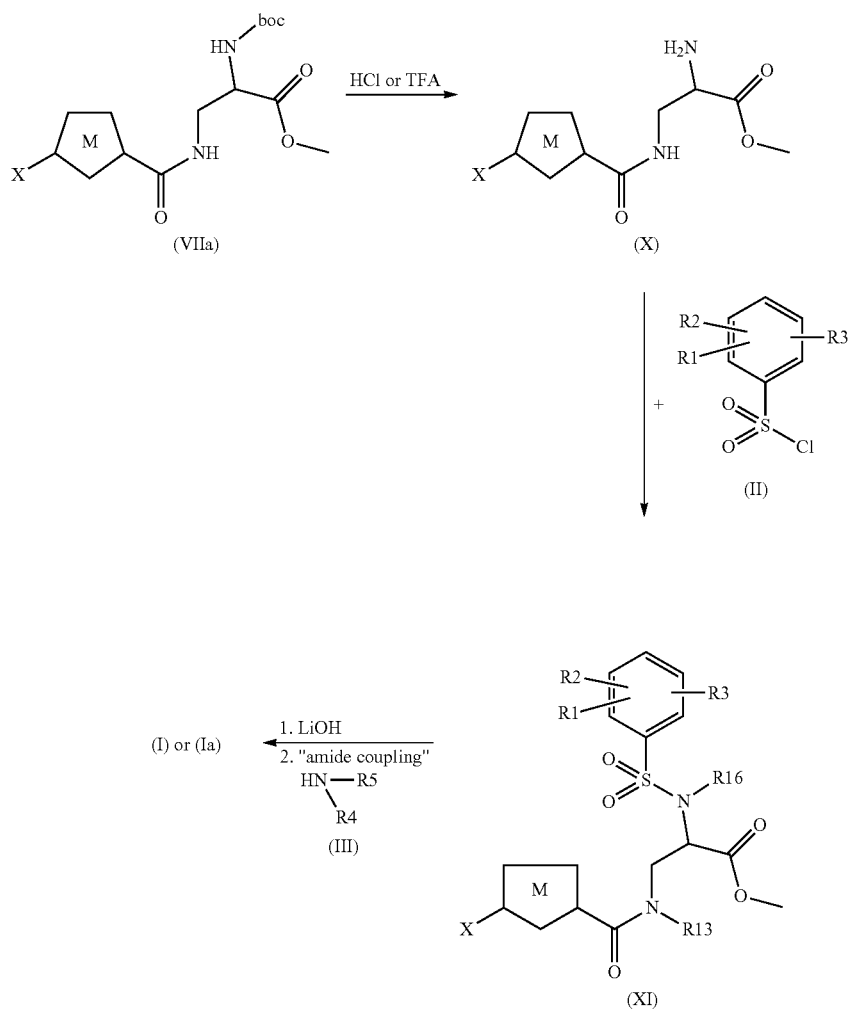

Compounds of formula II are either commercially available or prepared according to the procedures given in the schemes and examples below.

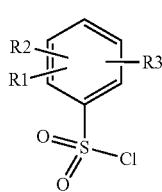
(II)

In general, functionalized sulfonyl chlorides of formula II can be prepared by many routes described in the literature. For example aryl lithium derivatives can be treated with SO$_2$ and the resulting sulfinates can be chlorinated with N-chlorosuccinimide. Another example for a suitable precursor for the sulfonyl chloride of formula II can be the corresponding sulfides XII which are commercially available or prepared according to the procedures given in the schemes and examples below. Such sulfides XII can be transformed to the corresponding sulfonyl chlorides of formula II by means of an oxidative chlorination procedure employing for example chlorine, N-chlorosuccinimide or SO$_2$Cl$_2$/acetic acid as illustrated in scheme 4:

Scheme 4:

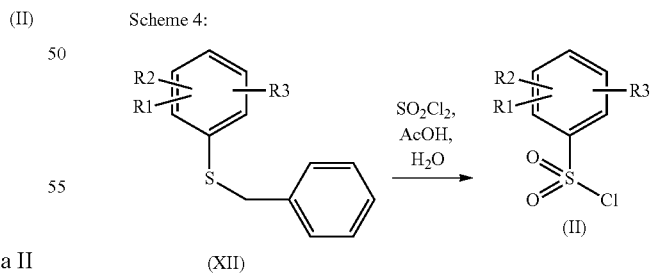

Sulfides of formula XII may generally be prepared by transition metal catalyzed transformation of aryl halides with the corresponding thiols or by nucleophilic aromatic substitution of aryl fluorides or by metal-lithium exchange of aryl halides and subsequent trapping of the lithiated species with sulfur and a suitable benzylation reagent like benzylbromide (scheme 5):

Scheme 5:

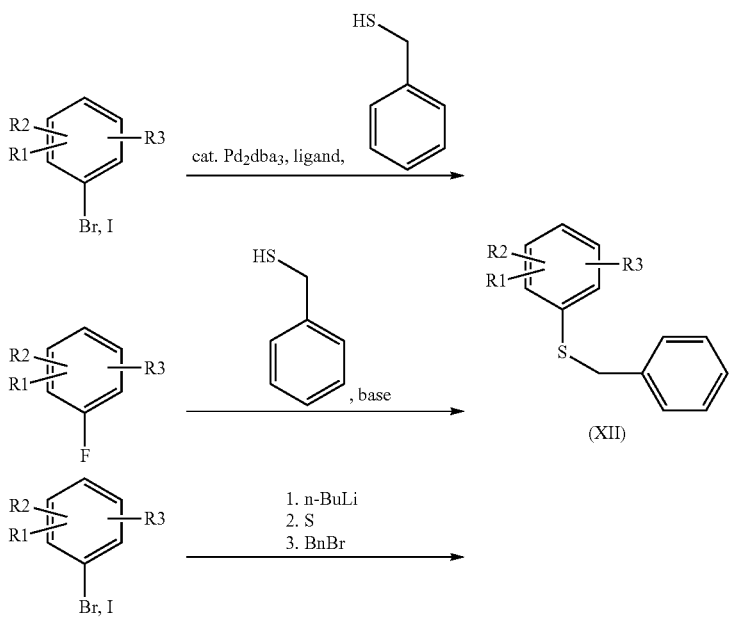

In the following, procedures of particular interest for the embodiment of this invention are listed and referenced briefly, however, they are standard procedures fully discussed in the literature, and are well known to one skilled in the art. Although not always shown explicitly, in certain cases isomers will occur during the synthesis of the below mentioned reactions. Nevertheless such mixtures of isomers can be separated by modern separation techniques like, for example, preparative HPLC.

1) Functionalization of Aryl Rings by Deprotonation and Subsequent Trapping with Electrophiles:

For example, activated aryl rings systems like 1,3-dibromobenzene may be deprotonated using strong bases like LDA and subsequently trapped with electrophiles like alkyl halides or formylating agents like DMF (scheme 6):

Scheme 6:

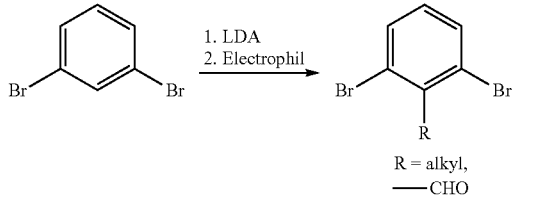

2) Functionalization of Aryl Rings by Transition Metal Catalyzed Reactions:

Modern cross coupling technology as widely described in numerous reviews (see references below) allows for selective functionalization of aryl ring systems by means of cross couplings employing suitable coupling partners.

For example a Suzuki-coupling may be carried out using and aryl halide or triflate and a boronic-acid coupling partner (scheme 7). Alternatively, these types of couplings may for example also be performed by using an aryl halide and an organo tin or an organo zinc coupling partner by means of a Stille or Negishi-coupling respectively (scheme 7):

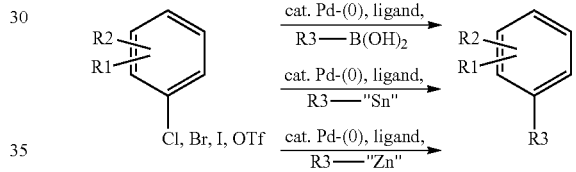

It is well understood by one skilled in the art that these couplings may be carried out in an inverted fashion of coupling partners, for example by exchanging the functionalities of the corresponding coupling partners (scheme 8):

Scheme 8:

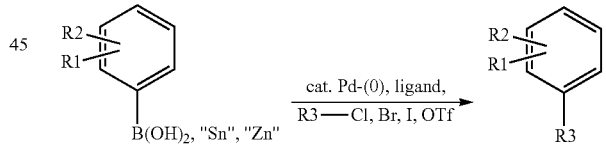

In another example aryl halides may be converted to amines or amides by transition metal catalyzed reactions. Scheme 9 illustrates the case of aryl halides being converted to amines or amides employing copper or palladium-catalyzed reactions.

Scheme 9:

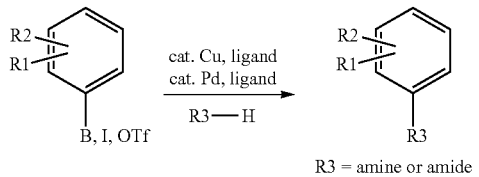

References for transition-metal catalyzed chemistry: (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. (1998) 110, 2154; B. Yang, S. Buchwald, J. Organomet. Chem. (1999) 576, 125; T. Sakamoto, K. Ohsawa, J. Chem. Soc. Perkin Trans I (1999) 2323; D. Nichols, S. Frescas, D. Marona-Lewicka, X. Huang, B. Roth, G. Gudelsky, J. Nash, J. Med. Chem. (1994) 37, 4347; P. Lam, C. Clark, S. Saubern, J. Adams, M. Winters, D. Chan, A. Combs, Tetrahedron Lett. (1998) 39, 2941; D. Chan, K. Monaco, R. Wang, M. Winters, Tetrahedron Lett. (1998) 39, 2933; V. Farina, V. Krishnamurthy, W. Scott, The Stille Reaction, Wiley, 1994; F. Qing et al. J. Chem. Soc. Perkin Trans. I (1997) 3053; S. Buchwald et al. J. Am. Chem. Soc. (2001) 123, 7727; S. Kang et al. Synlett (2002) 3, 427; S. Buchwald et al. Organic Lett. (2002) 4, 581; T. Fuchikami et al. Tetrahedron Lett. (1991) 32, 91; Q. Chen et al. Tetrahedron Lett. (1991) 32, 7689).

3) Synthesis of Ethers:

For example phenolic —OH groups may be converted to ethers by treatment with suitable electrophiles in the presence of a base. O-alkyl ether may be prepared by using an alkyl halide in the presence of a base. Alternatively, ethers may be prepared from phenols and alcohols using $PPh_3$/DIAD by means of a Mitsunobu reaction. Scheme 10 shows representative procedures:

Scheme 10:

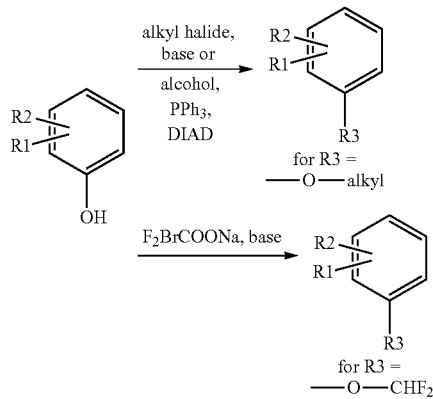

4) Nitro Reduction:

For example, nitro groups can be reduced to amino groups by means of various reducing agents, such as sulfides, dithionites, complex hydrides or by catalytic hydrogenation.

5) Ester-Saponification:

Ester groups present can be hydrolyzed to the corresponding carboxylic acids, which after activation can then be reacted with amines or alcohols under standard conditions to give amides or esters, respectively.

General:

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany) in which details on the reactions and primary source literature can be found. In the present case it may in certain cases become necessary to specifically adapt reaction conditions or to choose specific reagents from a variety of reagents that can in principle be employed in a conversion reaction, or otherwise to take specific measures for achieving a desired conversion, for example to use protecting group techniques. However, finding out suitable reaction variants and reaction conditions in such cases does not cause any problems for one skilled in the art.

Protecting Groups:

See, for example, Greene and Wuts, Protective Groups in Organic Synthesis, Wiley, 1991, or P. Kocienski, Protecting Groups, Thieme 1994).

Amide-Couplings:

N-Acylation of a nitrogen atom, for example with substituted thiophene carboxylic acid derivatives to produce finally compounds of the formulae I or Ia, can, for example, be performed under standard conditions by means of common coupling reagents used in peptide synthesis. Such coupling reagents are, for example, carbodiimides like dicyclohexylcarbodiimide (DCC) or diisopropylcarbodiimide, carbonyldiazoles like carbonyldiimidazole (CDI) and similar reagents, propylphosphonic anhydride, O-((cyano-(ethoxycarbonyl)-methylene)amino)-N,N,N',N'-tetramethyluronium tetrafluoroborate (TOTU), O-(7-aza-benzotriazole-1-yl)-N,N,N',N'-tetramethyluronium-hexafluorophosphate (HATU), diethylphosphoryl cyanide (DEPC) or bis-(2-oxo-3-oxazolidinyl)-phosphoryl chloride (BOP-Cl) and many others. N-Acylation can also be performed by the reaction with a corresponding acid-chloride, -fluoride or -bromide or a corresponding anhydride.

The compounds of the present invention are serine protease inhibitors, which inhibit the activity of the blood coagulation enzymes factor Xa and thrombin. They are specific serine protease inhibitors inasmuch as they do not substantially inhibit the activity of other proteases whose inhibition is not desired. The activity of the compounds of the formulae I or Ia can be determined, for example, in the assays described below or in other assays known to those skilled in the art. With respect to factor Xa and thrombin inhibition, a preferred embodiment of the invention comprises compounds which have a Ki<1 mM for factor Xa inhibition and thrombin inhibition as determined in the assays described below and which preferably do not substantially inhibit the activity of other proteases involved in coagulation and fibrinolysis whose inhibition is not desired (using the same concentration of the inhibitor). The compounds of the invention inhibit factor Xa catalytic activity either directly, or additionally within the prothrombinase complex, as a soluble subunit, or indirectly, by inhibiting the assembly of factor Xa into the prothrombinase complex, and directly by inhibiting the catalytic activity of thrombin. Moreover a dual Xa/Thrombin inhibitor could play a pivotal role on the inhibition of thrombin formation due to its anti-Xa activity and on the inhibition of traces of thrombin due to its anti-thrombin activity and through the prevention of activation of Protease Activated Receptors (PARs) present on the vascular wall and platelets.

As inhibitors of factor Xa and thrombin the compounds of the formulae I or Ia and their physiologically tolerable salts and their prodrugs are generally suitable for the therapy and prophylaxis of conditions in which the activity of factor Xa and/or thrombin plays a role or has an undesired extent, or which can favorably be influenced by inhibiting factor Xa and thrombin or decreasing their activities, or for the prevention, alleviation or cure of which an inhibition of factor Xa and thrombin or a decrease in their activity is desired by the physician. As inhibition of factor Xa and thrombin influences blood coagulation and fibrinolysis, the compounds of the formulae I or Ia and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus are the reduction or inhibition of unwanted blood clotting, in particular in an individual, by administering an effective amount of a compound of the formula I or a physiologically tolerable salt or a prodrug thereof, as well as pharmaceutical preparations therefore.

The present invention also relates to the use of the compounds of the formulae I or Ia and/or their physiologically tolerable salts and/or their prodrugs for the production of pharmaceuticals for inhibition of factor Xa and thrombin or for influencing blood coagulation, inflammatory response or fibrinolysis or for the therapy or prophylaxis of the diseases mentioned above or below, for example for the production of pharmaceuticals for the therapy and prophylaxis of cardiovascular disorders, thromboembolic diseases or restenoses. The invention also relates to the use of the compounds of the formulae I or Ia and/or their physiologically tolerable salts and/or their prodrugs for the inhibition of factor Xa and thrombin or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formulae I or Ia and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the present invention can also be used to reduce an inflammatory response. Examples of specific disorders for the treatment or prophylaxis of which the compounds of the formulae I or Ia can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

For these diseases, the compounds of the formulae I or Ia and their physiologically tolerable salts and their prodrugs could be used in association with other marketed antiplatelet or anticoagulant agents, e.g. enoxaparin Natrium, acetylsalicylic acid or clopidogrel.

The compounds of the formulae I or Ia and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formulae I or Ia and/or its (their) physiologically tolerable salts and/or its (their) prodrugs. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formulae I or Ia and/or their physiologically tolerable salts and/or their prodrugs. The amount of the active ingredient of the formulae I or Ia and/or its physiologically tolerable salts and/or its prodrugs in the pharmaceutical preparations normally is from about 0.5 mg to about 1000 mg, preferably from about 1 mg to about 500 mg.

In addition to the active ingredients of the formulae I or Ia and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formulae I or Ia, and/or their physiologically tolerable salts and/or their prodrugs. In case a pharmaceutical preparation contains two or more compounds of the formulae I or Ia, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formulae I or Ia allows a great deal of control over the biological and physico-chemical properties of the compounds and thus allows the selection of such desired compounds. Furthermore, in addition to at least one compound of the formulae I or Ia and/or a physiologically tolerable salt and/or its prodrug, the pharmaceutical preparations can also contain one or more other therapeutically or prophylactically active ingredients.

When using the compounds of the formulae I or Ia the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formulae I or Ia can also advantageously be used as an anticoagulant outside an individual. For example, an effective amount of a compound of the invention can be contacted with a freshly drawn blood sample to prevent coagulation of the blood sample. Further, a compound of the formulae I or Ia or its salts can be used for diagnostic purposes, for example in in vitro diagnoses, and as an auxiliary in biochemical investigations. For example, a compound of the formulae I or Ia can be used in an assay to identify the presence of factor Xa or thrombin or to isolate factor Xa or thrombin in a substantially purified form. A compound of the invention can be labeled with, for example, a radioisotope, and the labeled compound bound to factor Xa or thrombin is then detected using a routine method useful for detecting the particular label. Thus, a compound of the formulae I or Ia or a salt thereof can be used as a probe to detect the location or amount of factor Xa and thrombin activity in vivo, in vitro or ex vivo.

Furthermore, the compounds of the formulae I or Ia can be used as synthesis intermediates for the preparation of other compounds, in particular of other pharmaceutical active ingredients, which are obtainable from the compounds of the formulae I or Ia, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention. When in the final step of the synthesis of a compound an acid such as trifluoroacetic acid or hydrochloric acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the trifluoroacetic acid salt or hydrochloric acid salt.

Further, the compounds of the formula I can be used as synthesis intermediates for the preparation of other compounds, in particular of other pharmaceutical active ingredients, which are obtainable from the compounds of the formula I, for example by introduction of substituents or modification of functional groups.

It is understood that modifications that do not substantially affect the activity of the various embodiments of this invention are included within the invention disclosed herein. Accordingly, the following examples are intended to illustrate but not limit the present invention.

Abbreviations Used:
acetic acid AcOH
acetonitrile AcN
aqueous aq
(Bis-(2-methoxyethyl-)amino-)sulfur trifluoride BAST
n-Butyllithium n-BuLi
tert-Butyl tBu
2,2'-bis(diphenylphoshino-1,1'-binaphthyl Binap
Bis-(oxo-3-oxazolidinyl)-phosphoryl chloride BOP-Cl
concentrated conc.
dibenzylidenacetone dba
Dichloromethane DCM
Dicyclohexyl-carbodiimide DCC
Diethylphosphoryl cyanide DEPC
Diisopropylethylamine DIPEA
4-Dimethyaminopyridine DMAP
N,N-Dimethylformamide DMF
Dimethylsulfoxide DMSO
1,1'-Bis(diphenylphosphino)ferrocene DPPF
O-(7-Azabenzotriazol-1-yl)-N,N,N',N'-tetramethyluronium-hexafluorophosphate HATU
Lithium diisopropylamide LDA
Methanol MeOH
Tert.-butyl methyl ether MTBE
N-Bromosuccinimide NBS
N-Chlorosuccinimide NCS
N-Iodosuccinimide NIS
N-Ethylmorpholine NEM
Room temperature 20° C. to 25° C. RT
Saturated sat.
O-(Benzotriazol-1-yl)-N,N,N',N'-tetramethyluronium tetrafluoroborate TBTU
Triethylamine TEA
Tetrahydrofuran THF
Trifluoroacetic acid TFA
O-((Ethoxycarbonyl)cyanomethyleneamino)-N,N,N',N'-tetramethyluronium tetrafluoroborate TOTU
9,9-dimethyl-4,5-bis(diphenylphosphino)xanthene Xantphos Example 1

5-Chloro-thiophene-2-carboxylic acid [(S)-2-[2-ethyl-3-(3-oxo-morpholin-4-yl)-benzenesulfonylamino]-3-((S)-3-methyl-morpholin-4-yl)-3-oxo-propyl]-amide 1.1) (S)-2-tert-Butoxycarbonylamino-3-[(5-chloro-thiophene-2-carbonyl)-amino]-propionic acid (Intermediate 1)

Commercially available (S)-3-Amino-2-tert-butoxycarbonylamino-propionic acid (BOO-Dap-OH) (408 mg, 2 mmol)

was suspended in 4 ml DCM and DIPEA (1.75 ml, 10 mmol). 5-Chloro-thiophene-2-carbonyl chloride (362 mg, 2 mmol) (described in WO 2005068456) in 4 ml DCM was added slowly and the mixture was stirred at RT for 2 h. The reaction was filtered and the solvent evaporated. The resulting solid (895 mg) was used without further purification in the next step.

1.2) [(S)-1-{[(5-Chloro-thiophene-2-carbonyl)-amino]-methyl}-2-((S)-3-methyl-morpholin-4-yl)-2-oxo-ethyl]-carbamic acid tert-butyl ester (Intermediate 2)

Intermediate 1 from step 1.1 was dissolved in 10 ml DCM and (3S)-methyl morpholine hydrochloride (276 mg, 2 mmol) was added followed by DIPEA (1.4 ml, 8 mmol) and HATU (761 mg, 2 mmol). After 1 h stirring at RT the reaction mixture was evaporated to dryness and the product was isolated by preparative HPLC.

Yield: 306 mg, 35% (2 steps).

1.3) 5-Chloro-thiophene-2-carboxylic acid [(S)-2-amino-3-((S)-3-methyl-morpholin-4-yl)-3-oxo-propyl]-amide (Intermediate 3)

Intermediate 2 (306 mg, 0.708 mmol) from step 1.2 was dissolved in 3 ml of DCM, cooled to 0° C. and slowly treated with 1.42 ml (1.42 mmol) of a $BBr_3$-solution (1M in DCM). After 2 h at 0° C. 7 ml sat. aq $NaHCO_3$-solution and 3 ml $H_2O$ were added and the reaction was stirred for 15 min at RT. The organic layer was separated and the aqueous phase extracted with DCM. The combined organic layers were washed with $H_2O$, dried with $MgSO_4$, filtered and evaporated to dryness. 191 mg of crude product were obtained and used without further purification in step 1.8.

1.4) 1,3-Dibromo-2-ethyl-benzene (Intermediate 4)

A three necked round-bottom flask was purged with argon and then filled with dry THF (1.2 l), 1,3-dibromo benzene (121 g, 0.514 mol) and ethyl iodide (95.4 g, 0.611 mol). The mixture was cooled to −78° C. and LDA (64.2 g, 0.697 mol) (2 M in THF/n-heptane/ethylbenzene) was added slowly in a way that the temperature didn't rise above −65° C. After stirring for 2.75 h the reaction was poured onto 1 l sat. aq $NH_4Cl$ solution and stirred vigorously for 20 min. Extraction with DCM (twice) yielded a colorless oil (167 g) which was used in the next step without further purification 1.5) 1-Benzylsulfanyl-3-bromo-2-ethyl-benzene (Intermediate 5)

According to J. Org. Chem. 2004, 69, 3236-3239:
Intermediate 4 (528 mg, 2 mmol) in 13 ml THF was cooled to −78° C. and then treated with n-BuLi (1.25 ml, 2 mmol) (1.6 M in heptane). After stirring for 15 min at −78° C. sulfur (64 mg, 2 mmol) was added under an argon atmosphere and the reaction temperature was kept at −78° C. for another 30 min. Then BnBr (0.238 ml, 2 mmol) in 2 ml THF was added and stirring at −78° C. was continued for 90 min. The reaction was quenched by addition of 10 ml sat. aq $NH_4Cl$-solution and 150 ml of $H_2O$. After extraction with DCM (three times), the combined organic layers were washed with water, dried with $MgSO_4$, evaporated to dryness and the product was purified by chromatography on silica gel. Yield: 488 mg, 79

1.6) 4-(3-Benzylsulfanyl-2-ethyl-phenyl)-morpholin-3-one (Intermediate 6)

Intermediate 5 (1.075 g, 3.5 mmol), morpholin-3-one (389 mg, 3.85 mmol), CuI (67 mg, 0.35 mmol), N,N'-dimethylethylene diamine (75 µl, 0.7 mmol) and $K_2CO_3$ (1,064 g, 7.7 mmol) were suspended in toluene (30 ml) under argon and heated to 110° C. for 20 h. After cooling to RT the reaction mixture was quenched by addition of 100 ml sat. aq $NH_4Cl$, 150 ml conc. $NH_3$ in water and 100 ml water and extracted three times with ethyl acetate. The organic layers were combined and washed with water and sat. aq NaCl-solution, dried with $MgSO_4$, filtered and evaporated to dryness. The resulting oil crystallizes upon standing and was triturated with n-heptane-MTBE (19:1).

Yield: 974 mg, 85

1.7) 2-Ethyl-3-(3-oxo-morpholin-4-yl)-benzene-sulfonyl chloride (Intermediate 7)

Intermediate 6 (197 mg, 0.6 mmol) 1.6) was dissolved in 4 ml DCM and treated with water (44 µl, 2.4 mmol), AcOH (138 µl, 2.4 mmol) and $SO_2Cl_2$ (193 µl, 2.4 mmol) at 0° C. After stirring for 5 min at 0° C. and 90 min at RT the reaction was cooled back to 0° C. and quenched by addition of 10 ml water. The aqueous solution was extracted with DCM (3×) and combined organic layers were washed with cold water. Drying over $MgSO_4$ and evaporation to dryness yielded 209 mg of crude intermediate 7 which was used without further purification in the next step.

1.8) 5-Chloro-thiophene-2-carboxylic acid [(S)-2-[2-ethyl-3-(3-oxo-morpholin-4-yl)-benzenesulfonylamino]-3-((S)-3-methyl-morpholin-4-yl)-3-oxo-propyl]-amide 5-Chloro-thiophene-2-carboxylic acid [(S)-2-amino-3-((S)-3-methyl-morpholin-4-yl)-3-oxo-propyl]-amide, Intermediate 3 (95 mg, 0.287 mmol) was dissolved in 2 ml DCM and DIPEA (151 µl, 0.861 mmol). 2-ethyl-3-(3-oxo-morpholin-4-yl)-benzenesulfonyl chloride, Intermediate 7 (91 mg, 0.3 mmol) in 2 ml DCM was slowly added and the reaction was stirred for 75 min. After that the solution was evaporated to dryness and purified by prep. HPLC. After lyophilization the title compound was obtained as colorless, amorphous solid. Yield: 108 mg, 63%

MS ($ES^+$): m/e=599.1/601.0, chloro pattern.

Example 2

5-Chloro-thiophene-3-carboxylic acid [(S)-2-[2-ethyl-3-(3-oxo-morpholin-4-yl)-benzenesulfonylamino]-3-((S)-3-methyl-morpholin-4-yl)-3-oxo-propyl]-amide The title compound is prepared in analogy to the preparation steps 1.1)-1.8) in Example 1. In the first step 4-Chloro-thiophene-2-carbonyl chloride is used instead of 5-Chloro-thiophene-2-carbonyl chloride in 1.1).

62 mg prepared, colorless, amorphous solid after HPLC separation and lyophilization.

MS ($ES^+$): m/e=599.1/601.0, chloro pattern.

Example 3

5-Chloro-thiophene-2-carboxylic acid [(S)-2-[2-ethyl-3-(3-oxo-morpholin-4-yl)-benzenesulfonylamino]-3-((R)-2-methyl-morpholin-4-yl)-3-oxopropyl]-amide

3.1) (S)-2-tert-Butoxycarbonylamino-3-[(5-chloro-thiophene-2-carbonyl)-amino]-propionic acid methyl ester (Intermediate 8)

5-Chloro-thiophene-2-carboxylic acid (16.26 g, 0.1 mol) in 500 ml DCM was stirred with DIPEA (51.04 ml, 0.3 mol) and TOTU (32.8 g, 0.1 mmol) at RT for 5 min. Commercially available (S)-3-amino-2-tert-butoxycarbonylamino-propionic acid methyl ester hydrochloride (25.4 g, 0.1 mol) were added and the reaction mixture was stirred at RT overnight and then evaporated. The resulting solid was suspended in 400 ml DCM and washed subsequently with sat. aq NaHCO$_3$, 1N HCl and brine. The organic layer was dried with MgSO$_4$, filtered and evaporated. The crude material was triturated with DCM and the solid filtered off. One obtained 18.4 g white, amorphous solid which was used in the next step without further purification.

3.2) (S)-2-Amino-3-[(5-chloro-thiophene-2-carbonyl)-amino]-propionic acid methyl ester trifluoro acetate (Intermediate 9)

Intermediate 8 (13.3 g, 36.66 mmol) in 75 ml DCM was treated with 25 ml TFA and stirred overnight at RT. The solvents were evaporated and the residue was dissolved in DCM and evaporated again. Yield: 21 g (TFA-salt), oil, crude material

3.3) (S)-3-[(5-Chloro-thiophene-2-carbonyl)-amino]-2-[2-ethyl-3-(3-oxo-morpholin-4-yl)-benzenesulfonylamino]-propionic acid methyl ester (Intermediate 10)

To intermediate 9 (2.9 g, 8.25 mmol) in 80 ml DCM was added DIPEA (5.61 ml, 33 mmol) and Intermediate 7 (2.506 g, 8.25 mmol) dissolved in 60 ml DCM. The mixture was stirred at RT overnight. After evaporation the resulting solid was dissolved in ethyl acetate and washed subsequently with 1N HCl, sat. aq NaHCO$_3$, and brine. The organic layer was dried with MgSO$_4$, filtered and evaporated. The crude material was used without further purification in the next step. Yield: 3.1 g, 71%

3.4) (S)-3-[(5-Chloro-thiophene-2-carbonyl)-amino]-2-[2-ethyl-3-(3-oxo-morpholin-4-yl)-benzenesulfonylamino]-propionic acid (Intermediate 11)

To intermediate 10 (3.1 g, 5.85 mmol) in 60 ml THF, 20 ml methanol and 20 ml water was added LiOH (421 mg, 17.55 mmol) and stirring was continued for 4 h. After evaporation the residue was acidified with HCl and the acid was extracted with ethylacetate. The organic layer was dried with MgSO$_4$, filtered and evaporated.
Yield: 2.6 g, 86%, crude material

3.5) 5-Chloro-thiophene-2-carboxylic acid [(S)-2-[2-ethyl-3-(3-oxo-morpholin-4-yl)-benzenesulfonylamino]-3-((R)-2-methyl-morpholin-4-yl)-3-oxopropyl]-amide To intermediate 11 (200 mg, 0.39 mmol) in DCM/DMF 2:1 (7 ml) was added (R)-2-methyl-morpholine (described in EP 656365), HATU (162 mg, 0.43 mmol) and DIPEA (263 µl, 1.55 mmol). After stirring overnight the mixture was purified by prep. HPLC.
Yield after lyophilization: 26 mg, 11%, colorless, amorphous solid.
MS (ES$^+$): m/e=599.2/601.2, chloro pattern.

Example 4

5-Chloro-thiophene-2-carboxylic acid [(S)-2-[2-ethyl-3-(3-oxo-morpholin-4-yl)-benzenesulfonylamino]-3-((R)-3-methoxy-piperidin-1-yl)-3-oxopropyl]-amide

4.1) (R)-3-Methoxy-piperidine-1-carboxylic acid tert-butyl ester (Intermediate 12)

To commercially available (R)-3-hydroxy-piperidine-1-carboxylic acid tert-butyl ester (4.5 g, 22.36 mmol) in 60 ml DMF at 0° C. was added NaH (1.3 g, 33.54 mmol, 55-65 in mineral oil) under stirring in three portions under an argon atmosphere. After 20 min methyl iodide (4.76 g, 33.54 mmol) was added and the reaction was warmed to RT and stirred for another 3 h. After quenching with sat. aq NaHCO$_3$-solution the mixture was extracted with ethyl acetate. The organic layer was washed with 1N KHSO$_4$ and brine. The organic layer was dried with MgSO$_4$, filtered and evaporated. The crude material was purified by chromatography on silica gel.
Yield: 4.6 g, 96

4.2) (R)-3-Methoxy-piperidine trifluoro acetate (Intermediate 13)

To intermediate 12 (4.6 g, 21.37 mmol) in 10 ml DCM was added 10 ml TFA. After stirring for 1 h at RT the reaction was evaporated. Yield: ~10 g, crude material

4.3) 5-Chloro-thiophene-2-carboxylic acid [(S)-2-[2-ethyl-3-(3-oxo-morpholin-4-yl)-benzenesulfonylamino]-3-((R)-3-methoxy-piperidin-1-yl)-3-oxopropyl]-amide To intermediate 11 (250 mg, 0.48 mmol) in DCM/DMF 2:1 (6 ml) was added intermediate 13 (56 mg, 0.48 mmol), HATU (221 mg, 0.58 mmol) and DIPEA (330 µl, 1.94 mmol). After stirring for 2 h the mixture was purified by prep. HPLC. Yield after lyophilization: 200 mg, 68%, colorless, amorphous solid.
MS (ES$^+$): m/e=613.1/615.2, chloro pattern.

Example 5

5-Chloro-thiophene-2-carboxylic acid {(S)-3-azepan-1-yl-2-[2-chloro-3-(3-oxo-morpholin-4-yl)-benzenesulfonylamino]-3-oxo-propyl}-amide

5.1) ((S)-2-Azepan-1-yl-1-{[(5-chloro-thiophene-2-carbonyl)-amino]-methyl}-2-oxoethyl)-carbamic acid tert-butyl ester (Intermediate 14)

To stirred intermediate 1 (1.5 g, 4.3 mmol) in 20 ml DCM was added azepane (426 mg, 4.3 mmol), TOTU (1.692 g, 5.16 mmol) and DIPEA (1.46 ml, 8.60 mmol). After 2 h the mixture was washed subsequently with sat. aq NaHCO$_3$, and brine. The organic layer was dried with MgSO$_4$, filtered and evaporated. The crude material (2.2 g) was used without further purification in the next step.

5.2) 5-Chloro-thiophene-2-carboxylic acid ((S)-2-amino-3-azepan-1-yl-3-oxo-propyl)amide hydro chloride (Intermediate 15)

Intermediate 14 (1.848 g, 4.30 mmol) was treated with 30 ml 4N HCl in dioxane. After complete conversion the mixture was evaporated to dryness. Crude intermediate 15 was obtained (1.8 g) and used without further purification in step 5.6

5.3) 1-Benzylsulfanyl-3-bromo-2-chloro-benzene (Intermediate 16)

To stirred phenyl-methanethiol (14.8 g, 119.36 mmol) in 175 ml DMF was added Cs$_2$CO$_3$ (38.89 g, 119.36 mmol) under argon. After 10 min 1-bromo-2-chloro-3-fluoro-benzene (25 g, 119.36 mmol) in 25 ml DMF was added and stirring was continued overnight at RT and then 3 h at 80° C. After cooling the mixture was diluted with ethyl acetate/water and washed subsequently with 1 N HCl and brine. The organic layer was dried with MgSO$_4$, filtered and evaporated. Purification by chromatography on silica gel yielded 22 g (59%) as an amorphous, colorless solid.

5.4) 4-(3-Benzylsulfanyl-2-chloro-phenyl)-morpholin-3-one (Intermediate 17)

Intermediate 16 (10 g, 31.38 mmol) was treated with morpholin-3-one (389 mg, 3.85 mmol) according to the procedure described in 1.6).
Yield after chromatography on silica gel (n-heptane-ethyl acetate): 7.2 g (68%).

5.5) 2-Chloro-3-(3-oxo-morpholin-4-yl)-benzenesulfonyl chloride (Intermediate 18)

Intermediate 17 (1 g, 3.05 mmol) was converted to the title sulfonyl chloride using the procedure described in 1.7). The crude material was used without further purification in the next step.

5.6) 5-Chloro-thiophene-2-carboxylic acid {(S)-3-azepan-1-yl-2-[2-chloro-3-(3-oxo-morpholin-4-yl) benzenesulfonylamino]-3-oxo-propyl}-amide Intermediate 14 (319 mg, 0.97 mmol) and intermediate 18 (300 mg, 0.97 mmol) were coupled using the procedure described in 1.8). The mixture was purified by prep.
HPLC. Yield after lyophilization: 192 mg, 33%, colorless, amorphous solid.
MS (ES$^+$): m/e=603.1/605.2, chloro pattern.

Example 6

5-Chloro-thiophene-2-carboxylic acid {(S)-3-azepan-1-yl-2-[5-fluoro-2-methoxy-3-(3-oxo-morpholin-4-yl)-benzenesulfonylamino]-3-oxo-propyl}-amide

6.1) 1-Benzylsulfanyl-3-bromo-5-fluoro-2-methoxy-benzene (Intermediate 19)

1,3-Dibromo-5-fluoro-2-methoxy-benzene (14.2 g, 50 mmol), phenyl-methanethiol (5.86 ml, 50 mmol), Pd$_2$dba$_3$ (1.145 g, 1.25 mmol, 2.5 mol-%), Xantphos (1.447 g, 2.5 mmol, 5 mol-%) and DIPEA (17.5 ml, 100 mmol) were dissolved in 130 ml dry, degassed 1,4-dioxane and heated to reflux for 3 h. After cooling down the mixture was filtrated and evaporated. The remaining solid (22 g) is chromatographed on silica gel using n-heptane-MTBE as eluent. Yield: 12.42 g, 76%.

6.2) 4-(3-Benzylsulfanyl-5-fluoro-2-methoxy-phenyl)-morpholin-3-one (Intermediate 20)

Intermediate 19 (8.18 g, 25 mmol) was converted in close analogy to the procedure described in 1.6) to intermediate 20. Yield: 5.31 g, 61%.

6.3) 5-Fluoro-2-methoxy-3-(3-oxo-morpholin-4-yl)-benzenesulfonyl chloride (Intermediate 21)

Intermediate 20 (1.83 g, 5.25 mmol) was converted in close analogy to the procedure described in 1.7) to intermediate 21. The crude product was used without further purification in the next step.

6.4) (S)-3-[(5-Chloro-thiophene-2-carbonyl)-amino]-2-[5-fluoro-2-methoxy-3-(3-oxo-morpholin-4-yl)-benzenesulfonylamino]-propionic acid methyl ester (Intermediate 22)

Intermediate 21 (1.70 g, 5.25 mmol) and intermediate 9 (1.88 g, 5.00 mmol) were converted in close analogy to the procedure described in 3.3) to intermediate 22. The crude product was used without further purification in the next step.

6.5) (S)-3-[(5-Chloro-thiophene-2-carbonyl)-amino]-2-[5-fluoro-2-methoxy-3-(3-oxo-morpholin-4-yl)-benzenesulfonylamino]-propionic acid (Intermediate 23)

Intermediate 22 (0.99 g, 1.8 mmol) was converted in close analogy to the procedure described in 3.4) to intermediate 23. The crude product was used without further purification in the next step.

6.6) 5-Chloro-thiophene-2-carboxylic acid {(S)-3-azepan-1-yl-2-[5-fluoro-2-methoxy-3-(3-oxo-morpholin-4-yl)-benzenesulfonylamino]-3-oxo-propyl}-amide Intermediate 23 (225 mg, 0.42 mmol) and azepane (57 µl, 0.462 mmol) were coupled in close analogy to the procedure described in 3.5) using DMF as solvent. The mixture was purified by prep. HPLC. Yield after lyophilization: 199 mg, 77%, colorless, amorphous solid. MS (ES$^+$): m/e=617.1/619.1, chloro pattern.

Example 7

5-Chloro-thiophene-2-carboxylic acid {(S)-3-(4-cyclopropyl-piperazin-1-yl)-3-oxo-2-[3-(2-oxo-piperidin-1-yl)-2-trifluoromethyl-benzenesulfonylamino]propyl}amide trifluoroacetate

7.1) 1-Benzylsulfanyl-3-bromo-2-trifluoromethyl-benzene (Intermediate 24)

Phenyl-methanethiol (4.g g, 37.0 mmol) was treated with commercially available 1-bromo-3-fluoro-2-trifluoromethyl-benzene (10.0 g, 41.1 mmol) in close analogy to the procedure described in step 5.3). The crude product (10.5 g) after workup was used as such in the next reaction step without purification by chromatography.

7.2) 1-(3-Benzylsulfanyl-2-trifluoromethyl-phenyl) piperidin-2-one (Intermediate 25)

Intermediate 24 (10.5 g, 30.24 mmol) was coupled with piperidin-2-one (3.597 g, 36.29 mmol) in close analogy to the procedure described in step 1.6). After workup the crude oil is purified by chromatography on silica gel (n-heptane-ethyl acetate 4:1).

Yield: 2.4 g, 16% (2 steps)

7.3) 3-(2-Oxo-piperidin-1-yl)-2-trifluoromethyl-benzenesulfonyl chloride (Intermediate 26)

Intermediate 25 (2.3 g, 6.3 mmol) was converted in close analogy to the procedure described in 1.7) to intermediate 26. The crude product was used without further purification in the next step.

7.4) (S)-3-[(5-Chloro-thiophene-2-carbonyl)-amino]-2-[3-(2-oxo-piperidin-1-yl)-2-trifluoromethyl-benzenesulfonylamino]-propionic acid methyl ester (Intermediate 27)

Intermediate 26 (2.14 g, 6.27 mmol) and intermediate 9 (2.15 g, 5.7 mmol) were coupled in close analogy to the procedure described in 3.3) to intermediate 27. The crude product was purified by prep. HPLC and lyophilized. Yield: 744 mg, 23%.

7.5) (S)-3-[(5-Chloro-thiophene-2-carbonyl)-amino]-2-[3-(2-oxo-piperidin-1-yl)-2-trifluoromethyl-benzenesulfonylamino]-propionic acid (Intermediate 28)

Intermediate 27 (738 mg, 1.3 mmol) was converted in close analogy to the procedure described in 3.4) to intermediate 28. The crude product was used without further purification in the next step.

7.6) 5-Chloro-thiophene-2-carboxylic acid {(S)-3-(4-cyclopropyl-piperazin-1-yl)-3-oxo-2-[3-(2-oxo-piperidin-1-yl)-2-trifluoromethyl-benzenesulfonylamino]propyl}amide trifluoroacetate Intermediate 28 (260 mg, 0.43 mmol) and 1-cyclopropyl-piperazine dihydro chloride (90 mg, 0.45 mmol) were coupled in close analogy to the procedure described in 3.5) using DMF as solvent. The mixture was purified by prep. HPLC. Yield after lyophilization: 172 mg, 52%, colorless, amorphous solid.

MS (ES$^+$): m/e=662.3/664.4, chloro pattern.

Example 8

5-Chloro-thiophene-2-carboxylic acid {(S)-3-(4-cyclopropyl-piperazin-1-yl)-2-[2-difluoromethoxy-3-(2-oxo-piperidin-1-yl)-benzenesulfonylamino]-3-oxo-propyl}-amide trifluoroacetate

8.1) 1,3-Dibromo-2-difluoromethoxy-benzene (Intermediate 29)

Analogous to (J. Org. Chem. 2005, 3021-3030):
2,6-dibromo-phenol (25.19 g, 100 mmol) and K$_2$CO$_3$ (16.59 g, 120 mmol) were dissolved in 180 ml of DMF and 20 ml of water. Sodium chlorodifluoroacetate (24.39 g, 160 mmol) was then added and the mixture was heated to 100° C. for 3 h. After cooling the product was crashed out by the addition of water. Filtration and washing gives a yield of 28.2 g, 93%.

8.2) 1-Benzylsulfanyl-3-bromo-2-difluoromethoxy-benzene (Intermediate 30)

Intermediate 29 (28.08 g, 93 mmol) was converted to Intermediate 30 as described in detail following the procedures in 6.1.

Yield after chromatography on silica gel: 18.78 g, 59%, oil.

8.3) 1-(3-Benzylsulfanyl-2-difluoromethoxy-phenyl) piperidin-2-one (Intermediate 31)

Intermediate 30 (18.64 g, 54 mmol) was converted to Intermediate 31 as described in detail following the procedure in 7.2).

Yield: 8.98 g, 46%, crystalline solid from n-heptane-ethyl acetate (4:1)

8.4) 2-difluoromethoxy-3-(2-oxo-piperidin-1-yl)-benzenesulfonyl chloride (Intermediate 32)

Intermediate 31 (1.563 g, 4.3 mmol) was submitted to the chemistry described in step 7.3). Yield: 1.25 g, 86%, crystalline solid from MTBE-n-heptane (9:1)

8.5) (S)-3-[(5-Chloro-thiophene-2-carbonyl)-amino]-2-[2-difluoromethoxy-3-(2-oxo-piperidin-1-yl)-benzenesulfonylamino]-propionic acid methyl ester (Intermediate 33)

Intermediate 32 (1.25 g, 3.69 mmol) and intermediate 9 (1.39 g, 3.69 mmol) were coupled in close analogy to the procedure described in 3.3) to intermediate 33. The crude product was used without further purification in the next step.

8.6) (S)-3-[(5-Chloro-thiophene-2-carbonyl)-amino]-2-[2-difluoromethoxy-3-(2-oxo-piperidin-1-yl)-benzenesulfonylamino]-propionic acid (Intermediate 34)

Intermediate 33 (2.09 g, 3.69 mmol) was converted in close analogy to the procedure described in 3.4) to intermediate 34. The crude product was used without further purification in the next step.

8.7) 5-Chloro-thiophene-2-carboxylic acid {(S)-3-(4-cyclopropyl-piperazin-1-yl)-2-[2-difluoromethoxy-3-(2-oxo-piperidin-1-yl)-benzenesulfonylamino]-3-oxo-propyl}-amide trifluoroacetate Intermediate 34 (249 mg, 0.45 mmol) and 1-cyclopropyl-piperazine dihydro chloride (96 mg, 0.48 mmol) were coupled in close analogy to the procedure described in 3.5) using DMF as solvent.

The mixture was purified by prep. HPLC. Yield after lyophilization: 274 mg, 79%, colorless, amorphous solid. MS (ES$^+$): m/e=660.3/662.4, chloro pattern.

Example 9

1-{(S)-3-[(5-Chloro-thiophene-2-carbonyl)-amino]-2-[2-difluoromethoxy-3-(2-oxo-piperidin-1-yl)-benzenesulfonylamino]-propionyl}-piperidine-4-carboxylic acid ethyl ester Intermediate 34 (258 mg, 0.467 mmol) and Piperidine-4-carboxylic acid ethyl ester (81 mg, 0.514 mmol) were coupled in close analogy to the procedure described in 3.5) using DMF as solvent. The mixture was purified by prep. HPLC. Yield after lyophilization: 253 mg, 78%, colorless, amorphous solid.
MS (ES$^+$): m/e=691.1/693.2, chloro pattern.

Example 10

1-{(S)-3-[(5-Chloro-thiophene-2-carbonyl)-amino]-2-[2-difluoromethoxy-3-(2-oxo-piperidin-1-yl)-benzenesulfonylamino]-propionyl}-piperidine-4-carboxylic acid The ethyl ester (1-{(S)-3-[(5-Chloro-thiophene-2-carbonyl)-amino]-2-[2-difluoromethoxy-3-(2-oxo-piperidin-1-yl)-benzenesulfonylamino]-propionyl}-piperidine-4-carboxylic acid ethyl ester) from example 9 (128 mg, 0.185 mmol) was treated with LiOH (222 µl, 0.555 mmol, 2.5 N in water) in THF/ethanol/water (2 ml, 1 ml, 0.5 ml). After 2.5 h the reaction was brought to pH=1-2 using 2 N HCl and further diluted with 30 ml water. The product crystallized from the aq layer and can be separated by filtration. Yield: 54 mg, 44%, colorless crystals.
MS (ES$^+$): m/e=663.4/665.4, chloro pattern.

Example 11

5-Chloro-thiophene-2-carboxylic acid {(S)-2-[2-difluoromethoxy-3-(2-oxo-piperidin-1-yl)-benzenesulfonylamino]-3-[4-(3-methyl-[1,2,4]oxadiazol-5-yl)-piperidin-1-yl]-3-oxo-propyl}amide 1-{(S)-3-[(5-Chloro-thiophene-2-carbonyl)-amino]-2-[2-difluoromethoxy-3-(2-oxo-piperidin-1-yl)-benzenesulfonylamino]-propionyl}-piperidine-4-carboxylic acid (69 mg, 0.104 mmol) from Example 10 in DMF (1 ml) and DIPEA (91 µl, 0.52 mmol) was treated with TBTU (35 mg, 0.109 mmol) and HOAT (3 mg, 0.021 mmol) and stirred for 2 min before N-hydroxy-acetamidine (9 mg, 0.115 mmol) was added. Stirring was continued for 1.25 h at RT. After that the reaction mixture was heated at 110° C. for 2 h. The mixture was purified by prep. HPLC. Yield after lyophilization: 44 mg, 60%, colorless, amorphous solid. MS (ES$^+$): m/e=701.2/703.2, chloro pattern.

Example 12

5-Chloro-thiophene-2-carboxylic acid [(S)-2-[2-chloro-5-fluoro-3-(2-oxo-piperidin-1-yl)-benzenesulfonylamino]-3-(4-methyl-piperazin-1-yl)-3-oxo-propyl]-amide trifluoro acetate 12.1) 1-Benzylsulfanyl-3-bromo-2-chloro-5-fluoro-benzene (Intermediate 35)

Commercially available 1,3-dibromo-2-chloro-5-fluoro-benzene (25 g, 86.7 mmol), was converted as described in 6.1) to intermediate 35. The remaining solid after workup (33 g) is chromatographed on silica gel using n-heptane-ethylacetate (4:1) as eluent. Yield: 16 g, 56%.

12.2) 1-(3-Benzylsulfanyl-2-chloro-5-fluoro-phenyl) piperidin-2-one (Intermediate 36)

Intermediate 35 (4 g, 12.06 mmol) was coupled with piperidin-2-one (1.434 g, 14.47 mmol) in close analogy to the procedure described in step 1.6). After workup the crude oil is purified by chromatography on silica gel (n-heptane-ethyl acetate 4:1).
Yield: 1.8 g, 43

12.3) 2-Chloro-5-fluoro-3-(2-oxo-piperidin-1-yl) benzenesulfonyl chloride (Intermediate 37)

Intermediate 36 (1.8 g, 5.14 mmol) was converted in close analogy to the procedure described in 1.7) to intermediate 37. The crude product was used without further purification in the next step.

12.4) (S)-2-[2-Chloro-5-fluoro-3-(2-oxo-piperidin-1-yl)-benzenesulfonylamino]-3-[(5-chloro-thiophene-2-carbonyl)-amino]-propionic acid methyl ester (Intermediate 38)

Intermediate 37 (1.63 g, 5 mmol) and intermediate 9 (1.31 g, 5 mmol) were coupled in close analogy to the procedure described in 3.3) to intermediate 38. The crude product was used without purification in the next step.

12.5) (S)-2-[2-Chloro-5-fluoro-3-(2-oxo-piperidin-1-yl)-benzenesulfonylamino]-3-[(5-chloro-thiophene-2-carbonyl)-amino]-propionic acid (Intermediate 39)

Intermediate 38 (1.10 g, 1.99 mmol) was converted in close analogy to the procedure described in 3.4) to intermediate 39. The crude product was used without further purification in the next step.

12.6) 5-Chloro-thiophene-2-carboxylic acid [(S)-2-[2-chloro-5-fluoro-3-(2-oxo-piperidin-1-yl)-benzenesulfonylamino]-3-(4-methyl-piperazin-1-yl)-3-oxo-propyl]-amide trifluoro acetate Intermediate 39 (300 mg, 0.56 mmol) and 1-methyl-piperazine (55.8 mg, 0.56 mmol) were coupled in close analogy to the procedure described in 3.5) using DMF as solvent. The mixture was purified by prep. HPLC. Yield after lyophilization: 234 mg, 57%, colorless, amorphous solid. MS (ES$^+$): m/e=620.3

Example 13

5-Chloro-thiophene-2-carboxylic acid [(S)-2-(2-chloro-5-fluoro-3-pyrrolidin-1-yl-benzenesulfonylamino)-3-(4-methyl-piperazin-1-yl)-3-oxo-propyl]-amide trifluoro acetate 13.1) 1-(3-Benzylsulfanyl-2-chloro-5-fluoro-phenyl)-pyrrolidine (Intermediate 40)

Intermediate 35 (1 g, 3.02 mmol), pyrrolidine (0,257 g, 3.62 mmol), Pd$_2$dba$_3$ (55 mg, 0.06 mmol, 2 mol-%), BINAP (75 mg, 0.12 mmol, 4 mol-%) and NaOtBu (376 mg, 3.92 mmol) were suspended in 25 ml of dry, degassed toluene and refluxed for 2 h under argon atmosphere. After full conversion

13.2) 2-Chloro-5-fluoro-3-pyrrolidin-1-yl-benzenesulfonyl chloride (Intermediate 41)

Intermediate 40 (1.1 g, 3.42 mmol) was converted in close analogy to the procedure described in 1.7) to intermediate 41. The crude product was used without further purification in the next step.

13.3) (S)-2-(2-Chloro-5-fluoro-3-pyrrolidin-1-yl-benzenesulfonylamino)-3-[(5-chloro-thiophene-2-carbonyl)-amino]-propionic acid methyl ester trifluoro acetate (Intermediate 42)

Intermediate 41 (894 mg, 3 mmol) and intermediate 9 (788 mg, 3 mmol) were coupled in close analogy to the procedure described in 3.3) to intermediate 42. The crude product was used purified using prep. HPLC. Yield after lyophilization: 0.23 g, 12%.

13.4) (S)-2-(2-Chloro-5-fluoro-3-pyrrolidin-1-yl-benzenesulfonylamino)-3-[(5-chloro-thiophene-2-carbonyl)-amino]-propionic acid (Intermediate 43)

Intermediate 42 (230 mg, 0.44 mmol) was converted in close analogy to the procedure described in 3.4) to intermediate 43. The crude product was used without further purification in the next step.

13.5) 5-Chloro-thiophene-2-carboxylic acid [(S)-2-(2-chloro-5-fluoro-3-pyrrolidin-1-yl-benzenesulfonylamino)-3-(4-methyl-piperazin-1-yl)-3-oxo-propyl]-amide trifluoro acetate Intermediate 43 (240 mg, 0.47 mmol) and 1-methyl-piperazine (47.1 mg, 0.47 mmol) were coupled in close analogy to the procedure described in 3.5). The mixture was purified by prep. HPLC. Yield after lyophilization: 121 mg, 37%, colorless, amorphous solid. MS (ES$^+$): m/e=592.1/594.1, chloro pattern.

Example 14

5-Chloro-thiophene-2-carboxylic acid [(S)-2-[2-chloro-3-(2-oxo-pyrrolidin-1-yl)-benzenesulfonylamino]-3-(4-methyl-piperazin-1-yl)-3-oxo-propyl]-amide trifluoro acetate

14.1) 1-(3-Benzylsulfanyl-2-chloro-phenyl)-pyrrolidin-2-one (Intermediate 44)

Intermediate 35 (35 g, 313.6 mmol) was coupled with pyrrolidin-2-one (11.396 g, 133.91 mmol) in close analogy to the procedure described in step 1.6). After workup the crude product was used without further purification.

14.2) 2-Chloro-3-(2-oxo-pyrrolidin-1-yl)-benzenesulfonyl chloride (Intermediate 45)

Intermediate 44 (3.0 g, 9.44 mmol) was converted in close analogy to the procedure described in 1.7) to intermediate 45. The crude product was used without further purification in the next step.

14.3) (S)-2-[2-Chloro-3-(2-oxo-pyrrolidin-1-yl)-benzenesulfonylamino]-3-[(5-chloro-thiophene-2-carbonyl)-amino]-propionic acid methyl ester (Intermediate 46)

Intermediate 45 (2.647 g, 9 mmol) and intermediate 9 (2.364 g, 9 mmol) were coupled in close analogy to the procedure described in 3.3) to intermediate 46. The crude product was used without purification in the next step.

14.4) (S)-2-[2-Chloro-3-(2-oxo-pyrrolidin-1-yl)-benzenesulfonylamino]-3-[(5-chloro-thiophene-2-carbonyl)-amino]-propionic acid (Intermediate 47)

Intermediate 46 (4.6 g, 8.84 mmol) was converted in close analogy to the procedure described in 3.4) to intermediate 47. The crude product was used without further purification in the next step.

14.5) 5-Chloro-thiophene-2-carboxylic acid [(S)-2-[2-chloro-3-(2-oxo-pyrrolidin-1-yl)-benzenesulfonylamino]-3-(4-methyl-piperazin-1-yl)-3-oxo-propyl]-amide trifluoro acetate Intermediate 47 (200 mg, 0.39 mmol) and 1-methyl-piperazine (39.6 mg, 0.39 mmol) were coupled in close analogy to the procedure described in 3.5). The mixture was purified by prep. HPLC. Yield after lyophilization: 70.4 mg, 26%, colorless, amorphous solid. MS (ES$^+$): m/e=588.2/590.2, chloro pattern.

Example 15

5-Chloro-thiophene-2-carboxylic acid {(S)-2-[2-chloro-3-(2-oxo-pyrrolidin-1-yl)-benzenesulfonylamino]-3-oxo-3-piperazin-1-yl-propyl}-amide Intermediate 47 (150 mg, 0.3 mmol) and piperazine (25.5 mg, 0.3 mmol) were coupled in close analogy to the procedure described in 3.5). The mixture was purified by prep.
HPLC. Yield after lyophilization: 14.5 mg, 7%, colorless, amorphous solid.
MS (ES$^+$): m/e=574.2/576.2, chloro pattern

Example 16

5-Chloro-thiophene-2-carboxylic acid {(S)-2-[5-fluoro-2-methyl-3-(2-oxo-pyrrolidin-1-yl)-benzenesulfonylamino]-3-[4-(2-methoxy-ethyl)-piperazin-1-yl]-3-oxo-propyl}-amide trifluoro acetate

16.1) 3-Bromo-5-fluoro-2-methyl-phenylamine (Intermediate 48)

To iron powder (325 mesh, 2.25 g, 40.3 mmol) in 30 ml water and 80 ml isopropanol was added commercially available 1-bromo-5-fluoro-2-methyl-3-nitro-benzene (3.04 g, 13 mmol) in 45 ml isopropanol and NH$_4$Cl (1.46 g, 27.3 mmol). The resulting mixture was heated at 110° C. for 2 h. After evaporation of most of the isopropanol the aq solution was extracted with ethyl acetate three times. The combined organic layers were washed with water and brine, dried over MgSO$_4$, filtered and evaporated. The crude product was used without further purification in the next step.

16.2) 1-(3-Bromo-5-fluoro-2-methyl-phenyl)-pyrrolidin-2-one (Intermediate 49)

a) Intermediate 48 (2.92 g, 14.3 mmol) in DCM (23 ml) and pyridine (1.5 ml, 18.59 mmol) was treated with a solution of 4-chloro-butyryl chloride (1.6 ml, 14.3 mmol) in DCM (7 ml) and stirred for 1.25 h at RT. The reaction mixture was evaporated to dryness and the resulting solid dissolved in MTBE and ethyl acetate. After washing with water and brine and drying over MgSO$_4$, the solution was filtered and evaporated. The product crystallized upon standing (3.8 g).

b) 3.67 g (11.9 mmol) of this product in DMF (40 ml) were treated with KOtBu (1.47 g, 13.09 mmol) which was added in 3 portions under argon. After stirring for 1 h at RT the mixture is poured onto 1N aq KHSO$_4$-solution (150 ml) and after 5 min water (150 ml) was added. The aqueous solution was extracted with MTBE three times. The combined organic layers were washed with water and brine, dried over MgSO$_4$, filtered and evaporated. The crude product was purified by chromatography on silica gel. Yield: 1.728 g, 53%.

16.3) 1-(3-Benzylsulfanyl-5-fluoro-2-methyl-phenyl)-pyrrolidin-2-one (Intermediate 50)

Intermediate 49 (1.714 g, 6.3 mmol) was converted to intermediate 50 as described in 6.1). The remaining solid after workup was chromatographed on silica gel using n-heptane-ethylacetate (45:1) as eluent. Yield: 1.476 g, 74%.

16.4) 5-Fluoro-2-methyl-3-(2-oxo-pyrrolidin-1-yl)-benzenesulfonyl chloride (Intermediate 51)

Intermediate 50 (726 mg, 2.3 mmol) was converted to intermediate 37 in close analogy to the procedure described in 1.7). The crude product was used without further purification in the next step.

16.5) (S)-3-[(5-Chloro-thiophene-2-carbonyl)-amino]-2-[5-fluoro-2-methyl-3-(2-oxo-pyrrolidin-1-yl)-benzenesulfonylamino]-propionic acid methyl ester (Intermediate 52)

Intermediate 51 (873 mg, 2.3 mmol) and intermediate 9 (787 mg, 2.09 mmol) were coupled to intermediate 52 in close analogy to the procedure described in 3.3). The crude product was used without purification in the next step.

16.6) (S)-3-[(5-Chloro-thiophene-2-carbonyl)-amino]-2-[5-fluoro-2-methyl-3-(2-oxo-pyrrolidin-1-yl)-benzenesulfonylamino]-propionic acid (Intermediate 53)

Intermediate 52 (236 mg, 0.455 mmol) was converted to intermediate 53 in close analogy to the procedure described in 3.4). The crude product was used without further purification in the next step.

16.7) 5-Chloro-thiophene-2-carboxylic acid {(S)-2-[5-fluoro-2-methyl-3-(2-oxo-pyrrolidin-1-yl)-benzenesulfonylamino]-3-[4-(2-methoxy-ethyl)-piperazin-1-yl]-3-oxo-propyl}-amide trifluoro acetate Intermediate 53 (183 mg, 0.363 mmol) and 1-(2-methoxy-ethyl)-piperazine (58 mg, 0.399 mmol) were coupled in close analogy to the procedure described in 3.5) using DMF as solvent. The mixture was purified by prep. HPLC. Yield after lyophilization: 217 mg, 80%, colorless, amorphous solid.

MS (ES$^+$): m/e=630.1, 632.1, chloro pattern.

Example 17

5-Chloro-thiophene-2-carboxylic acid [(S)-2-[2-difluoromethyl-3-(2-oxo-pyrrolidin-1-yl)-benzenesulfonylamino]-3-(4-methyl-piperazin-1-yl)-3-oxo-propyl]-amide trifluoro acetate

17.1) 1,3-Dibromo-2-difluoromethyl-benzene (Intermediate 54)

2,6-Dibromo-benzaldehyde (5.96 g, 22.5 mmol) (prepared as described in J. Org. Chem., 2003, 5384-5387) was placed in a Teflon-coated flask and dissolved in DCM (200 ml). BAST (9.96 g, 45 mmol) was slowly added and the reaction mixture was stirred at RT for 6 h. The reaction mixture was then slowly added to a vigorously stirred sat. aq NaHCO$_3$-solution (400 ml) under cooling with ice. After 1 h the phases were separated and the aqueous layer was extracted with DCM three times. The combined organic layers were washed two times with water, dried over MgSO$_4$, filtered and evaporated to dryness. The crude product was used without further purification.

17.2) 1-Benzylsulfanyl-3-bromo-2-difluoromethyl-benzene (Intermediate 55)

Intermediate 54 (7.25 g, 22.75 mmol) was converted as described in 6.1) to intermediate 55. The remaining solid after workup was chromatographed on silica gel using n-heptane-ethylacetate as eluent. Yield: 2.035 g, 27% (2 steps).

17.3) 1-(3-Benzylsulfanyl-2-difluoromethyl-phenyl)-pyrrolidin-2-one (Intermediate 56)

Intermediate 55 (2.008 g, 6.1 mmol) was coupled with pyrrolidin-2-one (0.623 g, 7.32 mmol) in close analogy to the procedure described in step 1.6). After workup the crude oil crystallized upon standing overnight and was then triturated with MTBE.

Yield: 1.216 g, 60%

17.4) 2-Difluoromethyl-3-(2-oxo-pyrrolidin-1-yl)-benzenesulfonyl chloride (Intermediate 57)

Intermediate 56 (1.2 g, 14.4 mmol) was converted to intermediate 57 in close analogy to the procedure described in 1.7). The crude product was used without further purification in the next step.

17.5) (S)-3-[(5-Chloro-thiophene-2-carbonyl)-amino]-2-[2-difluoromethyl-3-(2-oxo-pyrrolidin-1-yl)-benzenesulfonylamino]-propionic acid methyl ester (Intermediate 58)

Intermediate 57 (1.58 g, 2.88 mmol) and intermediate 9 (1.085 g, 2.88 mmol) were coupled to intermediate 58 in close analogy to the procedure described in 3.3). The crude product was purified by chromatography on silica gel. Yield: 138 mg, 9%.

17.6) (S)-3-[(5-Chloro-thiophene-2-carbonyl)-amino]-2-[2-difluoromethyl-3-(2-oxo-pyrrolidin-1-yl)-benzenesulfonylamino]-propionic acid (Intermediate 59)

Intermediate 58 (138 mg, 0.257 mmol) was converted to intermediate 59 in close analogy to the procedure described in 3.4). The crude product was used without further purification in the next step.

17.7) 5-Chloro-thiophene-2-carboxylic acid [(S)-2-[2-difluoromethyl-3-(2-oxo-pyrrolidin-1-yl)-benzenesulfonylamino]-3-(4-methyl-piperazin-1-yl)-3-oxo-propyl]-amide trifluoro acetate Crude intermediate 59 (270 mg) and 1-methyl-piperazine (32 µl, 0.283 mmol) were coupled in close analogy to the procedure described in 3.5) using DMF as solvent. The mixture was purified 2 times by prep. HPLC. Yield after lyophilization: 63 mg, 34% (2 steps), colorless, amorphous solid. MS (ES$^+$): m/e=604.0/606.1, chloro pattern.

Example 18

5-Chloro-thiophene-2-carboxylic acid [(S)-2-(2-ethyl-3-pyridin-2-yl-benzenesulfonylamino)-3-((S)-3-methyl-morpholin-4-yl)-3-oxo-propyl]-amide hydro chloride 18.1) 2-(3-Bromo-2-ethyl-phenyl)-pyridine (Intermediate 60)

A solution of iPrMgCl (16.50 ml, 2M in THF, 33 mmol.) was added dropwise at RT under argon to intermediate 4 (7.92 g, 30 mmol) and then heated at 65° C. for 1.5 h. The mixture was then added via syringe to a suspension of dry ZnCl$_2$ (4.1 g, 30 mmol) in dry THF (15 mL) cooled to 0° C. under argon. The resulting suspension was stirred at RT for 30 min. Then 2-bromo-pyridine (2.87 ml, 30 mmol) and PdCl$_2$*dppf (1.22 g) were added and the mixture was refluxed for 2 h.

The reaction mixture was then quenched by addition of a 5% solution of citric acid (150 mL) and extracted with ethyl acetate (2×200 ml). The organic layers were consecutively washed with a 5% solution of citric acid (150 ml) and brine (150 ml), dried over Na$_2$SO$_4$, filtered and evaporated under reduced pressure. The crude material was chromatographed on silica gel. Elution with ethyl acetate/cyclohexane yielded 4.7 g (60%) of the title compound as a colorless oil.

18.2) 2-Ethyl-3-pyridin-2-yl-benzenesulfonyl chloride (Intermediate 61)

To a solution of intermediate 60 (17.94 g, 68.46 mmol) in dry THF (120 ml)) at −78° C. under argon was added n-BuLi (2.5 M, 30.12 ml, 75.31 mmol) dropwise to such a rate that the temperature did not rise above −60° C. After 1 h at −78° C. the reaction mixture was treated with SO$_2$, diluted with pentane at RT, filtered, washed with pentane to yield 17.3 g of the corresponding lithium sulfinate and stored under argon, yield: 99%. To a suspension of the lithium sulfinate (1.09 g, 4.30 mmol) at RT under argon in DCM (20 ml) was added NCS (0.75 g, 5.59 mmol) portionwise. After 1.5 h at RT the reaction mixture was diluted with ether (100 ml), washed consecutively with water (40 ml) and brine (40 ml), dried over Na$_2$SO$_4$, filtered and evaporated under reduced pressure. The crude material was quickly chromatographed on silica gel.

Elution with ether/pentane from 0 to 100% of ether gave 0.936 g of intermediate 61 as a yellow oil, yield: 77%.

18.3) 5-Chloro-thiophene-2-carboxylic acid [(S)-2-(2-ethyl-3-pyridin-2-yl-benzene-sulfonylamino)-3-((S)-3-methyl-morpholin-4-yl)-3-oxo-propyl]-amide hydro chloride 5-Chloro-thiophene-2-carboxylic acid [(S)-2-amino-3-((S)-3-methyl-morpholin-4-yl)-3-oxo-propyl]-amide (Intermediate 3) (95 mg, 0.287 mmol) was dissolved in 2 ml DCM and DIPEA (151 µl, 0.861 mmol). Intermediate 61 (81 mg, 0.287 mmol) in 2 ml DCM was slowly added and the reaction was stirred for 1.5 h. Then the solution was evaporated to dryness and purified by prep. HPLC. After lyophilization the title compound is obtained as colorless, amorphous solid. The material was dissolved in 20 ml water and 150 µl 4N HCl in dioxane were added. The solution was lyophilized again. Yield: 77 mg, 44%. MS (ES$^+$): m/e=577.1/579.1, chloro pattern.

Example 19

5-Chloro-thiophene-2-carboxylic acid [(S)-2-[2-ethyl-3-(1-oxy-pyridin-2-yl)-benzenesulfonylamino]-3-((S)-3-methyl-morpholin-4-yl)-3-oxo-propyl]-amide 5-Chloro-thiophene-2-carboxylic acid [(S)-2-(2-ethyl-3-pyridin-2-yl-benzenesulfonyl-amino)-3-((S)-3-methyl-morpholin-4-yl)-3-oxo-propyl]-amide hydrochloride, Example 18 (34 mg, 0.055 mmol) was dissolved in DCM (2 ml) and extracted with 2 N aq NaOH. The organic layer was separated and treated with MCPBA (27 mg, 0.11 mmol) under stirring for 17 h. Then the mixture was diluted with DCM (20 ml) and extracted five times with sat. aq NaHCO$_3$ (10 ml). The combined aqueous layers were washed with DCM. The combined organic layers were then extracted with 1 N aq NaOH-solution 4× (10 ml). The combined aqueous layers were acidified (pH ~1) using 2 N HCl and extracted with DCM three times. The combined organic layers were dried with MgSO$_4$, filtered and evaporated. The crude material was further purified by prep. HPLC and lyophilized. Yield: 23 mg, 71%.
MS (ES$^+$): m/e=593.2/595.2, chloro pattern.

Example 20

5-Chloro-thiophene-2-carboxylic acid [(S)-2-[3-(5-chloro-1-methyl-2-oxo-1,2-dihydro-pyridin-3-yl)-2-ethyl-benzenesulfonylamino]-3-((S)-3-methyl-morpholin-4-yl)-3-oxo-propyl]-amide 20.1) 2-(3-Benzylsulfanyl-2-ethyl-phenyl)-4,4,5,5-tetramethyl-[1,3,2]dioxaborolane (Intermediate 62)

A mixture of intermediate 5 (10 g, 32.6 mmol), 4,4,5,5,4',4',5',5'-octamethyl-[2,2']bi[[1,3,2]dioxaborolanyl] (11.6 g, 45.6 mmol) and KOAc (12.8 g, 130.2 mmol) in DMSO (35 ml) was stirred for 15 min under argon at RT then PdCl$_2$(dppf) (1.2 g, 1.63 mmol) was added and the mixture was heated for 2.5 h at 110° C. After cooling to RT the mixture was diluted with ethyl acetate (300 ml), washed with water (2×400 ml) and brine (200 ml), dried over Na$_2$SO$_4$, and evaporated under reduced pressure. The crude material was chromatographed on silica gel. Elution with ether/pentane from 0 to 5% of ether gave 8 g of the title compound, yield=77%, yellow oil.

20.2) 3-Bromo-1-methyl-1H-pyridin-2-one (Intermediate 63)

To a solution of 3-bromo-pyridin-2-ol (2.06 g, 11.5 mmol.) in DMF (10 ml) was added NaH (60%, 0.50 g, 12.64 mmol.) portionwise at 0° C. under argon. After 30 min methyl iodide (0.79 ml, 12.64 mmol.) was added dropwise and the reaction mixture was stirred for 15 h at RT. The mixture was diluted with ethyl acetate (100 ml), washed with water (2×200 ml) and brine (100 ml), dried over $Na_2SO_4$ and evaporated under reduced pressure. The crude material was chromatographed on silica gel. Elution with ethyl acetate/cyclohexane from 0 to 50% of ethyl acetate gave 0.92 g of intermediate 63, yield=42%, yellow oil.

20.3) 3-(3-Benzylsulfanyl-2-ethyl-phenyl)-1-methyl-1H-pyridin-2-one (Intermediate 64)

A mixture of intermediate 63 (0.9 g, 4.79 mmol), intermediate 62 (1.69 g, 4.79 mmol) and $Ba(OH)_2$*$8H_2O$ (4.53 g, 14.36 mmo) in water (1.0 ml) and DMSO (10 mL) was stirred for 15 min under argon at RT. Then, $PdCl_2$(dppf) (0.175, 0.24 mmol) was added and the mixture was heated for 3 h at 110° C. After cooling to RT the mixture was diluted with ethyl acetate (200 ml), washed with water (2×300 ml) and brine (200 ml), dried over $Na_2SO_4$ and evaporated under reduced pressure. The crude material was chromatographed on silica gel. Elution with ethyl acetate/cyclohexane from 0 to 50% of ethyl acetate gave 1.09 g of intermediate 64 as a green oil, yield=68%.

20.4) 3-(5-Chloro-1-methyl-2-oxo-1,2-dihydro-pyridin-3-yl)-2-ethyl-benzenesulfonyl chloride (Intermediate 65)

Intermediate 62 (79 mg, 0.235 mmol) was dissolved in 3 ml DCM and treated with water (21 µl, 1.175 mmol), AcOH (67 µl, 1.175 mmol) and $SO_2Cl_2$ (95 µl, 1.175 mmol) according to procedure 1.7). After drying over $MgSO_4$ and evaporation to dryness the crude intermediate 65 was used without further purification in the next step.

20.5) 5-Chloro-thiophene-2-carboxylic acid [(S)-2-[3-(5-chloro-1-methyl-2-oxo-1,2-dihydro-pyridin-3-yl)-2-ethyl-benzenesulfonylamino]-3-((S)-3-methyl-morpholin-4-yl)-3-oxo-propyl]-amide 5-Chloro-thiophene-2-carboxylic acid [(S)-2-amino-3-((S)-3-methyl-morpholin-4-yl)-3-oxo-propyl]-amide, Intermediate 3 (78 mg, 0.235 mmol) was dissolved in 3 ml DCM/1,4-Dioxane (1:1) and DIPEA (164 µl, 0.94 mmol). Intermediate 65 (82 mg, 0.235 mmol) in 1.5 ml DCM was slowly added and the reaction was stirred for 2 h. Then the solution was evaporated to dryness and purified by prep. HPLC. After lyophilization the title compound is obtained as colorless, amorphous solid.

Yield: 35 mg, 23% MS (ES$^+$): m/e=641.1/643.1, chloro pattern.

Example 21

5-Chloro-thiophene-2-carboxylic acid [(S)-2-[3-(5-chloro-1-methyl-2-oxo-1,2-dihydro-pyridin-3-yl)-2-methoxy-benzenesulfonylamino]-3-(4-cyclopropyl-piperazin-1-yl)-3-oxo-propyl]-amide hydrochloride

21.1) 3-Bromo-1-methyl-1H-pyridin-2-one (Intermediate 63), large scale

To a solution of 3-bromo-pyridin-2-ol (10 g, 57.47 mmol) in DMF (100 ml) at 0° C. was added NaH (60%, 2.52 g, 63.22 mmol) portionwise under argon. After 30 min methyl iodide (4.29 ml, 68.97 mmol) was added dropwise and the reaction mixture was stirred for 15 h at RT. The mixture was diluted with ethyl acetate (100 ml), washed with water (2×200 ml) and brine (100 ml), dried over $Na_2SO_4$, and evaporated under reduced pressure. The crude product was used without further purification in step 21.5).

21.2) 2,6-dibromo-methoxy-benzene (Intermediate 66)

To a solution of 2,6-dibromo-phenol (30 g, 119.09 mmol) in DMF (160 ml) at 0° C. was added NaH (60%, 5.72 g, 142.91 mmol) portionwise under argon.

After 30 min methyl iodide (7.78 ml, 125.05 mmol) was added dropwise and the reaction mixture was stirred for 4 h at RT. The mixture was diluted with ethyl acetate (100 ml), washed with water (2×200 ml) and brine (100 ml), dried over $Na_2SO_4$, and evaporated under reduced pressure. The crude product was purified by chromatography on silica gel (eluent: AcOEt/cyclohexane 1/4). Yield: 29.08 g, 92%

21.3) 1-Benzylsulfanyl-3-bromo-2-methoxy-benzene (Intermediate 67)

Intermediate 66 (42 g, 157.94 mmol) was converted to intermediate 67 in analogy to the procedure described in 6.1). The reaction was quenched by addition of 150 ml of $H_2O$. After extraction with ethyl acetate (three times) the combined organic layers were washed with water, dried with $Na_2SO_4$, evaporated to dryness and the product was purified by silica gel chromatography (cyclohexane/ethyl acetate 100/0 to 4/1).

Yield: 45 g, 92

21.4) 2-(3-Benzylsulfanyl-2-methoxy-phenyl)-4,4,5,5-tetramethyl-[1,3,2]dioxaborolane (Intermediate 68)

A mixture of intermediate 67 (5 g, 16.17 mmol), 4,4,5,5,4',4',5',5'-octamethyl-[2,2']bi[[1,3,2]dioxaborolanyl] (5.75 g, 22.64 mmol) and KOAc (6.35 g, 64.68 mmol) in DMSO (100 ml) was stirred for 15 min under argon at RT. Then $PdCl_2$(dppf) (0.66 g, 0.81 mmol) was added and the mixture was heated for 16 h at 110° C. After cooling to RT the mixture was diluted with ethyl acetate (300 ml) washed with water (2×400 ml) and brine (200 ml), dried over $Na_2SO_4$, and evaporated under reduced pressure. The crude material was purified by silica gel chromatography (elution with cyclohexane/ethyl acetate from 0 to 5% of ethyl acetate). Yield: 5.24 g, 91%.

21.5) 3-(3-Benzylsulfanyl-2-methoxy-phenyl)-1-methyl-1H-pyridin-2-one (Intermediate 69)

A mixture of intermediate 63 from step 21.1 (1.58 g, 8.42 mmol), intermediate 68 (3 g, 8.42 mmol) and $Ba(OH)_2$;$8H_2O$ (7.97 g, 25.26 mmol) in water (1.82 ml) and DMSO (17 ml) was stirred for 15 min under argon at RT. Then $PdCl_2$(dppf) (0.344 g, 0.42 mmol) was added and the mixture was heated for 4 h at 110° C. After cooling to RT the mixture was diluted with ethyl acetate (200 ml), washed with water (2×300 ml) and brine (200 ml), dried over $Na_2SO_4$ and evaporated under reduced pressure. The crude product was purified by silica gel chromatography. Elution with DCM/MeOH from 0 to 2% of MeOH gave 0.812 g, yield=29% of intermediate 69.

21.6) 2-Methoxy-3-(1-methyl-2-oxo-1,2-dihydro-pyridin-3-yl)-benzenesulfonyl chloride and 3-(5-Chloro-1-methyl-2-oxo-1,2-dihydro-pyridin-3-yl)-2-methoxy-benzenesulfonyl chloride (Mixture of Intermediates 70a and 70b)

Intermediate 69 (1.497 g, 4.44 mmol) was dissolved in 20 ml DCM and treated with water (0.32 ml, 17.74 mmol), AcOH (1.27 ml, 22.18 mmol) and $SO_2Cl_2$ (1.44 ml, 17.74 mmol) at 0° C. After stirring for 5 min at 0° C. and 20 min at RT the reaction was cooled back to 0° C. and quenched by the addition of 10 ml of water. The aqueous solution was extracted with DCM (three times) and the combined organic layers were washed with cold water. Drying over $Na_2SO_4$ and evaporation to dryness yielded 1.39 g (yield 92%) of the crude mixture of intermediates 70a and 70b (ratio: 3:7) which were used without further purification in the next step.

21.7) (S)-2-[3-(1-methyl-2-oxo-1,2-dihydro-pyridin-3-yl)-2-methoxy-benzenesulfonyl-amino]-3-[(5-chloro-thiophene-2-carbonyl)-amino]-propionic acid methyl ester and (S)-2-[3-(5-Chloro-1-methyl-2-oxo-1,2-dihydro-pyridin-3-yl)-2-methoxy-benzenesulfo-nyl-amino]-3-[(5-chloro-thiophene-2-carbonyl)-amino]-propionic acid methyl ester (Mixture of Intermediates 71a and 71b)

The mixture of intermediates obtained in step 21.6) (1.28 g, 3.68 mmol) was converted to the title compounds as described in procedure 3.3. The mixture was evaporated under reduced pressure and purified by chromatography on silica gel; elution with DCM/pentane from 0 to 10% DCM. The intermediates were used as a 2:3 mixture (71a/71b) in the next step.

21.8) (S)-2-[3-(1-methyl-2-oxo-1,2-dihydro-pyridin-3-yl)-2-methoxy-benzenesulfonyl-amino]-3-[(5-chloro-thiophene-2-carbonyl)-amino]-propionic acid and (S)-2-[3-(5-Chloro-1-methyl-2-oxo-1,2-dihydro-pyridin-3-yl)-2-methoxy-benzenesulfonylamino]-3-[(5-chloro-thiophene-2-carbonyl)-amino]-propionic acid (Mixture of Intermediate 72a and 72b)

The mixture of intermediates obtained in 21.7) (1.31 g, 2.28 mmol) was dissolved in 20 ml of dioxane and then aqueous NaOH (1 N) (4.57 ml, 4.57 mmol) was added. After 2 h stirring at RT aq.HCl (1N) (9 ml) was added, solvents were evaporated and ethyl acetate and n-butanol were added. The organic layer was dried with $Na_2SO_4$, filtered and evaporated to dryness. The solid was triturated with diisopropyl ether and filtered. Yield: 1.28 g (100%), crude product. The intermediates were used as a 2:3 mixture (72a/72b) in the next step.

21.9) 5-Chloro-thiophene-2-carboxylic acid [(S)-2-[3-(5-chloro-1-methyl-2-oxo-1,2-dihydro-pyridin-3-yl)-2-methoxy-benzenesulfonylamino]-3-(4-cyclo-propyl-piperazin-1-yl)-3-oxo-propyl]-amide hydro chloride The mixture obtained in 21.8 (400 mg, 0.71 mmol) was dissolved in 20 ml DCM and N-cyclopropyl piperazine (278 mg, 0.79 mmol) was added followed by DIPEA (0.56 ml, 3.21 mmol) and TBTU (252 mg, 0.79 mmol). After 16 h stirring at RT the solution was evaporated to dryness and purified by silica gel chromatography (Elution with DCM/methanol from 0 to 10% of methanol). The two solid fractions obtained after evaporation of the solvents were separately dissolved in DCM, then HCl (2 M) in $Et_2O$ (5 ml) was added and the solvents were evaporated yielding colorless powders.

Yield: 302 mg, 60%. (title compound), MS (ES$^+$): m/e=668.

and 94 mg, 20% (5-Chloro-thiophene-2-carboxylic acid [(S)-2-[3-(1-methyl-2-oxo-1,2-dihydro-pyridin-3-yl)-2-methoxy-benzenesulfonylamino]-3-(4-cyclopropyl-piperazin-1-yl)-3-oxo-propyl]-amide hydro chloride).

Example 22

5-Chloro-thiophene-2-carboxylic acid [(S)-3-(4-cy-clopropyl-piperazin-1-yl)-2-(2-methyl-3-pyridin-3-yl-benzenesulfonylamino)-3-oxo-propyl]-amide dihydro chloride 22.1) 3-(3-Bromo-2-methyl-phenyl)-pyridine (Intermediate 73)

(3-Bromo-2-methylphenyl)boronic acid (3 g, 13.96 mmol) and 3-bromopyridine (2.69 ml, 27.92 mmol) in toluene (24 ml) were stirred under argon, then $Na_2CO_3$ (5.18 g, 48.86 mmol) and $Pd(PPh_3)_4$ (161 mg, 0.14 mmol) were added and the reaction was heated to 110° C. for 48 h. The solvent was evaporated and after addition of ethyl acetate the organic layer was filtered through Celite, then washed with water and dried with $Na_2SO_4$, evaporated to dryness and the product was obtained and used without further purification in step 22.2. Yield: 3.01 g, 87

22.2) 3-(3-Benzylsulfanyl-2-methyl-phenyl)-pyridine (Intermediate 74)

Intermediate 73 (3 g, 12.09 mmol) in dioxane (50 ml) was stirred under argon, then DIPEA (3.82 ml, 24.18 mmol), xantphos (0.42 g, 0.73 mmol) and $Pd_2(dba)_3$ (0.33 g, 0.36 mmol) were added and the reaction was heated to 100° C. Phenyl-methanethiol (1.56 ml, 13.3 mmol) was slowly added and the reaction stirred for 16 h. The reaction was quenched by addition of 150 ml of $H_2O$. After extraction (three times) with ethyl acetate the combined organic layers were washed with water, dried with $Na_2SO_4$, evaporated to dryness and the compound was obtained and used without further purification in step 22.3.

22.3) 2-Methyl-3-pyridin-3-yl-benzenesulfonyl chloride (Intermediate 75)

Intermediate 74 (1.33 g, 3.19 mmol) was dissolved in 20 ml DCM and treated with water (0.23 ml, 12.76 mmol), AcOH (0.91 ml, 15.95 mmol) and $SO_2Cl_2$ (1.03 ml, 12.76 mmol) at 0° C. After stirring for 5 min at 0° C. and 20 min at RT the reaction was cooled back to 0° C. and quenched by the addition of 10 ml of water. The aqueous solution was extracted with DCM (three times) and the combined organic layers were washed with cold water. Drying over $Na_2SO_4$ and evaporation to dryness yielded 1.3 g of crude intermediate 75 which was used without further purification in the next step.

22.4) (S)-2-tert-Butoxycarbonylamino-3-[(5-chloro-thiophene-2-carbonyl)-amino]-propionic acid methyl ester (Intermediate 8)

Commercially available (S)-3-amino-2-tert-butoxycarbo-nylamino-propionic acid (BOC-Dap-OH) (18.09 g, 88.56 mmol) was suspended in 100 ml DCM with N-hydroxysuccinimide (16.99 g, 147.61 mmol) and N,N'-diisopropyl-carbodiimide (11.43 ml, 73.8 mmol), then 5-Chloro-thiophene-2-carboxylic acid (12 g, 73.8 mmol) and DIPEA (25.51 ml, 147.61 mmol) in 60 ml DCM were slowly added. The mixture was stirred at RT for 2 h, then cooled to 0° C. and TMS-diazomethane was slowly added. The reaction was stirred for 2 h at RT, HCl solution (0.5 M) was added and the organic layer was separated, washed with $H_2O$, dried with $Na_2SO_4$, filtered and evaporated to dryness. The resulting solid was triturated 16 h with diisopropyl ether, filtered and washed with diisopropyl ether and dried under vacuum at 60° C. 24.4 g of crude product were obtained and used without further purification.

22.5) (S)-2-Amino-3-[(5-chloro-thiophene-2-carbonyl)-amino]-propionic acid methyl ester hydro chloride (Intermediate 76)

33 g (110.24 mmol) of intermediate 8 from step 22.4) were dissolved in 600 ml ethyl acetate and 250 ml HCl (2N in diethyl ether) was added. After 20 h stirring at RT the reaction was filtered and the solid dried under reduced pressure.

22.6) (S)-3-[(5-Chloro-thiophene-2-carbonyl)-amino]-2-(2-methyl-3-pyridin-3-yl-benzenesulfonylamino)-propionic acid methyl ester (Intermediate 77)

Intermediate 75 (0.85 g, 3.17 mmol) was dissolved in 10 ml DCM and TEA (1.55 ml, 11.11 mmol). Intermediate 76 (876 mg, 3.33 mmol) in 10 ml DCM was slowly added at 0° C. and the reaction was stirred for 16 h. After that the solution was evaporated to dryness and purified by silica gel chromatography (cyclohexane/AcOEt from 0% to 100% AcOEt). Yield: 589 mg, 38%

22.7) (S)-3-[(5-Chloro-thiophene-2-carbonyl)-amino]-2-(2-methyl-3-pyridin-3-yl-benzenesulfonylamino)-propionic acid (Intermediate 78)

Intermediate 77 (589 mg, 1.19 mmol) was dissolved in 20 ml THF and sodium hydroxide (1N aq solution) (2.38 ml, 2.38 mmol) was added. After stirring at RT for 2 h, HCl 1 N (2 ml) was added, solvents were evaporated and DCM was added. The organic layer was dried with $Na_2SO_4$, filtered and evaporated to dryness. The solid was triturated with diisopropyl ether and filtrated. 550 mg (yield: 96%) of crude product were obtained and used without further purification in the next step.

22.8) 5-Chloro-thiophene-2-carboxylic acid [(S)-3-(4-cyclopropyl-piperazin-1-yl)-2-(2-methyl-3-pyridin-3-yl-benzenesulfonylamino)-3-oxo-propyl]-amide dihydrochloride Intermediate 78 (202 mg, 0.42 mmol) was dissolved in 10 ml DCM and N-cyclopropyl piperazine (105 mg, 0.84 mmol) was added followed by DIPEA (0.29 ml, 1.68 mmol) and TBTU (202 mg, 0.63 mmol). After stirring for 1 h at RT the solution was evaporated to dryness and purified by silica gel chromatography (Elution with DCM/methanol from 0 to 10% of methanol). The solid obtained after evaporation of the solvents was dissolved in DCM, HCl 2M in $Et_2O$ (5 ml) was added and the solvents were evaporated. Yield: 163 mg, 59%. MS ($ES^+$): m/e=588.

Example 23

5-Chloro-thiophene-2-carboxylic acid [(S)-3-(4-cyclopropyl-piperazin-1-yl)-2-(2-methoxy-3-pyridin-4-yl-benzenesulfonylamino)-3-oxo-propyl]-amide hydrochloride 23.1) 4-(3-Benzylsulfanyl-2-methoxy-phenyl)-pyridine (Intermediate 79)

Pyridin-4-yl boronic acid (3.85 g, 18.77 mmol), intermediate 67 (5.81 g, 18.77 mmol) and $Ba(OH)_2*8H_2O$ (11.84 g, 37.55 mmol) in water (4.06 ml) and DMSO (37 ml) were stirred for 15 min under argon at RT. Then $PdCl_2(dppf)$ (0.69 g, 0.94 mmol) was added and the mixture was heated at 110° C. for 6 h. After cooling to RT the mixture was diluted with ethyl acetate (200 ml), washed with water (2×300 ml) and brine (200 ml), dried over $Na_2SO_4$ and evaporated to dryness. The crude product was purified by silica gel chromatography. Elution with cyclohexane/ethyl acetate from 0 to 20% of ethyl acetate gave 2.73 g, yield=47%.

23.2) 2-Methoxy-3-pyridin-4-yl-benzenesulfonyl chloride (Intermediate 80)

Intermediate 79 (2.28 g, 7.42 mmol) was dissolved in 20 ml DCM and treated with water (0.53 ml, 29.67 mmol), AcOH (2.12 ml, 37.08 mmol) and $SO_2Cl_2$ (2.4 ml, 29.67 mmol) at 0° C. After stirring for 5 min at 0° C. and 20 min at RT the reaction was cooled back to 0° C. and quenched by the addition of water (10 ml). The aqueous solution was extracted with DCM (3×) and the combined organic layers were washed with cold water. Drying over $Na_2SO_4$ and evaporation to dryness yielded 2.3 g (yield 92%) of crude intermediate 80 which was used without further purification in the next step.

23.3) (S)-3-[(5-Chloro-thiophene-2-carbonyl)-amino]-2-(2-methoxy-3-pyridin-4-yl-benzenesulfonylamino)-propionic acid methyl ester (Intermediate 81)

Intermediate 80 (1.2 g, 4.25 mmol) was converted to intermediate 81 as described in procedure 3.3). The mixture was evaporated under reduced pressure and purified by chromatography on silica gel, elution with DCM/pentane from 0 to 10% of DCM. The intermediate was used directly in the next step.

23.4) (S)-3-[(5-Chloro-thiophene-2-carbonyl)-amino]-2-(2-methoxy-3-pyridin-4-yl-benzenesulfonylamino)-propionic acid (Intermediate 82)

Intermediate 81 (1.08 g, 2.12 mmol) was dissolved in 20 ml of THF and sodium hydroxide (1 N water solution) (4.24 ml, 4.24 mmol) was added. After 16 h stirring at RT 1 N HCl (9 ml) was added, solvents were evaporated and n-butanol was added. The organic layer was dried with $Na_2SO_4$, filtered and evaporated to dryness. 1.05 g (yield: 99%) of crude product. The intermediate was directly used in the next step.

23.5) 5-Chloro-thiophene-2-carboxylic acid [(S)-3-(4-cyclopropyl-piperazin-1-yl)-2-(2-methoxy-3-pyridin-4-yl-benzenesulfonylamino)-3-oxo-propyl]-amide hydrochloride Intermediate 82 (170 mg, 0.34 mmol) was dissolved in 10 ml DCM and N-cyclopropyl piperazine (134 mg, 0.38 mmol)

was added followed by DIPEA (0.27 ml, 1.54 mmol) and TBTU (121 mg, 0.38 mmol). After 16 h stirring at RT, the solution was evaporated to dryness and purified by silica gel chromatography (Elution with DCM/methanol from 0 to 10% of methanol). The solid obtained after evaporation of the solvents was dissolved in DCM, HCl 2M in Et$_2$O (5 ml) was added and the solvents were evaporated yielding a white powder. Yield: 112 mg, 50% MS (ES$^+$): m/e=604.

Example 24

5-Chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]-amide hydrochloride 24.1) 1-Benzylsulfanyl-3-bromo-2-methyl-benzene (Intermediate 83)

2,6-dibromotoluene (20 g, 100 mmol) in dioxane (160 ml) was stirred under argon. Then, DIPEA (30.9 ml, 160 mmol), xantphos (2.77 g, 4.8 mmol) and Pd$_2$(dba)$_3$ (2.4 g, 2.4 mmol) were added and the reaction was heated to 100° C. Phenylmethanethiol (9.4 ml, 80 mmol) was slowly added and the reaction stirred for 6 h. The reaction was quenched by the addition of 150 ml of H$_2$O. After extraction (three times) with ethyl acetate, the combined organic layers were washed with water, dried with Na$_2$SO$_4$, evaporated to dryness and the product was purified by silica gel chromatography.
Yield: 17 g, 72%

24.2) 1-(3-Benzylsulfanyl-2-methyl-phenyl)-pyrrolidin-2-one (Intermediate 84)

Intermediate 83 (7 g, 23.87 mmol), pyrrolidin-2-one (4.06 g, 47.74 mmol), CuI (909 mg, 4.77 mmol), N,N'-dimethylethylene diamine (10.28 ml, 95.49 mmol) and K$_2$CO$_3$ (7.25 g, 52.52 mmol) were suspended in toluene (10 ml) under N$_2$ and heated to 110° C. for 16 h. After cooling to RT the reaction mixture was quenched by the addition of 100 ml water and extracted with ethyl acetate (three times). The organic layers were combined and washed with water and sat. aq NaCl-solution, dried with Na$_2$SO$_4$, filtered and evaporated to dryness, and purified by silica gel chromatography.
Yield: 6.55 g, 91

24.3) 2-Methyl-3-(pyrrolidin-2-one)-benzenesulfonyl chloride (Intermediate 85)

Intermediate 84 (6.52 g, 21.93 mmol) was dissolved in 22 ml DCM and treated with water (1.58 ml, 87.71 mmol), AcOH (6.27 ml, 109.64 mmol) and SO$_2$Cl$_2$ (7.11 ml, 87.71 mmol) at 0° C. After stirring for 5 min at 0° C. and 20 min at RT the reaction was cooled back to 0° C. and quenched by the addition of 10 ml of water. The aqueous solution was extracted with DCM (three times) and the combined organic layers were washed with cold water. Drying over Na$_2$SO$_4$ and evaporation to dryness yielded crude intermediate 85 which was used without further purification in the next step.

24.4) (S)-3-[(5-Chloro-thiophene-2-carbonyl)-amino]-2-[2-methyl-3-(2-oxo-pyrrolidin-1-yl)-benzenesulfonylamino]-propionic acid methyl ester (Intermediate 86)

Intermediate 76 (3.46 g, 11.59 mmol) was dissolved in 25 ml DCM and TEA (8.49 ml, 61.03 mmol). Intermediate 85 (3.34 g, 12.21 mmol) in 20 ml DCM was slowly added at 0° C. and the reaction was stirred for 16 h. Then the solution was evaporated to dryness and purified by silica gel chromatography. Yield: 5.69 g, 93

24.5) (S)-3-[(5-Chloro-thiophene-2-carbonyl)-amino]-2-[2-methyl-3-(2-oxo-pyrrolidin-1-yl)-benzenesulfonylamino]-propionic acid (Intermediate 87)

Intermediate 86 was dissolved in 20 ml THF and sodium hydroxide (1N water solution) (38.16 ml, 38.16 mmol) was added. After 2 h stirring at RT the reaction mixture was extracted with diethyl ether and 1 N HCl (38.16 ml, 38.16 mmol) was added to the aqueous layer. The aqueous layer was extracted with n-butanol. The organic layer was dried with Na$_2$SO$_4$, filtered and evaporated to dryness. 8.28 g of crude product were obtained and used without further purification in step 24.6.

24.6) 5-Chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]-amide hydro chloride Intermediate 87 (802 mg, 1.65 mmol) was dissolved in 10 ml DCM and N-methyl piperazine (0.73 ml, 6.60 mmol) was added followed by DIPEA (0.55 ml, 3.3 mmol) and TBTU (636 mg, 1.98 mmol). After 1 h stirring at RT the solution was evaporated to dryness and purified by silica gel chromatography. The compound was dissolved in DCM, HCl (2 M in diethyl ether (5 ml)) was added and the solvents were evaporated yielding a white powder. Yield: 651 mg, 70%. MS (ES$^+$): m/e=568.

Example 25

5-Chloro-thiophene-2-carboxylic acid {(S)-3-(4-methyl-piperazin-1-yl)-2-[4-(2-methyl-thiazol-4-yl)-benzenesulfonylamino]-3-oxo-propyl}-amide hydro chloride 25.1) (S)-2-tert-Butoxycarbonylamino-3-[(5-chloro-thiophene-2-carbonyl)-amino]-propionic acid (Intermediate 88)

Intermediate 8 (15 g, 41.34 mmol) was dissolved in 800 ml THF and sodium hydroxide (1 N water solution) (82.68 ml, 82.68 mmol) was added. After 5 h stirring at RT the reaction mixture was extracted with DCM and washed with HCl (0.2M), water and brine. The organic layer was dried with Na$_2$SO$_4$, filtered and evaporated to dryness. 13.4 g (yield=93%) of crude product were obtained and used without further purification in the next step.

25.2) [(S)-1-{[(5-Chloro-thiophene-2-carbonyl)-amino]-methyl}-2-(4-methyl-piperazin-1-yl)-2-oxo-ethyl]-carbamic acid tert-butyl ester (Intermediate 89)

Intermediate 88 (13.4 g, 38.42 mmol) was dissolved in 200 ml DCM and N-methyl piperazine (8.52 ml, 76.83 mmol) was added followed by DIPEA (26.77 ml, 153.67 mmol) and TBTU (18.5 g, 57.63 mmol). After 16 h stirring at RT, the solution was evaporated to dryness and purified by silica gel chromatography. Yield: 13.05 g, 79%.

25.3) (5-Chloro-thiophene-2-carboxylic acid [(S)-2-amino-3-(4-methyl-piperazin-1-yl)-3-oxo-propyl]-amide dihydrochloride (Intermediate 90)

13.05 g (30.28 mmol) of intermediate 89 were dissolved in 300 ml ethyl acetate and 60 ml HCl (2 N in diethyl ether) was added. After 5 h stirring at RT the reaction was filtered and the solid dried under reduced pressure. Yield=9.78 g, 80%, colorless powder.

25.4) 5-Chloro-thiophene-2-carboxylic acid {(S)-3-(4-methyl-piperazin-1-yl)-2-[4-(2-methyl-thiazol-4-yl)-benzenesulfonylamino]-3-oxo-propyl}-amide hydrochloride Intermediate 90 (0.2 g, 0.5 mmol) was dissolved in 10 ml DCM and TEA (0.35 ml, 2.5 mmol). Commercially available 4-(2-Methyl-thiazol-4-yl)-benzenesulfonyl chloride (130 mg, 0.47 mmol) in 5 ml DCM was slowly added at 0° C. and the reaction was stirred for 16 h. Then the solution was evaporated to dryness and purified by silica gel chromatography. The compound was dissolved in DCM, HCl (2 M in diethyl ether (500 ml)) was added and the solvents were evaporated to dryness.
Yield: 175.7 mg, 58%, colorless solid. MS (ES$^+$): m/e=568.

Example 26

5-Chloro-thiophene-2-carboxylic acid [(S)-2-[3-(5-methyl-[1,3,4]oxadiazol-2-yl)-benzenesulfonylamino]-3-(4-methyl-piperazin-1-yl)-3-oxo-propyl]-amide Intermediate 90 (0.2 g, 0.5 mmol) and the commercially available sulfonyl chloride (0.122 g, 0.47 mmol) were coupled in close analogy to the procedure described in 25.4).
Yield: 105 mg, 39%, colorless solid. MS (ES$^+$): m/e=553.

Example 27

5-Chloro-thiophene-2-carboxylic acid [(S)-2-[3-(5-methyl-[1,2,4]oxadiazol-3-yl)-benzenesulfonylamino]-3-(4-methyl-piperazin-1-yl)-3-oxo-propyl]-amide hydro chloride Intermediate 90 (0.202 g, 0.5 mmol) and the commercially available sulfonyl chloride (0.122 g, 0.47 mmol) were coupled in close analogy to the procedure described in 25.4).
Yield: 220.7 mg, 76%, colorless solid. MS (ES$^+$): m/e=553.

Example 28

5-Chloro-thiophene-2-carboxylic acid [(S)-2-[2-methyl-3-(2-oxo-pyrrolidin-1-yl)-benzenesulfonylamino]-3-(4-methyl-4-oxy-piperazin-1-yl)-3-oxo-propyl]-amide hydrochloride 5-Chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]-amide hydro chloride (156 mg, 0.27 mmol) was dissolved in 2 ml DCM and m-CPBA (92.3 mg, 0.41 mmol) was added. After 30 min stirring at RT, HCl (2M solution in diethyl ether was added (excess). The colorless solid was filtered.
Yield: 105 mg, 66%. MS (ES$^+$): m/e=584.

Example 29

5-Chloro-thiophene-2-carboxylic acid [(S)-3-(4-methyl-piperazin-1-yl)-2-(2-methyl-3-pyrazol-1-yl-benzenesulfonylamino)-3-oxo-propyl]-amide hydro chloride

29.1) 2-Methyl-3-bromo-benzenesulfonyl chloride (Intermediate 91)

Intermediate 83 (3.5 g, 11.94 mmol) was dissolved in 100 ml DCM and treated with water (0.86 ml, 47.74 mmol), AcOH (3.41 ml, 59.68 mmol) and SO$_2$Cl$_2$ (3.87 ml, 47.74 mmol) at 0° C. After stirring for 5 min at 0° C. and 20 min at RT the reaction was cooled back to 0° C. and quenched by the addition of 10 ml of water. The aqueous solution was extracted with DCM (three times) and the combined organic layers were washed with cold water. Drying over Na$_2$SO$_4$ and evaporation to dryness yielded 3.2 g of crude intermediate which was used without further purification in the next step.

29.2) 5-Chloro-thiophene-2-carboxylic acid [(S)-3-(4-methyl-piperazin-1-yl)-2-(2-methyl-3-bromo-1-yl-benzenesulfonylamino)-3-oxo-propyl]-amide (Intermediate 92)

Intermediate 90 (5 g, 12.38 mmol) was dissolved in 50 ml DCM and TEA (6.03 ml, 43.34 mmol). Intermediate 91 (3.17 g, 11.76 mmol) in 20 ml DCM was slowly added at 0° C. and the reaction was stirred for 16 h. The solution was then evaporated to dryness and purified by silica gel chromatography.
Yield: 5.6 g, 80

29.3) 5-Chloro-thiophene-2-carboxylic acid [(S)-3-(4-methyl-piperazin-1-yl)-2-(2-methyl-3-pyrazol-1-yl-benzenesulfonylamino)-3-oxo-propyl]-amide hydro chloride Intermediate 92 (0.5 g, 0.89 mmol), pyrazole (54.3 mg, 0.8 mmol), CuI (16.9 mg, 0.09 mmol), L-prolinol (20 µl, 0.18 mmol) and K$_2$CO$_3$ (0.245 g, 1.77 mmol) were suspended in DMSO (10 ml) under N$_2$ in a sealed tube and heated to 140° C. for 2 d. After cooling to RT the reaction mixture was quenched by the addition of 100 ml of water and extracted with ethyl acetate (three times). The organic layers were combined and washed with water and sat. aq NaCl-solution, dried with Na$_2$SO$_4$, filtered and evaporated to dryness and purified by chromatography on silica gel. The compound was dissolved in DCM, HCl (2 M in Et$_2$O (5 ml)) was added and solvents were evaporated yielding a colorless powder.
Yield: 25 mg, 5% MS (ES$^+$): m/e=551.

Example 30

5-Chloro-thiophene-2-carboxylic acid [(S)-2-[2,6-difluoro-3-(2-oxo-pyrrolidin-1-yl)-benzenesulfonylamino]-3-(4-methyl-piperazin-1-yl)-3-oxo-propyl]-amide hydrochloride

30.1) 1-(3-Bromo-2,4-difluoro-phenyl)-pyrrolidin-2-one (Intermediate 93)

1,3-dibromo-2,4-difluoro-benzene (5 g, 18.5 mmol) and pyrrolidin-2-one (1.56 g, 18.5 mmol) in dioxane (160 ml) were stirred under argon. Cs$_2$CO$_3$ (7.19 g, 22 mmol), xantphos (1.27 g, 2 mmol) and Pd$_2$(dba)$_3$ (0.675 g, 0.5 mmol) were added and the reaction was heated to 85° C. for 16 h. The reaction was quenched by the addition of 150 ml of H$_2$O. After extraction with ethyl acetate (three times), the combined organic layers were washed with water, dried with Na$_2$SO$_4$, evaporated to dryness and the product was purified by silica gel chromatography (ethyl acetate/cyclohexane 0 to 20% ethyl acetate). Yield: 1 g, 20

30.2) 1-(3-Benzylsulfanyl-2,4-difluoro-phenyl)-pyrrolidin-2-one (Intermediate 94)

Intermediate 93 (1 g, 3.62 mmol) in dioxane (30 ml) was stirred under argon. DIPEA (1.26 ml, 7.24 mmol), xantphos (0.126 g, 0.22 mmol) and Pd$_2$(dba)$_3$ (0.099 g, 0.11 mmol) were added and the reaction was heated to 100° C. Phenyl-methanethiol (0.41 ml, 3.44 mmol) was slowly added and the reaction stirred for 3 h. The reaction was quenched by the addition of 150 ml of H$_2$O. After extraction with ethyl acetate (three times), the combined organic layers were washed with water, dried with Na$_2$SO$_4$, evaporated to dryness and the product was purified by silica gel chromatography.
Yield: 0.5 g, 30

30.3) 2,6-difluoro-3-(pyrrolidin-2-one)-benzenesulfonyl chloride (Intermediate 95)

Intermediate 94 (0.5 g, 1.57 mmol) was dissolved in 22 ml DCM and treated with water (0.11 ml, 6.26 mmol), AcOH (0.45 ml, 7.83 mmol) and SO$_2$Cl$_2$ (0.51 ml, 6.26 mmol) at 0° C. After stirring for 5 min at 0° C. and 20 min at RT the reaction was cooled back to 0° C. and quenched by the addition of 10 ml of water. The aqueous solution was extracted with DCM (three times) and the combined organic layers were washed with cold water, dried over Na$_2$SO$_4$ and evaporated to dryness. The crude intermediate was used without further purification in the next step.

30.4) 5-Chloro-thiophene-2-carboxylic acid [(S)-2-[2,6-difluoro-3-(2-oxo-pyrrolidin-1-yl)-benzenesulfonylamino]-3-(4-methyl-piperazin-1-yl)-3-oxo-propyl]-amide hydro chloride Intermediate 90 (0.666 g, 1.65 mmol) was dissolved in 20 ml DCM and TEA (0.8 ml, 5.77 mmol). Intermediate 95 (0.463 mg, 1.57 mmol) in 5 ml DCM was slowly added at 0° C. and the reaction was stirred for 16 h. After that the solution was evaporated to dryness and purified by silica gel chromatography. The compound was dissolved in DCM, HCl (2M in diethyl ether (5 ml)) was added and the solvents were evaporated to dryness. Yield: 231 mg, 23%, colorless solid. MS (ES$^+$): m/e=590.

Example 31

5-Chloro-thiophene-2-carboxylic acid [(S)-2-[2-fluoro-3-(2-oxo-pyrrolidin-1-yl)-benzenesulfonylamino]-3-(4-methyl-piperazin-1-yl)-3-oxo-propyl]-amide hydro chloride

31.1) 3-Bromo-2-fluoro-phenylamine (Intermediate 96)

1-Bromo-2-fluoro-3-nitro-benzene (3 g, 13.64 mmol), iron (2.28 g, 40.91 mmol), water (34.39 ml, 1909 mmol) and acetic acid (11.7 ml, 204.55 mmol) were added to ethanol (60 ml) and heated to reflux for 2 h. The reaction mixture was then filtered through Celite and evaporated. Water was added and the solution was made basic by the addition of 2 N NaOH, followed by extraction with DCM. The organic layers were washed with water and brine, dried with Na$_2$SO$_4$ evaporated to dryness and the crude product was obtained and used without further purification. Yield: 1.46 g, 56%

31.2) N-(3-Bromo-2-fluoro-phenyl)-4-chloro-butyramide (Intermediate 97)

To a solution of intermediate 96 (1.45 g, 7.66 mmol) and Na$_2$HPO$_4$ (2.17 g, 15.33 mmol) in CHCl$_3$ (15 ml) was slowly added 4-chlorobutyryl chloride (1.08 g, 7.66 mmol) at RT. The reaction was stirred for 16 h, quenched with water and extracted with DCM. The organic layers were washed with water and brine, dried with Na$_2$SO$_4$, filtered and evaporated to dryness. The yellow powder was triturated with diisopropyl ether and filtered. Yield: 1.81 g, 80% (colorless solid)

31.3) 1-(3-Bromo-2-fluoro-phenyl)-pyrrolidin-2-one (Intermediate 98)

Sodium (1.1 g, 47.93 mmol) was added to ethanol (20 ml) at RT. After complete conversion, intermediate 97 in ethanol (20 ml) was slowly added and the reaction was stirred for 30 min. The reaction mixture was neutralized with conc. HCl and evaporated to dryness. Water (100 ml) was added and the aqueous layer extracted with ethyl acetate (three times). The organic layers were combined and washed with water and sat. aq NaHCO$_3$-solution, dried with Na$_2$SO$_4$ evaporated to dryness and the crude product was obtained and used without further purification.
Yield: 1.48 g, 93% (colorless solid).

31.4) 1-(3-Benzylsulfanyl-2-fluoro-phenyl)-pyrrolidin-2-one (Intermediate 99)

Intermediate 98 (1.48 g, 5.73 mmol) in dioxane (50 ml) was stirred under argon. DIPEA (2 ml, 11.47 mmol), xantphos (0.2 g, 0.34 mmol) and Pd$_2$(dba)$_3$ (0.157 g, 0.17 mmol) were added and the reaction was heated to 100° C. Phenyl-methanethiol (0.64 ml, 5.45 mmol) was slowly added and the reaction stirred for 1 h. The reaction was quenched by the addition of 50 ml of H$_2$O. After extraction with ethyl acetate (three times) the combined organic layers were washed with water, dried with Na$_2$SO$_4$, evaporated to dryness and the product was purified by silica gel chromatography.
Yield: 0.97 g, 56%.

31.5) 2-fluoro-3-(pyrrolidin-2-one)-benzenesulfonyl chloride (Intermediate 100)

Intermediate 99 (0.3 g, 1 mmol) was dissolved in 10 ml DCM and treated with water (0.07 ml, 3.98 mmol), AcOH (0.28 ml, 4.98 mmol) and SO$_2$Cl$_2$ (0.32 ml, 3.98 mmol) at 0° C. After stirring for 5 min at 0° C. and 20 min at RT the reaction was cooled back to 0° C. and quenched by the addition of 10 ml of water. The aqueous solution was extracted with DCM (three times) and the combined organic layers were washed with cold water, dried over Na$_2$SO$_4$ and evaporated to dryness. The crude intermediate was used without further purification in the next step.

31.6) 5-Chloro-thiophene-2-carboxylic acid [(S)-2-[2-fluoro-3-(2-oxo-pyrrolidin-1-yl)-benzenesulfonylamino]-3-(4-methyl-piperazin-1-yl)-3-oxo-propyl]-amide hydro chloride Intermediate 90 (0.42 g, 1.04 mmol) was dissolved in 10 ml DCM and TEA (0.51 ml, 3.64 mmol). Intermediate 100

(0.274 g, 0.99 mmol) in 5 ml DCM was slowly added at 0° C. and the reaction was stirred for 16 h. After that the solution was evaporated to dryness and purified by silica gel chromatography. The compound was dissolved in DCM, HCl (2M in diethyl ether (500 ml)) was added and the solvents were evaporated to dryness. Yield: 0.429 g, 68%, colorless solid. MS (ES$^+$): m/e=572.

Example 32

5-Chloro-thiophene-3-carboxylic acid [(S)-3-(4-difluoromethylene-piperidin-1-yl)-2-(2-methyl-3-pyridin-2-yl-benzenesulfonylamino)-3-oxo-propyl]-amide hydrochloride 32.1) 2-(3-Bromo-2-methyl-phenyl)-pyridine (Intermediate 101)

A solution of i-PrMgCl (27.49 mL, 2M in THF, 55 mmol.) was added dropwise to commercially available 1,3-dibromo-2-methyl-benzene (12.5 g, 50 mmol) at RT under argon and then heated at 65° C. for 1.5 h. The mixture was added via syringe to a suspension of dry ZnCl$_2$ (6.83 g, 50 mmol.) in dry THF (20 ml) and cooled to 0° C. under argon. The resulting suspension was stirred at RT for 30 min. Then 2-bromopyridine (4.78 ml, 50 mmol.) and PdCl$_2$*dppf (2.03 g) were added and the mixture was refluxed for 2 h. The reaction mixture was then quenched by the addition of a 5% solution of citric acid (200 ml) and extracted with ethyl acetate (2×250 ml). The combined organic layers were consecutively washed with a 5% solution of citric acid (150 ml) and brine (150 ml), dried over Na$_2$SO$_4$, filtered and evaporated under reduced pressure. The crude material was chromatographed on silica gel. Yield: 7.7 g, 78%.

32.2) 2-(3-Benzylsulfanyl-2-methyl-phenyl)-pyridine (Intermediate 102)

A mixture of intermediate 101 (15.0 g, 60.53 mmol), n-tributylstannyl-sulfanylmethyl-benzene (27.5 g, 66.6 mmol) (as described in J. Org. Chem. 1984, 5206), KF (5.3 g, 90.8 mmol) and Xantphos (1.05 g, 1.82 mmol) in dry NMP (30 ml) were stirred for 15 min under argon at RT. Then, Pd$_2$dba$_3$ (1.66 g, 1.82 mmol.) was added and the mixture was heated for 10 h at 100° C. After cooling to RT the reaction mixture was treated with a 5% solution of KF (100 mL) for 15 min under stirring and was then diluted with ethyl acetate (200 ml) and filtered over Celite 545. The organic layers were consecutively washed with water (2×200 ml) and brine (100 ml), dried over Na$_2$SO$_4$ and evaporated under reduced pressure. The crude mixture was chromatographed on silica gel. Elution with ethyl acetate/cyclohexane from 0 to 20% of ethyl acetate gave 7.7 g of intermediate 102 as a colorless oil, yield=78%.

32.3) 2-Methyl-3-pyridin-2-yl-benzenesulfonyl chloride (Intermediate 103)

Intermediate 102 (2.33 g, 8 mmol.) was converted to intermediate 103 as described in procedure 1.7. The crude material was diluted with ethyl acetate (100 ml) and washed with a 1% solution of NaHCO$_3$ (50 ml), water (50 ml) and brine (50 mL), dried over Na$_2$SO$_4$, and evaporated under reduced pressure. The crude material was quickly chromatographed on silica gel. Elution with ether/pentane from 0 to 100% of ether gave 0.95 g of intermediate 103 as a colorless oil, yield=44%.

32.4) (S)-2-tert-Butoxycarbonylamino-3-[(5-chloro-thiophene-3-carbonyl)-amino]-propionic acid (Intermediate 104)

A solution of (S)-3-Amino-2-tert-butoxycarbonylamino-propionic acid (1.72 g, 9.5 mmol) in THF (5 ml) was added dropwise under vigorous stirring to a mixture of 5-chloro-thiophene-3-carbonyl chloride (1.94 g, 9.5 mmol) in 1N aq. NaOH (10 ml). After 2 h the reaction mixture was extracted with ethyl acetate (200 ml), washed with 1 N aq HCl (30 ml) and brine (100 ml), dried over Na$_2$SO$_4$ and evaporated under reduced pressure. One obtained 1.8 g of intermediate 104 as amorphous solid which was used in the next step without further purification.

32.5) [(S)-1-{[(5-Chloro-thiophene-3-carbonyl)-amino]-methyl}-2-(4-difluoromethylene-piperidin-1-yl)-2-oxo-ethyl]-carbamic acid tert-butyl ester (Intermediate 105)

Intermediate 104 (1.74 g, 4.99 mmol) was converted to intermediate 105 similar to the procedure described in 1.2) using 4-difluoromethylene-piperidine (0.93 g, 5.49 mmol.) as described in PCT Int. Appl. 2005009943 and DIPEA (2.62 ml, 14.97 mmol) in DCM (16 ml). TBTU was used instead of HATU as coupling reagent. The crude material was chromatographed on silica gel. Elution with MeOH/DCM from 0 to 10% of MeOH gave 1.5 g of intermediate 105 as an amorphous solid, yield=65%.

32.6) 5-Chloro-thiophene-3-carboxylic acid [(S)-3-(4-difluoromethylene-piperidin-1-yl)-2-(2-methyl-3-pyridin-2-yl-benzenesulfonylamino)-3-oxo-propyl]-amide hydro chloride A solution of intermediate 105 (1.46 g, 3.15 mmol) in ethyl acetate (50 ml) was saturated with hydrogen chloride at 0° C. After 1 h the reaction mixture was evaporated under reduced pressure. To this material and triethyl amine (0.55 ml, 4.0 mmol) in DCM (7 ml) was added portionwise intermediate 103 (0.30 g, 1 mmol). After 3 h the reaction mixture was evaporated under reduced pressure and the crude material was purified by HPLC. Yield after lyophilization: 0.31 g, 50%. MS (ES$^+$): m/e=595, chloro pattern. According to the previous examples the following compounds were prepared in close analogy:

| Example No. | Compound Name | Mass (from LC/MS) | Rt (from LC/MS) (min) | LC/MS Method |
|---|---|---|---|---|
| 33 | 5-Chloro-thiophene-2-carboxylic acid [(S)-2-[2-chloro-3-(2-oxo-piperidin-1-yl)-benzenesulfonylamino]-3-(4-methyl-piperazin-1-yl)-3-oxo-propyl]-amide | 602 | 5.41 | T |

| Example No. | Compound Name | Mass (from LC/MS) | Rt (from LC/MS) (min) | LC/MS Method |
|---|---|---|---|---|
| 34 | 5-Chloro-thiophene-2-carboxylic acid [(S)-2-[2-ethyl-3-(2-oxo-pyrrolidin-1-yl)-benzenesulfonylamino]-3-((S)-3-methyl-morpholin-4-yl)-3-oxo-propyl]-amide | 583.08/ 585.11 | 1.49 | Q |
| 35 | 5-Chloro-thiophene-2-carboxylic acid [(S)-2-[2-ethyl-3-(5-oxo-[1,4]oxazepan-4-yl)-benzenesulfonylamino]-3-((S)-3-methyl-morpholin-4-yl)-3-oxo-propyl]-amide | 613.10/ 615.13 | 1.45 | Q |
| 36 | 5-Chloro-thiophene-2-carboxylic acid {(S)-3-((S)-3-methyl-morpholin-4-yl)-2-[2-methyl-3-(3-oxo-morpholin-4-yl)-benzenesulfonylamino]-3-oxo-propyl}-amide | 584.97/ 597.00 | 1.4 | Q |
| 37 | 5-Chloro-thiophene-2-carboxylic acid [(S)-2-[2-ethyl-3-(2-oxo-piperidin-1-yl)-benzene-sulfonylamino]-3-((S)-3-methyl-morpholin-4-yl)-3-oxo-propyl]-amide | 597.04/ 599.09 | 1.51 | Q |
| 38 | 5-Chloro-thiophene-2-carboxylic acid {(S)-2-[2-ethyl-3-(3-oxo-morpholin-4-yl)-benzenesulfonylamino]-3-morpholin-4-yl-3-oxo-propyl}-amide | 585.15/ 587.17 | 1.36 | Q |
| 39 | 5-Chloro-thiophene-2-carboxylic acid {(S)-3-((2S.6R)-2,6-dimethyl-morpholin-4-yl)-2-[2-ethyl-3-(3-oxo-morpholin-4-yl)-benzene-sulfonylamino]-3-oxo-propyl}-amide | 613.17/ 615.20 | 1.51 | Q |
| 40 | 5-Chloro-thiophene-2-carboxylic acid {(S)-3-(4,4-difluoro-piperidin-1-yl)-2-[2-ethyl-3-(3-oxo-morpholin-4-yl)-benzenesulfonyl-amino]-3-oxo-propyl}-amide | 619.15/ 621.17 | 1.61 | Q |
| 41 | 5-Chloro-thiophene-2-carboxylic acid {(S)-3-(3,3-difluoro-piperidin-1-yl)-2-[2-ethyl-3-(3-oxo-morpholin-4-yl)-benzenesulfonyl-amino]-3-oxo-propyl}-amide | 619.15/ 621.18 | 1.58 | Q |
| 42 | 5-Chloro-thiophene-2-carboxylic acid {(S)-2-[2-ethyl-3-(3-oxo-morpholin-4-yl)-benzenesulfonylamino]-3-oxo-3-piperidin-1-yl-propyl}-amide | 583.13/ 585.16 | 1.55 | Q |
| 43 | 5-Chloro-thiophene-2-carboxylic acid [(S)-2-[2-ethyl-3-(3-oxo-morpholin-4-yl)-benzenesulfonylamino]-3-(4-methoxy-piperidin-1-yl)-3-oxo-propyl]-amide | 613.15/ 615.18 | 1.45 | Q |
| 44 | 5-Chloro-thiophene-2-carboxylic acid [(S)-2-[2-ethyl-3-(3-oxo-morpholin-4-yl)-benzenesulfonylamino]-3-(4-hydroxy-piperidin-1-yl)-3-oxo-propyl]-amide | 599.25/ 601.26 | 1.28 | Q |
| 45 | 5-Chloro-thiophene-2-carboxylic acid {(S)-3-azepan-1-yl-2-[2-ethyl-3-(3-oxo-morpholin-4-yl)-benzenesulfonylamino]-3-oxo-propyl}-amide | 597.26/ 599 29 | 1.61 | Q |
| 46 | 5-Chloro-thiophene-2-carboxylic acid {(S)-2-[2-ethyl-3-(3-oxo-morpholin-4-yl)-benzenesulfonylamino]-3-[1,4]oxazepan-4-yl-3-oxo-propyl}-amide | 599.26/ 601.29 | 1.41 | Q |
| 47 | 5-Chloro-thiophene-2-carboxylic acid {(S)-2-[2-ethyl-3-(3-oxo-morpholin-4-yl)-benzenesulfonylamino]-3-(1S,4S)-2-oxa-5-aza-bicyclo[2.2.1]hept-5-yl-3-oxo-propyl}-amide | 597.28/ 599.21 | 1.65 | P |
| 48 | 5-Chloro-thiophene-2-carboxylic acid [(S)-2-[2-ethyl-3-(3-oxo-morpholin-4-yl)-benzenesulfonylamino]-3-((R)-3-hydroxy-piperidin-1-yl)-3-oxo-propyl]-amide | 599.20/ 601.23 | 1.52 | M |
| 49 | 5-Chloro-thiophene-2-carboxylic acid [(S)-2-[2-ethyl-3-(3-oxo-morpholin-4-yl)-benzenesulfonylamino]-3-((S)-3-hydroxy-piperidin-1-yl)-3-oxo-propyl]-amide | 599.27/ 601.28 | 1.5 | M |
| 50 | 5-Chloro-thiophene-2-carboxylic acid [(S)-2-[2-methoxy-3-(2-oxo-piperidin-1-yl)-benzenesulfonylamino]-3-(4-methoxy-piperidin-1-yl)-3-oxo-propyl]-amide | 613.10/ 615.13 | 1.5 | Q |
| 51 | 5-Chloro-thiophene-2-carboxylic acid {(S)-3-(4,4-difluoro-piperidin-1-yl)-2-[2-methoxy-3-(2-oxo-piperidin-1-yl)-benzenesulfonylamino]-3-oxo-propyl}-amide | 619.07/ 621.10 | 1.66 | Q |

-continued

| Example No. | Compound Name | Mass (from LC/MS) | Rt (from LC/MS) (min) | LC/MS Method |
|---|---|---|---|---|
| 52 | 5-Chloro-thiophene-2-carboxylic acid {(S)-3-azepan-1-yl-2-[2-ethyl-3-(2-oxo-piperidin-1-yl)-benzenesulfonylamino]-3-oxo-propyl}-amide | 595.14/ 597.18 | 1.7 | Q |
| 53 | 5-Chloro-thiophene-2-carboxylic acid {(S)-2[2-ethyl-3-(2-oxo-piperidin-1-yl)-benzene-sulfonylamino]-3-oxo-3-piperazin-1-yl-propyl}-amide; compound with trifluoro-acetic acid | 582.13/ 584.17 | 1.27 | Q |
| 54 | 5-Chloro-thiophene-2-carboxylic acid [(S)-2-[2-ethyl-3-(2-oxo-piperidin-1-yl)-benzene-sulfonylamino]-3-(4-methoxy-piperidin-1-yl)-3-oxo-propyl]-amide | 611.13/ 613.17 | 1.57 | Q |
| 55 | 5-Chloro-thiophene-2-carboxylic acid [(S)-2-[2-ethyl-3-(3-oxo-morpholin-4-yl)-benzenesulfonylamino]-3-((S)-3-methoxy-piperidin-1-yl)-3-oxo-propyl]-amide | 613.14/ 615.18 | 1.52 | Q |
| 56 | 5-Chloro-thiophene-2-carboxylic acid [(S)-2-[2-ethyl-3-(3-oxo-morpholin-4-yl)-benzenesulfonylamino]-3-((S)-2-methoxy-methyl-pyrrolidin-1-yl)-3-oxo-propyl]-amide | 613.14/ 615.16 | 1.77 | M |
| 57 | 5-Chloro-thiophene-2-carboxylic acid [(S)-2-[2-ethyl-3-(3-oxo-morpholin-4-yl)-benzenesulfonylamino]-3-((R)-2-hydroxy-methyl-pyrrolidin-1-yl)-3-oxo-propyl]-amide | 599.14/ 601.15 | 1.53 | M |
| 58 | 5-Chloro-thiophene-2-carboxylic acid [(S)-2-[2-ethyl-3-(3-oxo-morpholin-4-yl)-benzenesulfonylamino]-3-((S)-2-hydroxy-methyl-pyrrolidin-1-yl)-3-oxo-propyl]-amide | 599.13/ 601.13 | 1.53 | M |
| 59 | 5-Chloro-thiophene-2-carboxylic acid [(S)-2-[2-ethyl-3-(3-oxo-morpholin-4-yl)-benzenesulfonylamino]-3-((R)-3-hydroxy-pyrrolidin-1-yl)-3-oxo-propyl]-amide | 585.13/ 587.14 | 1.4 | M |
| 60 | 5-Chloro-thiophene-2-carboxylic acid [(S)-2-[2-ethyl-3-(3-oxo-morpholin-4-yl)-benzenesulfonylamino]-3-(4-methyl-piperidin-1-yl)-3-oxo-propyl]-amide | 597.16/ 599.17 | 2 | M |
| 61 | 5-Chloro-thiophene-2-carboxylic acid [(S)-2-[2-ethyl-3-(3-oxo-morpholin-4-yl)-benzenesulfonylamino]-3-(4-ethyl-piperazin-1-yl)-3-oxo-propyl]-amide | 612.17/ 614.19 | 1.18 | M |
| 62 | 5-Chloro-thiophene-2-carboxylic acid [(S)-2-[2-ethyl-3-(3-oxo-morpholin-4-yl)-benzenesulfonylamino]-3-((R)-2-methoxy-methyl-pyrrolidin-1-yl)-3-oxo-propyl]-amide | 613.14/ 615.16 | 1.75 | M |
| 63 | 5-Chloro-thiophene-2-carboxylic acid {(S)-3-((S)-3-dimethylamino-pyrrolidin-1-yl)-2-[2-ethyl-3-(3-oxo-morpholin-4-yl)-benzene-sulfonylamino]-3-oxo-propyl}-amide; compound with trifluoro-acetic acid | 612.16/ 614.18 | 1.17 | M |
| 64 | 5-Chloro-thiophene-2-carboxylic acid [(S)-2-[2-ethyl-3-(3-oxo-morpholin-4-yl)-benzenesulfonylamino]-3-(4-hydroxy-methyl-piperidin-1-yl)-3-oxo-propyl]-amide | 613.16/ 615.17 | 1.49 | M |
| 65 | 5-Chloro-thiophene-2-carboxylic acid [(S)-2-[2-ethyl-3-(3-oxo-morpholin-4-yl)-benzenesulfonylamino]-3-(3-hydroxy-azetidin-1-yl)-3-oxo-propyl]-amide | 571.09/ 573.10 | 1.42 | M |
| 66 | 5-Chloro-thiophene-2-carboxylic acid [(S)-2-[2-ethyl-3-(3-oxo-morpholin-4-yl)-benzenesulfonylamino]-3-(4-fluoro-piperidin-1-yl)-3-oxo-propyl]-amide | 601.13/ 603.15 | 1.82 | M |
| 67 | 5-Chloro-thiophene-2-carboxylic acid [(S)-2-[2-ethyl-3-(3-oxo-morpholin-4-yl)-benzenesulfonylamino]-3-(4-methyl-piperazin-1-yl)-3-oxo-propyl]-amide; compound with trifluoro-acetic acid | 598.15/ 600.17 | 1.17 | M |
| 68 | 5-Chloro-thiophene-2-carboxylic acid {(S)-3-((R)-3-dimethylamino-pyrrolidin-1-yl)-2-[2-ethyl-3-(3-oxo-morpholin-4-yl)-benzene-sulfonylamino]-3-oxo-propyl}- | 612.17/ 614.19 | 1.17 | M |

-continued

| Example No. | Compound Name | Mass (from LC/MS) | Rt (from LC/MS) (min) | LC/MS Method |
|---|---|---|---|---|
| | amide; compound with trifluoro-acetic acid | | | |
| 69 | 5-Chloro-thiophene-2-carboxylic acid {(S)-2-[2-ethyl-3-(3-oxo-morpholin-4-yl)-benzenesulfonylamino]-3-oxo-3-pyrrolidin-1-yl-propyl}-amide | 569.13/ 571.14 | 1.63 | M |
| 70 | 5-Chloro-thiophene-2-carboxylic acid [(S)-2-[2-ethyl-3-(3-oxo-morpholin-4-yl)-benzenesulfonylamino]-3-((S)-3-hydroxy-pyrrolidin-1-yl)-3-oxo-propyl]-amide | 585.11/ 587.13 | 1.26 | Q |
| 71 | 5-Chloro-thiophene-2-carboxylic acid [(S)-2-[2-ethyl-3-(3-oxo-morpholin-4-yl)-benzenesulfonylamino]-3-((S)-2-methyl-piperidin-1-yl)-3-oxo-propyl]-amide | 597.12/ 599.16 | 1.62 | Q |
| 72 | 5-Chloro-thiophene-2-carboxylic acid [(S)-2-[2-ethyl-3-(3-oxo-morpholin-4-yl)-benzenesulfonylamino]-3-((S)-3-fluoro-pyrrolidin-1-yl)-3-oxo-propyl]-amide | 587.09/ 589.11 | 1.43 | Q |
| 73 | 5-Chloro-thiophene-2-carboxylic acid {(S)-3-(3,3-dimethyl-piperidin-1-yl)-2-[2-ethyl-3-(3-oxo-morpholin-4-yl)-benzenesulfonyl-amino]-3-oxo-propyl}-amide | 611.13/ 613.16 | 1.72 | Q |
| 74 | 5-Chloro-thiophene-2-carboxylic acid [(S)-2-[2-ethyl-3-(3-oxo-morpholin-4-yl)-benzenesulfonylamino]-3-((R)-3-fluoro-pyrrolidin-1-yl)-3-oxo-propyl]-amide | 587.08/ 589.11 | 1.44 | Q |
| 75 | 5-Chloro-thiophene-2-carboxylic acid [(S)-2-[2-ethyl-3-(3-oxo-morpholin-4-yl)-benzenesulfonylamino]-3-((R)-3-hydroxy-methyl-morpholin-4-yl)-3-oxo-propyl]-amide | 615.13/ 617.14 | 1.36 | Q |
| 76 | 5-Chloro-thiophene-2-carboxylic acid {(S)-3-azepan-1-yl-3-oxo-2-[3-(3-oxo-morpholin-4-yl)-benzenesulfonylamino]-propyl}-amide | 569.16/ 571.20 | 1.56 | Q |
| 77 | 5-Chloro-thiophene-2-carboxylic acid [(S)-2-[2-chloro-3-(3-oxo-morpholin-4-yl)-benzenesulfonylamino]-3-(4-hydroxy-piperidin-1-yl)-3-oxo-propyl]-amide | 605.12/ 607.13 | 1.28 | Q |
| 78 | 5-Chloro-thiophene-2-carboxylic acid [(S)-2-[5-fluoro-2-methoxy-3-(3-oxo-morpholin-4-yl)-benzenesulfonylamino]-3-(4-methoxy-piperidin-1-yl)-3-oxo-propyl]-amide | 633.08/ 635.09 | 1.53 | Q |
| 79 | 5-Chloro-thiophene-2-carboxylic acid {(S)-3-(4-cyclopropyl-piperazin-1-yl)-2-[5-fluoro-2-methoxy-3-(3-oxo-morpholin-4-yl)-benzenesulfonylamino]-3-oxo-propyl}-amide | 644.18/ 646.19 | 1.26 | M |
| 80 | 5-Chloro-thiophene-2-carboxylic acid {(S)-3-(4-cyclopropyl-piperazin-1-yl)-2-[5-fluoro-2-methoxy-3-(2-oxo-piperidin-1-yl)-benzenesulfonylamino]-3-oxo-propyl}-amide | 642.13/ 644.17 | 1.25 | Q |
| 81 | 5-Chloro-thiophene-2-carboxylic acid [(S)-2-[5-fluoro-2-methoxy-3-(2-oxo-piperidin-1-yl)-benzenesulfonylamino]-3-(4-isopropyl-piperazin-1-yl)-3-oxo-propyl]-amide | 644.15/ 646.19 | 1.26 | Q |
| 82 | 5-Chloro-thiophene-2-carboxylic acid [(S)-2-[5-fluoro-2-methoxy-3-(2-oxo-piperidin-1-yl)-benzenesulfonylamino]-3-(4-isopropoxy-piperidin-1-yl)-3-oxo-propyl]-amide | 659.15/ 661.18 | 1.75 | Q |
| 83 | 5-Chloro-thiophene-2-carboxylic acid {(S)-3-(4-isopropyl-piperazin-1-yl)-3-oxo-2-[3-(2-oxo-piperidin-1-yl)-2-trifluoromethyl-benzenesulfonylamino]-propyl}-amide; compound with trifluoro-acetic acid | 664.30/ 666.31 | 1.37 | M |
| 84 | 5-Chloro-thiophene-2-carboxylic acid {(S)-3-((R)-3-hydroxy-pyrrolidin-1-yl)-3-oxo-2-[3-(2-oxo-piperidin-1-yl)-2-trifluoromethyl-benzenesulfonylamino]-propyl}-amide | 623.21/ 625.23 | 1.56 | M |

| Example No. | Compound Name | Mass (from LC/MS) | Rt (from LC/MS) (min) | LC/MS Method |
|---|---|---|---|---|
| 85 | 5-Chloro-thiophene-2-carboxylic acid [(S)-2-[2-chloro-3-(2-oxo-piperidin-1-yl)-benzenesulfonylamino]-3-((R)-3-hydroxy-pyrrolidin-1-yl)-3-oxo-propyl]-amide | 589.26/ 591.27 | 1.43 | M |
| 86 | 5-Chloro-thiophene-2-carboxylic acid [(S)-2-[2-chloro-3-(2-oxo-piperidin-1-yl)-benzenesulfonylamino]-3-(4-isopropyl-piperazin-1-yl)-3-oxo-propyl]-amide; compound with trifluoro-acetic acid | 630.31/ 632.32 | 1.3 | M |
| 87 | 5-Chloro-thiophene-2-carboxylic acid [(S)-2-[2-chloro-3-(2-oxo-piperidin-1-yl)-benzenesulfonylamino]-3-(4-cyclopropyl-piperazin-1-yl)-3-oxo-propyl]-amide; compound with trifluoro-acetic acid | 628.30/ 630.31 | 1.34 | M |
| 88 | 5-Chloro-thiophene-2-carboxylic acid [(S)-2-[2-difluoromethoxy-3-(2-oxo-piperidin-1-yl)-benzenesulfonylamino]-3-(4-isopropyl-piperazin-1-yl)-3-oxo-propyl]-amide; compound with trifluoro-acetic acid | 662.36/ 664.38 | 1.37 | M |
| 89 | 5-Chloro-thiophene-2-carboxylic acid [(S)-2-[2-difluoromethoxy-3-(2-oxo-piperidin-1-yl)-benzenesulfonylamino]-3-((S)-3-fluoro-pyrrolidin-1-yl)-3-oxo-propyl]-amide | 623.26/ 625.29 | 1.85 | M |
| 90 | ({(S)-2-[2-Chloro-3-(2-oxo-piperidin-1-yl)-benzenesulfonylamino]-3-[(5-chloro-thiophene-2-carbonyl)-amino]-propionyl}-cyclopropyl-amino)-acetic acid ethyl ester | 645.19/ 647.23 | 2.01 | U |
| 91 | ({(S)-2-[2-Chloro-3-(2-oxo-piperidin-1-yl)-benzenesulfonylamino]-3-[(5-chloro-thiophene-2-carbonyl)-amino]-propionyl}-cyclopropyl-amino)-acetic acid | 617.17/ 619.17 | 1.44 | Q |
| 92 | ({(S)-3-[(5-Chloro-thiophene-2-carbonyl)-amino]-2-[2-difluoromethoxy-3-(2-oxo-piperidin-1-yl)-benzenesulfonylamino]-propionyl}-cyclopropyl-amino)-acetic acid ethyl ester | 677.08/ 679.11 | 2.14 | M |
| 93 | ({(S)-3-[(5-Chloro-thiophene-2-carbonyl)-amino]-2-[2-difluoromethoxy-3-(2-oxo-piperidin-1-yl)-benzenesulfonylamino]-propionyl}-cyclopropyl-amino)-acetic acid | 649.17/ 651.23 | 1.53 | Q |
| 94 | 5-Chloro-thiophene-2-carboxylic acid [(S)-2-[2-difluoromethoxy-3-(2-oxo-piperidin-1-yl)-benzenesulfonylamino]-3-(4-methyl-[1,4]diazepan-1-yl)-3-oxo-propyl]-amide | 648.30/ 650.35 | 1.21 | Q |
| 95 | 5-Chloro-thiophene-2-carboxylic acid [(S)-2-[2-difluoromethoxy-3-(2-oxo-piperidin-1-yl)-benzenesulfonylamino]-3-((S)-3-dimethylamino-pyrrolidin-1-yl)-3-oxo-propyl]-amide | 648.30/ 650.35 | 1.2 | Q |
| 96 | 5-Chloro-thiophene-2-carboxylic acid {(S)-3-(4-acetyl-[1,4]diazepan-1-yl)-2-[2-difluoro-methoxy-3-(2-oxo-piperidin-1-yl)-benzene-sulfonylamino]-3-oxo-propyl}-amide | 676.30/ 678.36 | 1.42 | Q |
| 97 | 5-Chloro-thiophene-2-carboxylic acid [(S)-3-(4-cyclopropyl-piperazin-1-yl)-2-(2-methyl-3-pyridin-2-yl-benzenesulfonyl-amino)-3-oxo-propyl]-amide | 588 | 5.79 | T |
| 98 | 5-Chloro-thiophene-2-carboxylic acid {(S)-3-(4-cyclopropyl-piperazin-1-yl)-2-[2-methyl-3-(2-oxo-piperidin-1-yl)-benzene-sulfonylamino]-3-oxo-propyl}-amide | 610 | 5.48 | T |
| 99 | 5-Chloro-thiophene-2-carboxylic acid [(S)-3-(4-methyl-piperidin-1-yl)-2-(2-methyl-3-pyridin-2-yl-benzenesulfonylamino)-3-oxo-propyl]-amide | 561 | 7.82 | T |
| 100 | 5-Chloro-thiophene-2-carboxylic acid [(S)-3-(4-hydroxy-piperidin-1-yl)-2-(2-methyl-3-pyridin-2-yl-benzenesulfonylamino)-3-oxo-propyl]-amide | 563 | 6.48 | T |
| 101 | 5-Chloro-thiophene-2-carboxylic acid [(S)-3-(4-isopropyl-piperazin-1-yl)-2-(2-methyl-3-pyridin-2-yl-benzenesulfonylamino)-3-oxo-propyl]-amide | 590 | 5.52 | T |
| 102 | 5-Chloro-thiophene-2-carboxylic acid [(S)-3-(4-cyclopropyl-piperazin-1-yl)-2-(2- | 604 | 5.55 | T |

| Example No. | Compound Name | Mass (from LC/MS) | Rt (from LC/MS) (min) | LC/MS Method |
|---|---|---|---|---|
| | methoxy-3-pyridin-3-yl-benzenesulfonyl-amino)-3-oxo-propyl]-amide | | | |
| 103 | 5-Chloro-thiophene-2-carboxylic acid {(S)-3-(4-cyclopropyl-[1,4]diazepan-1-yl)-2-[2-methoxy-3-(2-oxo-piperidin-1-yl)-benzene-sulfonylamino]-3-oxo-propyl}-amide | 638 | 5.49 | T |
| 104 | 5-Chloro-thiophene-2-carboxylic acid {(S)-3-(4-isopropyl-piperazin-1-yl)-2-[2-methyl-3-(2-oxo-piperidin-1-yl)-benzenesulfonyl-amino]-3-oxo-propyl}-amide | 610 | 5.37 | T |
| 105 | 5-Chloro-thiophene-2-carboxylic acid {(S)-3-(4-cyclopropyl-piperazin-1-yl)-2-[2-methoxy-3-(2-oxo-piperidin-1-yl)-benzene-sulfonylamino]-3-oxo-propyl}-amide | 624 | 5.6 | T |
| 106 | 5-Chloro-thiophene-2-carboxylic acid {(S)-3-(4-cyclopropyl-piperazin-1-yl)-2-[2-methoxy-3-(1-methyl-2-oxo-1,2-dihydro-pyridin-3-yl)-benzenesulfonylamino]-3-oxo-propyl}-amide | 634 | 5.7 | T |
| 107 | 5-Chloro-thiophene-2-carboxylic acid [(S)-3-(4-hydroxy-piperidin-1-yl)-2-(2-methoxy-3-pyridin-3-yl-benzenesulfonylamino)-3-oxo-propyl]-amide | 579 | 6.3 | T |
| 108 | 5-Chloro-thiophene-2-carboxylic acid {(S)-3-(4-hydroxy-piperidin-1-yl)-2-[2-methyl-3-(2-oxo-piperidin-1-yl)-benzenesulfonyl-amino]-3-oxo-propyl}-amide | 583 | 6.45 | T |
| 109 | 5-Chloro-thiophene-2-carboxylic acid [(S)-2-[3-(5-chloro-1-methyl-2-oxo-1,2-dihydro-pyridin-3-yl)-2-methoxy-benzenesulfonyl-amino]-3-(4-isopropyl-piperazin-1-yl)-3-oxo-propyl]-amide | 670 | 5.8 | T |
| 110 | 5-Chloro-thiophene-2-carboxylic acid {(S)-3-(4-isopropyl-piperazin-1-yl)-2-[2-methoxy-3-(1-methyl-2-oxo-1,2-dihydro-pyridin-3-yl)-benzenesulfonylamino]-3-oxo-propyl}-amide | 636 | 5.43 | T |
| 111 | 5-Chloro-thiophene-2-carboxylic acid [(S)-2-(5-fluoro-2-methoxy-3-pyridin-2-yl-benzenesulfonylamino)-3-oxo-3-pyrrolidin-1-yl-propyl]-amide | 567 | 8.04 | T |
| 112 | 5-Chloro-thiophene-2-carboxylic acid {(S)-2-[2-methoxy-3-(2-oxo-piperidin-1-yl)-benzenesulfonylamino]-3-oxo-3-[4-(2,2,2-trifluoro-ethyl)-piperazin-1-yl]-propyl}-amide | 665 | 8.04 | T |
| 113 | 5-Chloro-thiophene-2-carboxylic acid {(S)-3-(4-acetyl-piperazin-1-yl)-2-[2-difluoro-methoxy-3-(2-oxo-piperidin-1-yl)-benzene-sulfonylamino]-3-oxo-propyl}-amide | 662.29/ 664.34 | 1.44 | Q |
| 114 | 5-Chloro-thiophene-2-carboxylic acid {(S)-3-(4-cyclopropyl-piperazin-1-yl)-2-[2-methoxy-3-(2-oxo-pyrrolidin-1-yl)-benzene-sulfonylamino]-3-oxo-propyl}-amide | 610 | 5.48 | T |
| 115 | 5-Chloro-thiophene-2-carboxylic acid {(S)-2-[2-methyl-3-(2-oxo-pyrrolidin-1-yl)-benzenesulfonylamino]-3-oxo-3-[4-(2,2,2-trifluoro-ethyl)-piperazin-1-yl]-propyl}-amide | 636 | 7.94 | T |
| 116 | 5-Chloro-thiophene-2-carboxylic acid {(S)-3-[4-(2-fluoro-ethyl)-piperazin-1-yl]-2-[2-methyl-3-(2-oxo-pyrrolidin-1-yl)-benzene-sulfonylamino]-3-oxo-propyl}-amide | 600 | 5.38 | T |
| 117 | 5-Chloro-thiophene-2-carboxylic acid {(S)-3-(4-cyclopropyl-piperazin-1-yl)-2-[2-methyl-3-(2-oxo-pyrrolidin-1-yl)-benzene-sulfonylamino]-3-oxo-propyl}-amide | 594 | 5.51 | T |
| 118 | 5-Chloro-thiophene-2-carboxylic acid {(S)-3-(4-cyclopropylmethyl-piperazin-1- | 608 | 5.47 | T |

| Example No. | Compound Name | Mass (from LC/MS) | Rt (from LC/MS) (min) | LC/MS Method |
|---|---|---|---|---|
| | yl)-2-[2-methyl-3-(2-oxo-pyrrolidin-1-yl)-benzene-sulfonylamino]-3-oxo-propyl}-amide | | | |
| 119 | 5-Chloro-thiophene-2-carboxylic acid [(S)-2-(5-fluoro-2-methoxy-3-pyridin-2-yl-benzenesulfonylamino)-3-(4-hydroxy-piperidin-1-yl)-3-oxo-propyl]-amide | 597 | 7.14 | T |
| 120 | 5-Chloro-thiophene-2-carboxylic acid [(S)-3-(4-cyclopropyl-piperazin-1-yl)-2-(5-fluoro-2-methoxy-3-pyridin-2-yl-benzenesulfonyl-amino)-3-oxo-propyl]-amide | 622 | 6.14 | T |
| 121 | 5-Chloro-thiophene-2-carboxylic acid {(S)-3-(4-hydroxy-piperidin-1-yl)-2-[2-methoxy-3-(2-oxo-pyrrolidin-1-yl)-benzenesulfonyl-amino]-3-oxo-propyl}-amide | 585 | 6.39 | T |
| 122 | 5-Chloro-thiophene-2-carboxylic acid {(S)-3-(4-hydroxy-piperidin-1-yl)-2-[2-methyl-3-(2-oxo-pyrrolidin-1-yl)-benzenesulfonyl-amino]-3-oxo-propyl}-amide | 569 | 6.39 | T |
| 123 | 5-Chloro-thiophene-2-carboxylic acid [(S)-3-(4-hydroxy-piperidin-1-yl)-2-(2-methyl-3-pyridin-3-yl-benzenesulfonylamino)-3-oxo-propyl]-amide | 563 | 6.06 | T |
| 124 | 5-Chloro-thiophene-2-carboxylic acid {(S)-3-(4-cyclopropyl-piperazin-1-yl)-3-oxo-2-[3-oxo-morpholin-4-yl)-benzenesulfonyl-amino]-propyl}-amide | 596.26/ 598.30 | 1.14 | Q |
| 125 | 5-Chloro-thiophene-2-carboxylic acid [(S)-2-[2-chloro-3-(3-oxo-morpholin-4-yl)-benzenesulfonylamino]-3-(4-cyclopropyl-piperazin-1-yl)-3-oxo-propyl]-amide | 630.23 | 1.22 | Q |
| 126 | ((R)-1-{(S)-3-[(5-Chloro-thiophene-2-carbonyl)-amino]-2-[5-fluoro-2-methoxy-3-(2-oxo-piperidin-1-yl)-benzenesulfonyl-amino]-propionyl}-piperidin-2-yl)-acetic acid ethyl ester | 687.31/ 689.35 | 1.82 | Q |
| 127 | (S)-1-{(S)-3-[(5-Chloro-thiophene-2-carbonyl)-amino]-2-[5-fluoro-2-methoxy-3-(2-oxo-piperidin-1-yl)-benzenesulfonyl-amino]-propionyl}-pyrrolidine-3-carboxylic acid ethyl ester | 659.17/ 661.31 | 1.64 | Q |
| 128 | 1-{(S)-3-[(5-Chloro-thiophene-2-carbonyl)-amino]-2-[5-fluoro-2-methoxy-3-(2-oxo-piperidin-1-yl)-benzenesulfonylamino]-propionyl}-piperidine-4-carboxylic acid ethyl ester | 673.29/ 675.33 | 1.7 | Q |
| 129 | 5-Chloro-thiophene-2-carboxylic acid [(S)-3-(4-methyl-piperazin-1-yl)-2-(2-methyl-3-pyridin-2-yl-benzenesulfonylamino)-3-oxo-propyl]-amide | 562 | 4.95 | T |
| 130 | (S)-1-{(S)-3-[(5-Chloro-thiophene-2-carbonyl)-amino]-2-[5-fluoro-2-methoxy-3-(2-oxo-piperidin-1-yl)-benzenesulfonyl-amino]-propionyl}-pyrrolidine-3-carboxylic acid | 631.13/ 633.15 | 1.58 | M |
| 131 | 5-Chloro-thiophene-2-carboxylic acid {(S)-3-(4-cyclopropyl-[1,4]diazepan-1-yl)-2-[2-methyl-3-(2-oxo-pyrrolidin-1-yl)-benzene-sulfonylamino]-3-oxo-propyl}-amide | 608 | 4.6 | T |
| 132 | 5-Chloro-thiophene-2-carboxylic acid {(S)-3-((S)-3-dimethylamino-pyrrolidin-1-yl)-2-[2-methoxy-3-(2-oxo-pyrrolidin-1-yl)-benzene-sulfonylamino]-3-oxo-propyl}-amide | 598 | 5.16 | T |
| 133 | 5-Chloro-thiophene-2-carboxylic acid {(S)-2-cyclopentylcarbamoyl-2-[5-fluoro-2-methoxy-3-(3-oxo-morpholin-4-yl)-benzenesulfonylamino]-ethyl}-amide | 603.16/ 605.21 | 1.6 | Q |
| 134 | 1-{(S)-3-[(5-Chloro-thiophene-2-carbonyl)-amino]-2-[5-fluoro-2-methoxy-3-(2-oxo-piperidin-1-yl)- | 645.12/ 647.15 | 1.64 | M |

| Example No. | Compound Name | Mass (from LC/MS) | Rt (from LC/MS) (min) | LC/MS Method |
|---|---|---|---|---|
| | benzenesulfonylamino]-propionyl}-piperidine-4-carboxylic acid | | | |
| 135 | 5-Chloro-thiophene-2-carboxylic acid [(S)-3-(4-methyl-piperazin-1-yl)-2-(2-methyl-3-pyridin-3-yl-benzenesulfonylamino)-3-oxo-propyl]-amide | 562 | 5 | T |
| 136 | 5-Chloro-thiophene-2-carboxylic acid {(S)-3-[4-(2,2-difluoro-ethyl)-piperazin-1-yl]-2-[2-methyl-3-(2-oxo-pyrrolidin-1-yl)-benzene-sulfonylamino]-3-oxo-propyl}-amide | 618 | 6.97 | T |
| 137 | 5-Chloro-thiophene-2-carboxylic acid {(S)-3-((S)-3-hydroxy-pyrrolidin-1-yl)-2-[2-methoxy-3-(2-oxo-pyrrolidin-1-yl)-benzene-sulfonylamino]-3-oxo-propyl}-amide | 571 | 6.36 | T |
| 138 | 5-Chloro-thiophene-2-carboxylic acid [(S)-2-[2-chloro-5-fluoro-3-(2-oxo-piperidin-1-yl)-benzenesulfonylamino]-3-(4-cyclopropyl-piperazin-1-yl)-3-oxo-propyl]-amide | 646.36/ 649.42 | 1.25 | Q |
| 139 | (S)-1-{(S)-3-[(5-Chloro-thiophene-2-carbonyl)-amino]-2-[5-fluoro-2-methoxy-3-(3-oxo-morpholin-4-yl)-benzenesulfonyl-amino]-propionyl}-piperidine-3-carboxylic acid ethyl ester | 675.20/ 677.24 | 1.68 | Q |
| 140 | 5-Chloro-thiophene-2-carboxylic acid [(S)-2-(2-fluoro-3-pyridin-3-yl-benzenesulfonyl-amino)-3-(4-methyl-piperazin-1-yl)-3-oxo-propyl]-amide | 566 | 5.03 | T |
| 141 | 5-Chloro-thiophene-2-carboxylic acid {(S)-3-(4-ethyl-piperazin-1-yl)-2-[2-methyl-3-(2-oxo-pyrrolidin-1-yl)-benzenesulfonylamino]-3-oxo-propyl}-amide | 582 | 5.29 | T |
| 142 | 5-Chloro-thiophene-2-carboxylic acid [(S)-2-[2-methyl-3-(2-oxo-piperidin-1-yl)-benzenesulfonylamino]-3-(4-methyl-piperazin-1-yl)-3-oxo-propyl]-amide | 582 | 5.18 | T |
| 143 | 5-Chloro-thiophene-2-carboxylic acid [(S)-2-(5-fluoro-2-methoxy-3-pyridin-2-yl-benzenesulfonylamino)-3-(4-methyl-piperazin-1-yl)-3-oxo-propyl]-amide | 596 | 5.72 | T |
| 144 | 5-Chloro-thiophene-2-carboxylic acid [(S)-2-[2-difluoromethoxy-3-(2-oxo-piperidin-1-yl)-benzenesulfonylamino]-3-(1,3-dihydro-isoindol-2-yl)-3-oxo-propyl]-amide | 653.18/ 655.20 | 1.77 | Q |
| 145 | 5-Chloro-thiophene-2-carboxylic acid [(S)-2-[2-methyl-3-(2-oxo-pyrrolidin-1-yl)-benzenesulfonylamino]-3-oxo-3-(1,4,6,7-tetrahydro-imidazo[4,5-c]pyridin-5-yl)-propyl]-amide | 591 | 5.14 | T |
| 146 | 5-Chloro-thiophene-2-carboxylic acid [(S)-2-[2-methyl-3-(2-oxo-pyrrolidin-1-yl)-benzenesulfonylamino]-3-oxo-3-(3-oxo-piperazin-1-yl)-propyl]-amide | 568 | 6.21 | T |
| 147 | 5-Chloro-thiophene-2-carboxylic acid {(S)-3-(4-cyclopropanecarbonyl-piperazin-1-yl)-2-[2-difluoromethoxy-3-(2-oxo-piperidin-1-yl)-benzenesulfonylamino]-3-oxo-propyl}-amide | 688.23/ 690.24 | 1.55 | Q |
| 148 | 4-{(S)-3-[(5-Chloro-thiophene-2-carbonyl)-amino]-2-[2-methyl-3-(2-oxo-pyrrolidin-1-yl)-benzenesulfonylamino]-propionyl}-piperazine-1-carboxylic acid tert-butyl ester | 654 | 8.13 | T |
| 149 | 5-Chloro-thiophene-2-carboxylic acid {(S)-2-[2-methyl-3-(2-oxo-pyrrolidin-1-yl)-benzenesulfonylamino]-3-oxo-3-piperazin-1-yl-propyl}-amide | 554 | 5.16 | T |
| 150 | 5-Chloro-thiophene-2-carboxylic acid [(S)-2-[2-difluoromethoxy-3-(2-oxo-piperidin-1-yl)-benzenesulfonylamino]-3-(4-methyl-piperazin-1-yl)-3-oxo-propyl]-amide | 634.12/ 636.15 | 1.22 | Q |
| 151 | 5-Chloro-thiophene-2-carboxylic acid [(S)-2-[2-difluoromethoxy-3-(2-oxo-piperidin-1- | 648.16/ 650.16 | 1.4 | Q |

| Example No. | Compound Name | Mass (from LC/MS) | Rt (from LC/MS) (min) | LC/MS Method |
|---|---|---|---|---|
| | yl)-benzenesulfonylamino]-3-(4-methyl-3-oxo-piperazin-1-yl)-3-oxo-propyl]-amide | | | |
| 152 | 5-Chloro-thiophene-2-carboxylic acid [(S)-2-[2-methyl-3-(2-oxo-pyrrolidin-1-yl)-benzenesulfonylamino]-3-oxo-3-(1,4,6,7-tetrahydro-pyrazolo[4,3-c]pyridin-5-yl)-propyl]-amide | 591 | 6.34 | T |
| 153 | 5-Chloro-thiophene-2-carboxylic acid {(S)-3-(4-methyl-3-oxo-piperazin-1-yl)-2-[2-methyl-3-(2-oxo-pyrrolidin-1-yl)-benzene-sulfonylamino]-3-oxo-propyl}-amide | 582 | 6.43 | T |
| 154 | 5-Chloro-thiophene-2-carboxylic acid {(S)-3-(6,7-dihydro-4H-thieno[3,2-c]pyridin-5-yl)-2-[2-methyl-3-(2-oxo-pyrrolidin-1-yl)-benzenesulfonylamino]-3-oxo-propyl}-amide | 607 | 8.04 | T |
| 155 | 5-Chloro-thiophene-2-carboxylic acid [(S)-2-[2-chloro-5-fluoro-3-(2-oxo-pyrrolidin-1-yl)-benzenesulfonylamino]-3-(4-methyl-piperazin-1-yl)-3-oxo-propyl]-amide | 606.10/ 608.11 | 1.78 | V |
| 156 | 5-Chloro-thiophene-2-carboxylic acid {(S)-3-(4-dimethylamino-piperidin-1-yl)-2-[2-methyl-3-(2-oxo-pyrrolidin-1-yl)-benzene-sulfonylamino]-3-oxo-propyl}-amide | 596 | 5.23 | T |
| 157 | 5-Chloro-thiophene-2-carboxylic acid [(S)-2-[2-chloro-5-fluoro-3-(2-oxo-pyrrolidin-1-yl)-benzenesulfonylamino]-3-(5,7-dihydro-pyrrolo[3,4-b]pyridin-6-yl)-3-oxo-propyl]-amide | 626.04/ 628.04 | 2.04 | V |
| 158 | 5-Chloro-thiophene-2-carboxylic acid [(S)-2-[2-chloro-5-fluoro-3-(2-oxo-pyrrolidin-1-yl)-benzenesulfonylamino]-3-(1,3-dihydro-pyrrolo[3,4-c]pyridin-2-yl)-3-oxo-propyl]-amide | 626.06/ 628.06 | 1.8 | V |
| 159 | 5-Chloro-thiophene-2-carboxylic acid [(S)-2-[2-chloro-5-fluoro-3-(2-oxo-pyrrolidin-1-yl)-benzenesulfonylamino]-3-(2-methyl-4,6-dihydro-pyrrolo[3,4-d]thiazol-5-yl)-3-oxo-propyl]-amide | 646.19/ 648.19 | 2.22 | V |
| 160 | 5-Chloro-thiophene-2-carboxylic acid [(S)-2-[2-chloro-5-fluoro-3-(2-oxo-pyrrolidin-1-yl)-benzenesulfonylamino]-3-(1,3-dihydro-isoindol-2-yl)-3-oxo-propyl]-amide | 625.20/ 627.21 | 2.42 | V |
| 161 | 5-Chloro-thiophene-2-carboxylic acid {(S)-2-[2-chloro-5-fluoro-3-(2-oxo-pyrrolidin-1-yl)-benzenesulfonylamino]-3-oxo-3-piperazin-1-yl-propyl}-amide | 592.04/ 594.04 | 2.5 | N |
| 162 | 4-{(S)-2-[2-Chloro-5-fluoro-3-(2-oxo-pyrrolidin-1-yl)-benzenesulfonylamino]-3-[(5-chloro-thiophene-2-carbonyl)-amino]-propionyl}-piperazine-1-carboxylic acid ethyl ester | 664.11/ 666.12 | 2.25 | V |
| 163 | 5-Chloro-thiophene-2-carboxylic acid {(S)-3-(hexahydro-pyrrolo[1,2-a]pyrazin-2-yl)-2-[2-methyl-3-(2-oxo-pyrrolidin-1-yl)-benzene-sulfonylamino]-3-oxo-propyl}-amide | 594 | 5.3 | T |
| 164 | 5-Chloro-thiophene-2-carboxylic acid [(S)-3-(4-methyl-piperazin-1-yl)-3-oxo-2-(4-pyrazol-1-yl-benzenesulfonylamino)-propyl]-amide | 537 | 97.3 | T |
| 165 | 5-Chloro-thiophene-2-carboxylic acid [(S)-2-(1-methyl-1H-indole-4-sulfonylamino)-3-(4-methyl-piperazin-1-yl)-3-oxo-propyl]-amide | 524 | 5.33 | T |
| 166 | 5-Chloro-thiophene-2-carboxylic acid {(S)-3-(4-methyl-piperazin-1-yl)-2-[3-(2-methyl-thiazol-4-yl)-benzenesulfonylamino]-3-oxo-propyl}-amide | 568 | 5.67 | T |
| 167 | 5-Chloro-thiophene-2-carboxylic acid [(S)-3-(4-methyl-piperazin-1-yl)-2-(naphthalene-1-sulfonylamino)-3-oxo-propyl]-amide | 521 | 5.7 | T |

-continued

| Example No. | Compound Name | Mass (from LC/MS) | Rt (from LC/MS) (min) | LC/MS Method |
|---|---|---|---|---|
| 168 | 5-Chloro-thiophene-2-carboxylic acid [(S)-3-(4-methyl-piperazin-1-yl)-2-(naphthalene-2-sulfonylamino)-3-oxo-propyl]-amide | 521 | 5.77 | T |
| 169 | 5-Chloro-thiophene-2-carboxylic acid {(S)-3-(4-methyl-piperazin-1-yl)-3-oxo-2-[4-(2-oxo-pyrrolidin-1-yl)-benzenesulfonylamino]-propyl}-amide | 554 | 4.99 | T |
| 170 | 5-Chloro-thiophene-2-carboxylic acid [(S)-2-(3-bromo-2-methyl-benzenesulfonyl-amino)-3-(4-methyl-piperazin-1-yl)-3-oxo-propyl]-amide | 563 | 5.85 | T |
| 171 | 5-Chloro-thiophene-2-carboxylic acid {(S)-3-(2-methyl-6,7-dihydro-4H-thiazolo[5,4-c]pyridin-5-yl)-2-[2-methyl-3-(2-oxo-pyrrolidin-1-yl)-benzenesulfonylamino]-3-oxo-propyl}-amide | 622 | 6.97 | T |
| 172 | 5-Chloro-thiophene-2-carboxylic acid {(S)-2-[2-methyl-3-(2-oxo-pyrrolidin-1-yl)-benzenesulfonylamino]-3-morpholin-4-yl-3-oxo-propyl}-amide | 555 | 6.35 | T |
| 173 | 5-Chloro-thiophene-2-carboxylic acid {(S)-3-(4-acetyl-piperazin-1-yl)-2-[2-methyl-3-(2-oxo-pyrrolidin-1-yl)-benzenesulfonylamino]-3-oxo-propyl}-amide | 596 | 5.98 | T |
| 174 | 5-Chloro-thiophene-2-carboxylic acid [(S)-2-(3-chloro-5-fluoro-2-methyl-benzene-sulfonylamino)-3-(4-methyl-piperazin-1-yl)-3-oxo-propyl]-amide | 537 | 5.88 | T |
| 175 | 5-Chloro-thiophene-2-carboxylic acid {(S)-2-[2-chloro-3-(2-oxo-pyrrolidin-1-yl)-benzenesulfonylamino]-3-[4-(2-methoxy-ethyl)-piperazin-1-yl]-3-oxo-propyl}-amide | 632.18/ 634.19 | 1.74 | V |
| 176 | 5-Chloro-thiophene-2-carboxylic acid {(S)-2-[2-chloro-3-(2-oxo-pyrrolidin-1-yl)-benzenesulfonylamino]-3-[4-(2-hydroxy-ethyl)-piperazin-1-yl]-3-oxo-propyl}-amide | 618.17/ 620.18 | 1.67 | V |
| 177 | 5-Chloro-thiophene-2-carboxylic acid [(S)-2-[2-methyl-3-(2-oxo-pyrrolidin-1-yl)-benzenesulfonylamino]-3-oxo-3-(3-trifluoro-methyl-5,6-dihydro-8H-[1,2,4]triazolo[4,3-a]pyrazin-7-yl)-propyl]-amide | 660 | 7.2 | T |
| 178 | 5-Chloro-thiophene-2-carboxylic acid {(S)-3-(1,3-dihydro-isoindol-2-yl)-2-[2-methyl-3-(2-oxo-pyrrolidin-1-yl)-benzenesulfonyl-amino]-3-oxo-propyl}-amide | 587.14/ 589.18 | 2.29 | O |
| 179 | 5-Chloro-thiophene-2-carboxylic acid {(S)-3-(2,2-dimethyl-piperazin-1-yl)-2-[2-methyl-3-(2-oxo-pyrrolidin-1-yl)-benzenesulfonyl-amino]-3-oxo-propyl}-amide | 582.20/ 584.23 | 1.71 | O |
| 180 | 5-Chloro-thiophene-2-carboxylic acid {(S)-3-(3,3-dimethyl-piperazin-1-yl)-2-[2-methyl-3-(2-oxo-pyrrolidin-1-yl)-benzenesulfonyl-amino]-3-oxo-propyl}-amide | 582.19/ 584.22 | 1.73 | O |
| 181 | 5-Chloro-thiophene-2-carboxylic acid {(S)-2-[2-chloro-5-fluoro-3-(2-oxo-pyrrolidin-1-yl)-benzenesulfonylamino]-3-oxo-3-[4-(2,2,2-trifluoro-ethyl)-piperazin-1-yl]-propyl}-amide | 674.08 | 2.37 | V |
| 182 | 5-Chloro-thiophene-2-carboxylic acid [(S)-2-[2-chloro-5-fluoro-3-(2-oxo-pyrrolidin-1-yl)-benzenesulfonylamino]-3-(4-cyclo-propyl-piperazin-1-yl)-3-oxo-propyl]-amide | 632.12/ 634.14 | 1.81 | V |
| 183 | 5-Chloro-thiophene-2-carboxylic acid {(S)-2-[2-chloro-5-fluoro-3-(2-oxo-piperidin-1-yl)-benzenesulfonylamino]-3-oxo-3-[4-(2,2,2-trifluoro-ethyl)-piperazin-1-yl]-propyl}-amide | 688.06 | 2.4 | V |

| Example No. | Compound Name | Mass (from LC/MS) | Rt (from LC/MS) (min) | LC/MS Method |
|---|---|---|---|---|
| 184 | 5-Chloro-thiophene-2-carboxylic acid {(S)-3-((1R,4S)-5-methyl-2,5-diaza-bicyclo[2.2.1]hept-2-yl)-2-[2-methyl-3-(2-oxo-pyrrolidin-1-yl)-benzenesulfonylamino]-3-oxo-propyl}-amide | 580.14/ 582.18 | 1.66 | O |
| 185 | 5-Chloro-thiophene-2-carboxylic acid {(S)-3-[4-(2-hydroxy-ethyl)piperazin-1-yl]-2-[2-methyl-3-(2-oxo-pyrrolidin-1-yl)-benzene-sulfonylamino]-3-oxo-propyl}-amide | 598.12/ 600.15 | 2.28 | O |
| 186 | 5-Chloro-thiophene-2-carboxylic acid {(S)-3-[4-(2-methoxy-ethyl)-piperazin-1-yl]-2-[2-methyl-3-(2-oxo-pyrrolidin-1-yl)-benzene-sulfonylamino]-3-oxo-propyl}-amide | 612.10/ 614.15 | 2.38 | O |
| 187 | 5-Chloro-thiophene-2-carboxylic acid [(S)-2-[2-methyl-3-(2-oxo-pyrrolidin-1-yl)-benzenesulfonylamino]-3-oxo-3-(3-trifluoro-methyl-piperazin-1-yl)-propyl]-amide | 622.07/ 624.12 | 2.52 | O |
| 188 | N-{(S)-1-[5-(5-Chloro-thiophen-2-yl)-isoxazol-3-ylmethyl]-2-oxo-2-[4-(2,2,2-trifluoro-ethyl)-piperazin-1-yl]-ethyl}-2-methyl-3-(2-oxo-pyrrolidin-1-yl)-benzenesulfonamide | 659.95/ 661.98 | 3.54 | N |
| 189 | 5-Chloro-thiophene-2-carboxylic acid {(S)-3-[3-(2-hydroxy-ethyl)-4-methyl-piperazin-1-yl]-2-[2-methyl-3-(2-oxo-pyrrolidin-1-yl)-benzenesulfonylamino]-3-oxo-propyl}-amide | 612.39/ 614.39 | 1.26 | R |
| 190 | 5-Chloro-thiophene-2-carboxylic acid [(S)-2-[2-chloro-5-fluoro-3-(2-oxo-pyrrolidin-1-yl)-benzenesulfonylamino]-3-((1S,4S)-5-methyl-2,5-diaza-bicyclo[2.2.1]hept-2-yl)-3-oxo-propyl]-amide | 618.03 | 2.35 | O |
| 191 | (4-{(S)-3-[(5-Chloro-thiophene-2-carbonyl)-amino]-2-[2-methyl-3-(2-oxo-pyrrolidin-1-yl)-benzenesulfonylamino]-propionyl}-piperazin-1-yl)-acetic acid ethyl ester | 640 | 6.31 | T |
| 192 | 5-Chloro-thiophene-2-carboxylic acid {(S)-3-(4-acetyl-[1,4]diazepan-1-yl)-2-[2-methyl-3-(2-oxo-pyrrolidin-1-yl)-benzenesulfonyl-amino]-3-oxo-propyl}-amide | 610 | 6.47 | T |
| 193 | 5-Chloro-thiophene-2-carboxylic acid {(S)-3-(6-methyl-octahydro-pyrrolo[3,4-b]pyridin-1-yl)-2-[2-methyl-3-(2-oxo-pyrrolidin-1-yl)-benzenesulfonylamino]-3-oxo-propyl}-amide | 608 | 5.46 | T |
| 194 | 5-Chloro-thiophene-2-carboxylic acid [(S)-2-[2-methyl-3-(2-oxo-pyrrolidin-1-yl)-benzenesulfonylamino]-3-(4-methyl-3-trifluoromethyl-piperazin-1-yl)-3-oxo-propyl]-amide | 636.06/ 638.11 | 2.85 | O |
| 195 | 5-Chloro-thiophene-2-carboxylic acid {(S)-2-[2-methyl-3-(2-oxo-pyrrolidin-1-yl)-benzenesulfonylamino]-3-[4-(1-methyl-piperidin-4-yl)-piperazin-1-yl]-3-oxo-propyl}-amide | 651 | 4.73 | T |
| 196 | 5-Chloro-thiophene-2-carboxylic acid {(S)-3-(1-methyl-4,6-dihydro-1H-pyrrolo[3,4-c]pyrazol-5-yl)-2-[2-methyl-3-(2-oxo-pyrrolidin-1-yl)-benzenesulfonylamino]-3-oxo-propyl}-amide | 591.11/ 593.15 | 2.36 | O |
| 197 | 5-Chloro-thiophene-2-carboxylic acid {(S)-2-[2-methyl-3-(2-oxo-pyrrolidin-1-yl)-benzenesulfonylamino]-3-oxo-3-[1-(2,2,2-trifluoro-ethyl)-4,6-dihydro-1H-pyrrolo[3,4-c]pyrazol-5-yl]-propyl}-amide | 659.08/ 661.13 | 2.59 | O |
| 198 | 5-Chloro-thiophene-2-carboxylic acid {(S)-3-(4-hydroxy-4-methyl-piperidin-1-yl)-2-[2-methyl-3-(2-oxo-pyrrolidin-1-yl)- | 583.15/ 585.15 | 2.33 | O |

| Example No. | Compound Name | Mass (from LC/MS) | Rt (from LC/MS) (min) | LC/MS Method |
|---|---|---|---|---|
| | benzene-sulfonylamino]-3-oxo-propyl}-amide | | | |
| 199 | 5-Chloro-thiophene-2-carboxylic acid {(S)-2-[2-chloro-5-fluoro-3-(2-oxo-pyrrolidin-1-yl)-benzenesulfonylamino]-3-[4-(2-methoxy-ethyl)-piperazin-1-yl]-3-oxo-propyl}-amide | 650.02 | 2.43 | O |
| 200 | 5-Chloro-thiophene-2-carboxylic acid {(S)-3-(S)-hexahydro-pyrrolo[1,2-a]pyrazin-2-yl-2-[2-methyl-3-(2-oxo-pyrrolidin-1-yl)-benzenesulfonylamino]-3-oxo-propyl}-amide | 594 | 5.32 | T |
| 201 | 5-Chloro-thiophene-2-carboxylic acid [(S)-2-[2-methyl-3-(2-oxo-pyrrolidin-1-yl)-benzenesulfonylamino]-3-(octahydro-pyrido[1,2-a]pyrazin-2-yl)-3-oxo-propyl]-amide | 608 | 5.44 | T |
| 202 | 5-Chloro-thiophene-2-carboxylic acid [(S)-2-[5-fluoro-2-methyl-3-(2-oxo-pyrrolidin-1-yl)-benzenesulfonylamino]-3-(4-methyl-piperazin-1-yl)-3-oxo-propyl]-amide | 586 | 5.39 | T |
| 203 | (4-{(S)-3-[(5-Chloro-thiophene-2-carbonyl)-amino]-2-[2-methyl-3-(2-oxo-pyrrolidin-1-yl)-benzenesulfonylamino]-propionyl}-piperazin-1-yl)-acetic acid | 612 | 5.27 | T |
| 204 | 5-Chloro-thiophene-2-carboxylic acid {(S)-2-[2-chloro-3-(2-oxo-pyrrolidin-1-yl)-benzenesulfonylamino]-3-oxo-3-[4-(2,2,2-trifluoro-ethyl)-piperazin-1-yl]-propyl}-amide | 656.07/ 658.08 | 3.23 | N |
| 205 | 5-Chloro-thiophene-2-carboxylic acid {(S)-2-[2-chloro-5-fluoro-3-(2-oxo-piperidin-1-yl)-benzenesulfonylamino]-3-[4-(2-hydroxy-ethyl)-piperazin-1-yl]-3-oxo-propyl}-amide | 650.09/ 652.10 | 2.5 | N |
| 206 | 5-Chloro-thiophene-2-carboxylic acid {(S)-2-[2-chloro-5-fluoro-3-(2-oxo-piperidin-1-yl)-benzenesulfonylamino]-3-[4-(2-methoxy-ethyl)-piperazin-1-yl]-3-oxo-propyl}-amide | 664.13/ 666.13 | 2.62 | N |
| 207 | 5-Chloro-thiophene-2-carboxylic acid [(S)-2-[2-chloro-3-(2-oxo-pyrrolidin-1-yl)-benzenesulfonylamino]-3-(5,6-dihydro-8H-[1,2,4]triazolo[4,3-a]pyrazin-7-yl)-3-oxo-propyl]-amide | 612.12/ 614.10 | 3.15 | S |
| 208 | 5-Chloro-thiophene-2-carboxylic acid {(S)-3-(5,6-dihydro-8H-[1,2,4]triazolo[4,3-a]pyrazin-7-yl)-2-[2-methyl-3-(2-oxo-pyrrolidin-1-yl)-benzenesulfonylamino]-3-oxo-propyl}-amide | 592.02/ 594.05 | 2.35 | O |
| 209 | 5-Chloro-thiophene-2-carboxylic acid {(S)-2-[5-fluoro-2-methyl-3-(2-oxo-pyrrolidin-1-yl)-benzenesulfonylamino]-3-[4-(2-hydroxy-ethyl)-piperazin-1-yl]-3-oxo-propyl}-amide | 616.21/ 618.18 | 2.85 | S |
| 210 | 5-Chloro-thiophene-2-carboxylic acid {(S)-2-[2-chloro-3-(2-oxo-pyrrolidin-1-yl)-benzenesulfonylamino]-3-[4-(2-isopropoxy-ethyl)-piperazin-1-yl]-3-oxo-propyl}-amide | 660.23 | 2.55 | O |
| 211 | 5-Chloro-thiophene-2-carboxylic acid {(S)-3-((3S,7R,8aS)-7-hydroxy-3-methyl-hexa-hydro-pyrrolo[1,2-a]pyrazin-2-yl)-2-[2-methyl-3-(2-oxo-pyrrolidin-1-yl)-benzene-sulfonylamino]-3-oxo-propyl}-amide | 624 | 5.27 | T |
| 212 | 5-Chloro-thiophene-2-carboxylic acid [(S)-2-[2-methyl-3-(2-methyl-5-oxo-pyrrolidin-1-yl)-benzenesulfonylamino]-3-(4-methyl-piperazin-1-yl)-3-oxo-propyl]-amide | 582 | 5.49 | T |
| 213 | 5-Chloro-thiophene-2-carboxylic acid {(S)-3-(4-methyl-piperazin-1-yl)-3-oxo-2-[3-(2-oxo-piperidin-1-yl)-benzenesulfonylamino]-propyl}-amide | 568 | 5.38 | T |
| 214 | Acetic acid (S)-1-{3-[(S)-1-{[(5-chloro-thiophene-2-carbonyl)-amino]-methyl}-2- | 626 | 6.17 | T |

-continued

| Example No. | Compound Name | Mass (from LC/MS) | Rt (from LC/MS) (min) | LC/MS Method |
|---|---|---|---|---|
| | (4-methyl-piperazin-1-yl)-2-oxo-ethyl-sulfamoyl]-2-methyl-phenyl}-pyrrolidin-2-ylmethyl ester | | | |
| 215 | (S)-N-(5-Chloro-thiophen-3-yl)-4-(4-difluoromethylene-piperidin-1-yl)-3-(2-methyl-3-pyridin-2-yl-benzenesulfonyl-amino)-4-oxo-butyramide | 595 | 8.3 | T |
| 216 | 5-Chloro-thiophene-3-carboxylic acid [(S)-3-(4-difluoromethylene-piperidin-1-yl)-2-(2-ethyl-3-pyridin-2-yl-benzenesulfonylamino)-3-oxo-propyl]-amide | 609 | 8 | T |
| 217 | (S)-N-(5-Chloro-thiophen-2-yl)-4-(4-difluoromethylene-piperidin-1-yl)-3-(2-methyl-3-pyridin-2-yl-benzenesulfonylamino)-4-oxo-butyramide | 595 | 7.9 | T |
| 218 | 5-Chloro-thiophene-3-carboxylic acid {(S)-3-(4-difluoromethylene-piperidin-1-yl)-2-[2-ethyl-3-(2-oxo-pyrrolidin-1-yl)-benzene-sulfonylamino]-3-oxo-propyl}-amide | 615 | 8.3 | T |
| 219 | 5-Chloro-thiophene-3-carboxylic acid [(S)-2-(2-ethyl-pyridin-2-yl-benzenesulfonyl-amino)-3-morpholin-4-yl-3-oxo-propyl]-amide | 563 | 6.5 | T |
| 220 | 5-Chloro-thiophene-3-carboxylic acid [(S)-2-(2-ethyl-3-pyridin-2-yl-benzenesulfonyl-amino)-3-((S)-3-methyl-morpholin-4-yl)-3-oxo-propyl]-amide | 577 | 6.9 | Z |
| 221 | 5-Chloro-thiophene-3-carboxylic acid {(S)-3-(4-difluoromethylene-piperidin-1-yl)-2-[2-ethyl-3-((S)-2-hydroxymethyl-pyrrolidin-1-yl)-benzenesulfonylamino]-3-oxo-propyl}-amide | 631 | 8 | Z |
| 222 | 5-Chloro-thiophene-2-carboxylic acid {(S)-3-((S)-3-fluoro-pyrrolidin-1-yl)-2-[2-methoxy-3-(2-oxo-piperidin-1-yl)-benzene-sulfonylamino]-3-oxo-propyl}-amide | 587 | 14.5 | T |
| 223 | 5-Chloro-thiophene-2-carboxylic acid {(S)-2-[2-methoxy-3-(2-oxo-piperidin-1-yl)-benzenesulfonylamino]-3-oxo-3-pyrrolidin-1-yl-propyl}-amide | 569 | 7.58 | T |
| 224 | 5-Chloro-thiophene-2-carboxylic acid [(S)-2-[2-methoxy-3-(2-oxo-piperidin-1-yl)-benzenesulfonylamino]-3-(4-methyl-piperazin-1-yl)-3-oxo-propyl]-amide | 598 | 5.48 | T |
| 225 | 5-Chloro-thiophene-2-carboxylic acid [(S)-2-[2-methoxy-3-(2-oxo-piperidin-1-yl)-benzene-sulfonylamino]-3-((S)-3-methyl-morpholin-4-yl)-3-oxo-propyl]-amide | 599 | 7.55 | T |
| 226 | 5-Chloro-thiophene-2-carboxylic acid {(S)-3-((S)-3-methyl-morpholin-4-yl)-2-[2-methyl-3-(2-oxo-pyrrolidin-1-yl)-benzene-sulfonylamino]-3-oxo-propyl}-amide | 569 | 7.41 | T |
| 227 | 5-Chloro-thiophene-2-carboxylic acid [(S)-2-[2-methyl-3-(2-oxo-pyrrolidin-1-yl)-benzenesulfonyl-amino]-3-(4-methyl-piperazin-1-yl)-3-oxo-propyl]-amide | 568 | 5.38 | T |
| 228 | 5-Chloro-thiophene-2-carboxylic acid {(S)-3-((S)-3-fluoro-pyrrolidin-1-yl)-2-[2-methyl-3-(2-oxo-pyrrolidin-1-yl)-benzenesulfonyl-amino]-3-oxo-propyl}-amide | 557 | 7.44 | T |
| 229 | 5-Chloro-thiophene-2-carboxylic acid {(S)-2-[2-methyl-3-(2-oxo-pyrrolidin-1-yl)-benzenesulfonyl-amino]-3-oxo-3-pyrrolidin-1-yl-propyl}-amide | 539 | 7.47 | T |
| 230 | 5-Chloro-thiophene-2-carboxylic acid [(S)-2-(2-methoxy-3-pyridin-4-yl-benzene-sulfonylamino)-3-(4-methyl-piperazin-1-yl)-3-oxo-propyl]-amide | 578 | 4.98 | T |
| 231 | 5-Chloro-thiophene-2-carboxylic acid [(S)-2-(2-methoxy-3-pyridin-4-yl-benzene-sulfonylamino)-3-((S)-3-methyl-morpholin-4-yl)-3-oxo-propyl]-amide | 579 | 6.77 | T |

| Example No. | Compound Name | Mass (from LC/MS) | Rt (from LC/MS) (min) | LC/MS Method |
|---|---|---|---|---|
| 232 | 5-Chloro-thiophene-2-carboxylic acid [(S)-3-((S)-3-fluoro-pyrrolidin-1-yl)-2-(2-methoxy-3-pyridin-4-yl-benzenesulfonyl-amino)-3-oxo-propyl]-amide | 567 | 6.73 | T |
| 233 | 5-Chloro-thiophene-2-carboxylic acid [(S)-2-(2-methoxy-3-pyridin-4-yl-benzene-sulfonylamino)-3-oxo-3-pyrrolidin-1-yl-propyl]-amide | 549 | 6.78 | T |
| 234 | 5-Chloro-thiophene-2-carboxylic acid [(S)-3-((S)-3-fluoro-pyrrolidin-1-yl)-2-(2-methoxy-3-pyridin-3-yl-benzenesulfonyl-amino)-3-oxo-propyl]-amide | 567 | 7.2 | T |
| 235 | 5-Chloro-thiophene-2-carboxylic acid [(S)-2-(2-methoxy-3-pyridin-3-yl-benzene-sulfonylamino)-3-oxo-3-pyrrolidin-1-yl-propyl]-amide | 549 | 7.28 | T |
| 236 | 5-Chloro-thiophene-2-carboxylic acid [(S)-2-(2-methoxy-3-pyridin-3-yl-benzene-sulfonylamino)-3-(4-methyl-piperazin-1-yl)-3-oxo-propyl]-amide | 578 | 5.42 | T |
| 237 | 5-Chloro-thiophene-2-carboxylic acid [(S)-2-(2-methoxy-3-pyridin-3-yl-benzene-sulfonylamino)-3-((S)-3-methyl-morpholin-4-yl)-3-oxo-propyl]-amide | 579 | 7.26 | T |
| 238 | 5-Chloro-thiophene-2-carboxylic acid [(S)-2-(5-fluoro-2-methoxy-3-pyridin-2-yl-benzenesulfonyl-amino)-3-((S)-3-methyl-morpholin-4-yl)-3-oxo-propyl]-amide | 597 | 8.01 | T |
| 239 | 5-Chloro-thiophene-2-carboxylic acid [(S)-3-(4-isopropyl-piperazin-1-yl)-2-(2-methoxy-3-pyridin-3-yl-benzenesulfonylamino)-3-oxo-propyl]-amide | 606 | 5.39 | T |
| 240 | 5-Chloro-thiophene-2-carboxylic acid [(S)-2-[2-methoxy-3-(2-oxo-piperidin-1-yl)-benzenesulfonyl-amino]-3-(4-methyl-piperidin-1-yl)-3-oxo-propyl]-amide | 597 | 8.11 | T |
| 241 | 5-Chloro-thiophene-2-carboxylic acid {(S)-3-(4-isopropyl-piperazin-1-yl)-2-[2-methoxy-3-(2-oxo-piperidin-1-yl)-benzenesulfonyl-amino]-3-oxo-propyl}-amide | 626 | 5.53 | T |
| 242 | 5-Chloro-thiophene-2-carboxylic acid [(S)-2-[2-methoxy-3-(2-oxo-piperidin-1-yl)-benzenesulfonyl-amino]-3-(2-methyl-piperidin-1-yl)-3-oxo-propyl]-amide | 597.20 | 8.04 | T |
| 243 | 5-Chloro-thiophene-2-carboxylic acid [(S)-3-(4-isopropyl-piperazin-1-yl)-2-(2-methoxy-3-pyridin-4-yl-benzenesulfonylamino)-3-oxo-propyl]-amide | 606 | 5.09 | T |

LC/MS spectra were recorded according to the following methods:

Method A: column: YMC J'shere H80 33×2.1 mm 4 μm
  solvent: ACN+0.05% TFA:H2O+0.05% TFA (flow 1.3 mL/min)
  gradient: 5:95 (0 min) to 95:5 (2.5 min) to 95:5 (3.0 min)
  ionization: ESI+

Method D: column: YMC J'shere ODS H80 20×2.1 mm 4 μm
  solvent: ACN:H2O+0.05% TFA (flow 1 mL/min)
  gradient: 4:96 (0 min) to 95:5 (2 min) to 95:5 (2.4 min) to 96:4 (2.45 min)
  ionization: ESI+

Method E: column: YMC J' shere 33×2 mm, 4 μm
  solvent: H2O+0.05% TFA:ACN+0.05% TFA 95:5 (0 min) to 5:95 (2.5 min) to 95:5
  MS method: LCT system, 0.33 s scan time for mass 170-1300

Method F: column: YMC J'shere 33×2 mm, 4 μm
  solvent: H2O+0.05% TFA:ACN+0.05% TFA 95:5 (0 min) to 5:95 (3.7 min)
  MS method: MUX system 0.15 s scan time for mass 100-1500

Method L: column: (S,S) Whelk-01, 250×4 mm,
  solvent: Hep:EtOH:MeOH 1:1:1+0.1% NH$_4$Ac Method M: column: YMC Jsphere 33*2
  Grad AcN+0.05% TFA:H2O+0.05% TFA
  5:95 (0 min) to 95:5 (3.4 min) to 95:5 (4.4 min) (flow 1 ml/min)
  MS method: LCT system TOF MS ES+

Method N: column: YMC Jsphere 33*2
  Grad AcN+0.05% TFA:H2O+0.05% TFA
  2:98 (1 min) to 95:5 (5 min) to 95:5 (6.25 min) (flow 1 ml/min)
  MS method: LCT system TOF MS ES+ <MUX96>>:C3:C Method O: column: Waters XBridge C18 4
  Grad (AcN+0.05% TFA): H2O+0.05% TFA 5:95 (0 min) to 5:95 (0.3 min) to 95:5 (3.5 min) to 95:5 (4 min)
MS method: LCT system TOF MS ES+
Method P: column: YMC J Sphere 33×2.1
  Grad: (AcN+0.08% FA): H2O+0.1% FA
  5:95 (0 min) to 95:5 (2.5 min) to 95:5 (3 min)
Method Q: column: YMC J'Shere 33×2 4 µM
  Grad: (AcN+0.05% TFA): H2O+0.05% TFA
  5:95 (0 min) to 95:5 (2.5 min) to 95:5 (3 min)
Method R: column: YMC Pack Pro C18 RS 33×2, 1
  Grad: (AcN+0.1% FA): H2O+0.1% FA
  5:95 (0 min) to 95:5 (2.5 min) to 95:5 (3 min)
Method S: column: Col Waters XBridge 4
  Grad: H2O+0.1% FA:AcN+0.08% FA
  97:3 (0 min) to 40:60 (3.5 min) to 2:98 (4 min) to 2:98 (5 min) to 97:3 (5.2 min) to 97:3 (6.5 min)
Method T: column: Symmetry C18 (2.1×50 mm) 3.5 µm n° WAT200650
  Solvent: A=0.005% TFA+H$_2$O pH=3.05 B=CH$_3$CN+0.05% TFA (flow 0.4 mL/min) gradient: 100% A (0 min) to 90% (10 min) and 5.0 min 100% B
  Injection volume=2 µL sol. 0.5 mg/mL in MeOH
  ionization: API-ES$^+$ Pharmacological Testing:

The ability of the compounds of the formulae I or Ia to inhibit thrombin or factor Xa or other enzymes like factor VIIa, plasmin, or trypsin can be assessed by determining the concentration of the compound of the formulae I or Ia that inhibits enzyme activity by 50%, i.e. the IC50 value, which was related to the inhibition constant Ki. Purified enzymes were used in chromogenic assays. The concentration of inhibitor that causes a 50% decrease in the rate of substrate hydrolysis was determined by linear regression after plotting the relative rates of hydrolysis (compared to the uninhibited control) versus the log of the concentration of the compound of formulae I or Ia. For calculating the inhibition constant Ki, the IC50 value was corrected for competition with substrate using the formula $$Ki=IC50/\{1+(\text{substrate concentration}/Km)\}$$

wherein Km is the Michaelis-Menten constant (Chen and Prusoff, Biochem. Pharmacol. 22 (1973) 3099-3108; I. H. Segal, Enzyme Kinetics, 1975, John Wiley & Sons, New York, 100-125).

Measurement of F Xa and Thrombin Inhibition:

The claimed substances were tested for F Xa/thrombin inhibition with a chromogenic assay. Compounds were evaluated as function of their activity from 10 µM to 10 µM in assay buffer (50 mM TRIS, 100 mM NaCl, 0.1% BSA, pH 7.5) with maximal final DMSO concentration (0.1%), on 25 µL enzyme (human coagulation factor Xa: Enzyme Research Laboratories HFXa, final concentration 0.003 Ul/ml; human thrombin from CTS Strasbourg final concentration 0.125 Ul/ml). The reactives were mixed, centrifuged and incubated 10 minutes at 37° C. in a 96 well microtiter plate. The enzyme reaction was started with 50 µL substrate (F Xa: S-2765, Biogenic ref 821413 in a final concentration of 62.5 µM final; thrombin: S-2238, Biogenic ref 820324 in a final concentration of 83 µM final). The time course of the reaction was monitored at 405 nm in a microtiter plate reader (Tecan M200) for 20 minutes.

The IC50 was calculated from the mean of duplicates from a dilution series of the compound with internal software Speed 1.1.

The results for inhibition of factor Xa and thrombin are shown in Table 1.

TABLE 1

| Example | IC$_{50}$ (Thrombin) [nM] | IC$_{50}$ (FXa) [nM] |
|---|---|---|
| 1 | 28 | 1.8 |
| 2 | 250 | 9.8 |
| 3 | 55 | 1.48 |
| 4 | 61 | 2.8 |
| 5 | 49 | 9.8 |
| 6 | 5.64 | 0.88 |
| 7 | 222 | 1.02 |
| 8 | 10.4 | 0.98 |
| 9 | 10.5 | 0.52 |
| 11 | 381 | 1.74 |
| 12 | 10.5 | 0.52 |
| 13 | 19 | 1.44 |
| 14 | 31 | 1 |
| 15 | 658 | 1.32 |
| 16 | 54 | 1.3 |
| 17 | 28 | 1.81 |
| 18 | 23 | 1.1 |
| 24 | 31 | 0.58 |
| 34 | 13 | 0.48 |
| 154 | 3.48 | 1.92 |
| 183 | 40 | 0.4 |
| 202 | 27 | 1.31 |

Prothrombinase Assay

The claimed substances were tested for their ability to inhibit activated platelet derived microparticles-prothrombinase activity with a chromogenic assay. Activated platelet derived microparticles (APM) were prepared from fresh human platelet rich plasma (400000 platelets/µl) activated by A23187 (100 µM-Sigma) during 5 minutes at 37° C., aliquoted and stored at −80° C. Prothrombinase complex formation was performed in a 96 well microtiter plate with 20 µl compound diluted in assay buffer (NaCl 130 mM, HEPES 20 mM, BSA Fraction V Fatty acid free 0.1%, pH 7.4), 50 µl of APM (diluted to 40000 platelets/µl), 10 µl human coagulation factor Xa (Enzyme Research Laboratories ref: HFXa) at 50 µM final concentration and 10 µl CaCl$_2$ 5 mM. The mixture was incubated 10 min at 37° C. Thrombin generation was induced by addition of 10 µl prothrombin (Enzyme Research Laboratories HP2750AL, 100 nM final concentration), incubated 6 minutes at 37° C., stopped with EDTA (30 mM) and measured through Fragment 1+2 dosage by ELISA (Enzygnost F 1+2; Dade Behring ref OPBD 035). The measurement was performed on a microtiter plate reader (Perkin Elmer Envision). The IC50 was calculated from the mean of triplicates from a dilution series of the compound with internal software Speed 1.1.

The activity of the table 1 compounds was in the range of 1 nM to 10 µM.

Continuous monitoring of endogenous thrombin generation in human plasma

Continuous monitoring of endogenous thrombin generation in human plasma was performed by a method adapted from those described by Hemker et al. (1993) and Nieuwenhuys et al. (2000). Thrombin generation experiments were carried out in defibrinated plasma obtained by mixing an aliquot of platelet-poor plasma with ancrod (50 U/ml), letting a clot form for 10 min at 37° C., and keeping the clotted plasma at 0° C. for 10 min. The fibrin thus formed was discarded before thrombin generation determination. A chromogenic substrate [0.25 mM (100 µl)], which is converted by thrombin sufficiently slowly and yet shows reasonable specificity for thrombin] then 100 µl of recombinant tissue factor and 100 µl of Ca$_2$+ buffer (0.05 M Tris-HCl, 0.1 M NaCl, 100 mM CaCl$_2$, pH 7.35, and 0.05% ovalbumin) were added to a disposable plastic microcuvette. After this, 100 µl of buffer (0.05 M Tris-HCl, 0.1 M NaCl, pH 7.35, and 0.05% ovalbumin) containing compound. The reaction was started at zero time by adding defibrinated plasma. The reagents were pre-warmed to 37° C. and the cuvette was thermostatically controlled at that temperature during the measurement. The optical density at 405 nm was recorded at the rate of 10 measurements per minute using a spectrophotometer. From the obtained curve, endogenous thrombin potential (ETP) was calculated using the method described by Nieuwenhuys et al. (2000). The activity of the table 1 compounds was in the range of 1 nM to 10 µM.

What is claimed is:

1. A compound of the formula I,

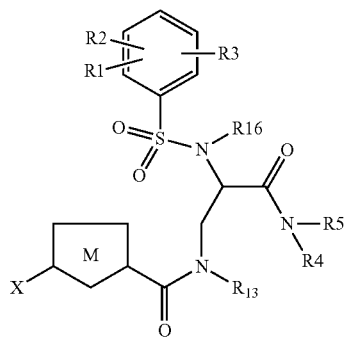

(I)

wherein

is a thiophenyl residue,

X is halogen, methyl or ethynyl,

R1, R2 and R3 are independent of one another are identical or different and are a hydrogen atom, —($C_0$-$C_3$)-alkylene-C(O)—R10, —($C_0$-$C_3$)-alkylene-C(O)—NH—R6, —($C_0$-$C_3$)-alkylene-C(O)—N(R21)-R22, —($C_0$-$C_3$)-alkylene-C(O)—O—R10, halogen, —O—($C_1$-$C_4$)-alkyl, —O—($C_1$-$C_3$)-fluoroalkyl, —($C_0$-$C_4$)-alkylene-($C_1$-$C_3$)-fluoroalkyl, —($C_1$-$C_3$)-alkylene-S(O)—R10, —($C_1$-$C_5$)-alkylene-S(O)$_2$—N(R14)-R15, —($C_1$-$C_3$)-alkylene-S(O)$_2$—R10, —($C_0$-$C_5$)-alkylene-($C_3$-$C_8$)-cycloalkyl-R23, —($C_1$-$C_4$)-alkyl, wherein alkyl is unsubstituted or substituted one, two or three times by R8, —($C_0$-$C_4$)-alkylene-aryl, wherein aryl is selected out of the group phenyl, naphthyl, biphenylyl, anthryl or fluorenyl, wherein aryl is mono-, di- or trisubstituted independently of one another by R8, or —($C_0$-$C_4$)-alkylene-heterocyclyl, wherein heterocyclyl is selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8, R4 and R5 are the same or different and are independently of one another 1) hydrogen atom, 2) —($C_1$-$C_6$)-alkyl, wherein alkyl is unsubstituted or mono-, di- or trisubstituted independently of one another by R7, 3) —($C_0$-$C_6$)-alkylene-($C_3$-$C_8$)-cycloalkyl, 4) —SO$_t$—R10, wherein t is 1 or 2, 5) —($C_0$-$C_6$)-alkylene-aryl, wherein aryl is as defined above and alkylene and aryl independently from one another are unsubstituted or mono-, di- or trisubstituted by R7, 6) —($C_1$-$C_3$)-fluoroalkyl, 7) —O—($C_1$-$C_4$)-alkyl or 8) —($C_0$-$C_6$)-alkylene-heterocyclyl, wherein heterocyclyl is as defined above and alkylene and heterocyclyl independently from one another are unsubstituted or mono-, di- or trisubstituted by R7, provided that R4 and R5 are not each a hydrogen atom, or R4 and R5 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen, wherein said heterocyclic ring is unsubstituted or mono-, di- or trisubstituted independently of one another by R7, R6 is 1) heterocyclyl, wherein heterocyclyl is as defined above and is un-substituted or mono-, di- or trisubstituted independently of one another by R8 or 2) aryl, which is as defined above wherein aryl is mono-, di- or trisubstituted independently of one another by R8, R7 is halogen, —NO$_2$, =O, —CF$_3$, —(C$_0$-C$_3$)-alkylene-C(O)—O—R10, —C(O)—R10, —CN, —OH, —NH$_2$, —C(O)—N(R10)-R20, —N(R10)-R20, =F$_2$, —O—(C$_1$-C$_3$)-fluoroalkyl, —(C$_0$-C$_4$)-alkylene-(C$_1$-C$_3$)-fluoroalkyl, —(C$_1$-C$_6$)-alkyl, wherein alkyl is unsubstituted or mono-, di- or trisubstituted independently of one another by halogen, NH$_2$, —OH or —O—(C$_1$-C$_6$)-alkyl, —(C$_0$-C$_3$)-alkylene-(C$_3$-C$_8$)-cycloalkyl, —O—(C$_1$-C$_6$)-alkyl, wherein alkyl is unsubstituted or mono-, di- or trisubstituted independently of one another by halogen, NH$_2$, —OH or a methoxy residue, or —(C$_0$-C$_3$)-alkylene-heterocyclyl, wherein heterocyclyl is as defined above and is unsubstituted mono-, di- or trisubstituted independently of one another by R10, R8 is halogen, —NO$_2$, —CN, =O, —OH, —CF$_3$, —C(O)—O—R10, —C(O)—N(R21)-R22, —N(R21)-R22, —(C$_3$-C$_8$)-cycloalkyl, —(C$_0$-C$_3$)-alkylene-O—R10, —Si—(CH$_3$)$_3$, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10, —(C$_1$-C$_8$)-alkyl, —(C$_1$-C$_8$)-alkoxy, phenyl, phenyloxy-, —(C$_1$-C$_3$)-fluoroalkyl, —O—R9, —(C$_0$-C$_4$)-alkyl-C(O)—O—C(R9, R11)-O—C(O)—R12, —NH—C(O)—NH—R10, —NH—C(O)—NH—R6, —N(R21)-C(O)—R22, —O—CF$_3$, —NH—C(O)—O—R10, or —(C$_0$-C$_4$)-alkyl-C(O)—O—C(R9, R11)-O—C(O)—O—R12, R9 and R11 are the same or different and are independently of one another hydrogen, —(C$_1$-C$_6$)-alkyl, or together with the carbon atom to which they are bonded form a 3- to 6 membered carbocyclic ring, which is unsubstituted or substituted one, two or three times by R10, R10 and R20 are the same or different and are independently of one another hydrogen atom, halogen, —(C$_1$-C$_6$)-alkyl, —(C$_0$-C$_4$)-alkyl-OH, —(C$_1$-C$_3$)-fluoroalkyl, —(C$_0$-C$_4$)-alkyl-O—(C$_1$-C$_4$)-alkyl, —(C$_0$-C$_5$)-alkyl-(C$_3$-C$_8$)-cycloalkyl, —(C$_0$-C$_2$)-alkylene-aryl, wherein aryl is as defined above and aryl is unsubstituted or substituted one, two or three times independent of each other by —(C$_1$-C$_6$)-alkyl, halogen or —(C$_3$-C$_8$)-cycloalkyl, or —(C$_0$-C$_2$)-alkylene-heterocyclyl, wherein heterocyclyl is as defined above and heterocyclyl is unsubstituted or substituted one, two or three times independent of each other by —(C$_1$-C$_6$)-alkyl, halogen or —(C$_3$-C$_8$)-cycloalkyl, R12 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R10, R13 is hydrogen atom, —OH or —O—(C$_1$-C$_4$)-alkyl, R14 and R15 are the same or different and are independently of one another hydrogen atom or —(C$_1$-C$_4$)-alkyl, R16 is hydrogen atom, —OH or —O—(C$_1$-C$_4$)-alkyl, R21 and R22 are the same or different and are independently of one another 1) hydrogen atom, 2) —(C$_1$-C$_6$)-alkyl, wherein alkyl is unsubstituted or mono-, di- or trisubstituted independently of one another by R8, 3) —(C$_0$-C$_6$)-alkylene-(C$_3$-C$_8$)-cycloalkyl, 4) —SO$_t$—R10, wherein t is 1 or 2, 5) —(C$_0$-C$_6$)-alkylene-aryl, wherein aryl is as defined above and alkylene and aryl independently from one another are unsubstituted or mono-, di- or trisubstituted by R8, 6) —(C$_1$-C$_3$)-fluoroalkyl, 7) —O—R12 or 8) —(C$_0$-C$_6$)-alkylene-heterocyclyl, wherein heterocyclyl is as defined above and alkylene and heterocyclyl independently from one another are unsubstituted or mono-, di- or trisubstituted by R8, or R21 and R22 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen, wherein said heterocyclic ring is unsubstituted or mono-, di- or trisubstituted independently of one another by R8, and R23 is hydrogen atom, —OH or —O—(C$_1$-C$_4$)-alkyl, or a stereoisomeric form thereof, or a physiologically tolerable salt of any of these.

2. A compound of the formula I as claimed in claim 1, wherein

M is a thiophenyl residue,

X is halogen, methyl or ethynyl,

R1 is —(C$_0$-C$_3$)-alkylene-C(O)—R10, —(C$_0$-C$_3$)-alkylene-C(O)—NH—R6, halogen, —(C$_0$-C$_3$)-alkylene-C(O)—O—R10, —O—(C$_1$-C$_4$)-alkyl, —O—(C$_1$-C$_3$)-fluoroalkyl, —(C$_0$-C$_4$)-alkylene-(C$_1$-C$_3$)-fluoroalkyl, —(C$_1$-C$_4$)-alkyl, wherein alkyl is unsubstituted or substituted one, two or three times by R8, —(C$_0$-C$_5$)-alkylene-(C$_3$-C$_8$)-cycloalkyl-R23, —(C$_0$-C$_4$)-alkylene-aryl, wherein aryl is selected out of the group phenyl, naphthyl, biphenylyl, anthryl or fluorenyl, wherein aryl is mono-, di- or trisubstituted independently of one another by R8, or —(C$_0$-C$_4$)-alkylene-heterocyclyl, wherein heterocyclyl is selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8, R2 and R3 are independent of one another are identical or different and are a hydrogen atom, —($C_0$-$C_3$)-alkylene-C(O)—R10, —($C_0$-$C_3$)-alkylene-C(O)—NH—R6, —($C_0$-$C_3$)-alkylene-C(O)—O—R10, —O—($C_1$-$C_4$)-alkyl, —O—($C_1$-$C_3$)-fluoroalkyl, halogen, —($C_0$-$C_4$)-alkylene-($C_1$-$C_3$)-fluoroalkyl, —($C_0$-$C_5$)-alkylene-($C_3$-$C_8$)-cycloalkyl-R23, —($C_1$-$C_4$)-alkyl, wherein alkyl is unsubstituted or substituted one, two or three times by R8, —($C_0$-$C_4$)-alkylene-aryl, wherein aryl is as defined above and is mono-, di- or trisubstituted independently of one another by R8, or —($C_0$-$C_4$)-alkylene-heterocyclyl, wherein heterocyclyl is as defined above and is unsubstituted or mono-, di- or trisubstituted independently of one another by R8, R4 and R5 are the same or different and are independently of one another 1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —$SO_t$—R10, wherein t is 1 or 2,
5) —($C_0$-$C_6$)-alkylene-aryl, wherein aryl is as defined above and alkylene and aryl independently from one another are unsubstituted or mono-, di- or trisubstituted by R7,
6) —($C_1$-$C_3$)-fluoroalkyl,
7) —O—($C_1$-$C_4$)-alkyl or
8) —($C_0$-$C_6$)-alkylene-heterocyclyl, wherein heterocyclyl is as defined above and alkylene and heterocyclyl independently from one another are unsubstituted or mono-, di- or trisubstituted by R7, provided that R4 and R5 are not each a hydrogen atom, or R4 and R5 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen, wherein said heterocyclic ring is unsubstituted or mono-, di- or trisubstituted independently of one another by R7, R6 is 1) heterocyclyl, wherein heterocyclyl is as defined above and is un-substituted or mono-, di- or trisubstituted independently of one another by R8 or
2) aryl, which is as defined above wherein aryl is mono-, di- or trisubstituted independently of one another by R8, R7 is halogen, —$NO_2$, =O, —$CF_3$, —($C_0$-$C_3$)-alkylene-C(O)—O—R10, —C(O)—R10, —CN, —OH, —$NH_2$, —C(O)—N(R10)-R20, —N(R10)-R20, =$F_2$, —O—($C_1$-$C_3$)-fluoroalkyl, —($C_0$-$C_4$)-alkylene-($C_1$-$C_3$)-fluoroalkyl, —($C_1$-$C_8$)-alkyl, wherein alkyl is unsubstituted or mono-, di- or trisubstituted independently of one another by halogen, $NH_2$, —OH or —O—($C_1$-$C_6$)-alkyl, —($C_0$-$C_3$)-alkylene-($C_3$-$C_8$)-cycloalkyl, —O—($C_1$-$C_6$)-alkyl, wherein alkyl is unsubstituted or mono-, di- or trisubstituted independently of one another by halogen, $NH_2$, —OH or a methoxy residue, or —($C_0$-$C_3$)-alkylene-heterocyclyl, wherein heterocyclyl is as defined above and is unsubstituted mono-, di- or trisubstituted independently of one another by R10, R8 is halogen, —$NO_2$, —CN, =O, —OH, —$CF_3$, —C(O)—O—R10, —($C_3$-$C_8$)-cycloalkyl, —($C_0$-$C_3$)-alkylene-O—R10, —Si—($CH_3$)$_3$, —N(R10)-S(O)$_u$—R10, wherein u is 1 or 2, —S—R10, —$SO_r$—R10, wherein r is 1 or 2, —S(O)$_v$—N(R10)-R20, wherein v is 1 or 2, —C(O)—R10, —($C_1$-$C_8$)-alkyl, —($C_1$-$C_8$)-alkoxy, phenyl, phenyloxy-, —O—R9, —($C_1$-$C_3$)-fluoroalkyl, —($C_0$-$C_4$)-alkyl-C(O)—O—C(R9, R11)-O—C(O)—R12, —NH—C(O)—NH—R10, —NH—C(O)—NH—R6, —O—$CF_3$, —NH—C(O)—O—R10, or —($C_0$-$C_4$)-alkyl-C(O)—O—C(R9, R11)-O—C(O)—O—R12, R9 and R11 are the same or different and are independently of one another hydrogen, —($C_1$-$C_6$)-alkyl, or together with the carbon atom to which they are bonded form a 3- to 6 membered carbocyclic ring, which is unsubstituted or substituted one, two or three times by R10, R10 and R20 are the same or different and are independently of one another hydrogen atom, halogen, —($C_1$-$C_6$)-alkyl, —($C_0$-$C_4$)-alkyl-OH, —($C_1$-$C_3$)-fluoroalkyl, —($C_0$-$C_4$)-alkyl-O—($C_1$-$C_4$)-alkyl, —($C_0$-$C_5$)-alkyl-($C_3$-$C_8$)-cycloalkyl, —($C_0$-$C_2$)-alkylene-aryl, wherein aryl is as defined above and aryl is unsubstituted or substituted one, two or three times independent of each other by —($C_1$-$C_6$)-alkyl, halogen or —($C_3$-$C_8$)-cycloalkyl, or —($C_0$-$C_2$)-alkylene-heterocyclyl, wherein heterocyclyl is as defined above and heterocyclyl is unsubstituted or substituted one, two or three times independent of each other by —($C_1$-$C_6$)-alkyl, halogen or —($C_3$-$C_8$)-cycloalkyl, R12 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or R10, R13 is hydrogen atom, —OH or —O—($C_1$-$C_4$)-alkyl,
R16 is hydrogen atom, —OH or —O—($C_1$-$C_4$)-alkyl, and
R23 is hydrogen atom, —OH or —O—($C_1$-$C_4$)-alkyl,
or a stereoisomeric form thereof, or a physiologically tolerable salt of any of these.

3. A compound of the formula I as claimed in claim 1, wherein

is a thiophenyl residue,

X is halogen, methyl or ethynyl,

R1 is —($C_0$-$C_3$)-alkylene-C(O)—R10, —($C_0$-$C_3$)-alkylene-C(O)—NH—R6, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl or —($C_1$-$C_4$)-alkyl, wherein alkyl is unsubstituted or substituted one, two or three times by R8, R2 is —($C_0$-$C_3$)-alkylene-C(O)—R10, —($C_0$-$C_3$)-alkylene-C(O)—NH—R6, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl or —($C_1$-$C_4$)-alkyl, wherein alkyl is unsubstituted or substituted one, two or three times by R8, —($C_0$-$C_5$)-alkylene-($C_3$-$C_8$)-cycloalkyl-R23, —($C_0$-$C_4$)-alkylene-aryl, wherein aryl is selected out of the group phenyl, naphthyl, biphenylyl, anthryl or fluorenyl, wherein aryl is mono-, di- or trisubstituted independently of one another by R8, or —($C_0$-$C_4$)-alkylene-heterocyclyl, wherein heterocyclyl is selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8, R3 is a hydrogen atom, —($C_0$-$C_3$)-alkylene-C(O)—R10, halogen, —($C_0$-$C_3$)-alkylene-C(O)—NH—R6, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl, —($C_0$-$C_5$)-alkylene-($C_3$-$C_8$)-cycloalkyl-R23, or —($C_1$-$C_4$)-alkyl, wherein alkyl is unsubstituted or substituted one, two or three times by R8, R4 and R5 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —$SO_t$—R10, wherein t is 1 or 2,
5) —($C_0$-$C_6$)-alkylene-aryl, wherein aryl is as defined above and alkylene and aryl independently from one another are unsubstituted or mono-, di- or trisubstituted by R7,
6) —($C_1$-$C_3$)-fluoroalkyl,
7) —O—($C_1$-$C_4$)-alkyl or
8) —($C_0$-$C_6$)-alkylene-heterocyclyl, wherein heterocyclyl is as defined above and alkylene and heterocyclyl independently from one another are unsubstituted or mono-, di- or trisubstituted by R7, provided that R4 and R5 are not each a hydrogen atom, or R4 and R5 together with the nitrogen atom to which they are bonded form a 4- to 10-membered mono- or bicyclic heterocyclic ring, which is selected from 2-oxa-5-azabicyclo[2.2.1]heptane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R7, R6 is 1) heterocyclyl, wherein heterocyclyl is as defined above and is un-substituted or mono-, di- or trisubstituted independently of one another by R8 or 2) aryl, which is as defined above wherein aryl is mono-, di- or trisubstituted independently of one another by R8, R7 is halogen, —NO$_2$, =O, —CF$_3$, —(C$_0$-C$_3$)-alkylene-C(O)—O—R10, —C(O)—R10, —CN, —OH, —NH$_2$, —C(O)—N(R10)-R20, —N(R10)-R20, =F$_2$, —O—(C$_1$-C$_3$)-fluoroalkyl, —(C$_0$-C$_4$)-alkylene-(C$_1$-C$_3$)-fluoroalkyl, —(C$_1$-C$_8$)-alkyl, wherein alkyl is unsubstituted or mono-, di- or trisubstituted independently of one another by halogen, NH$_2$, —OH or —O—(C$_1$-C$_6$)-alkyl, —(C$_0$-C$_3$)-alkylene-(C$_3$-C$_8$)-cycloalkyl, —O—(C$_1$-C$_6$)-alkyl, wherein alkyl is unsubstituted or mono-, di- or trisubstituted independently of one another by halogen, NH$_2$, —OH or a methoxy residue, or —(C$_0$-C$_3$)-alkylene-heterocyclyl, wherein heterocyclyl is as defined above and is unsubstituted mono-, di- or trisubstituted independently of one another by R10, R8 is halogen, —NO$_2$, —CN, =O, —OH, —CF$_3$, —C(O)—O—R10, —(C$_3$-C$_8$)-cycloalkyl, —(C$_0$-C$_3$)-alkylene-O—R10, —Si—(CH$_3$)$_3$, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10, —(C$_1$-C$_8$)-alkyl, —(C$_1$-C$_8$)-alkoxy, phenyl, phenyloxy-, —O—CF$_3$, —(C$_1$-C$_3$)-fluoroalkyl, —NH—C(O)—NH—R6 or —NH—C(O)—O—R10, R10 and R20 are the same or different and are independently of one another hydrogen atom, halogen, —(C$_1$-C$_6$)-alkyl, —(C$_0$-C$_4$)-alkyl-OH, —(C$_1$-C$_3$)-fluoroalkyl, —(C$_0$-C$_4$)-alkyl-O—(C$_1$-C$_4$)-alkyl, —(C$_0$-C$_5$)-alkyl-(C$_3$-C$_8$)-cycloalkyl, —(C$_0$-C$_2$)-alkylene-aryl, wherein aryl is as defined above and aryl is unsubstituted or substituted one, two or three times independent of each other by —(C$_1$-C$_6$)-alkyl, halogen or —(C$_3$-C$_8$)-cycloalkyl, or —(C$_0$-C$_2$)-alkylene-heterocyclyl, wherein heterocyclyl is as defined above and heterocyclyl is unsubstituted or substituted one, two or three times independent of each other by —(C$_1$-C$_6$)-alkyl, halogen or —(C$_3$-C$_8$)-cycloalkyl, R13 is hydrogen atom, —OH or —O—(C$_1$-C$_4$)-alkyl, R16 is hydrogen atom, —OH or —O—(C$_1$-C$_4$)-alkyl, and R23 is hydrogen atom, —OH or —O—(C$_1$-C$_4$)-alkyl, or a stereoisomeric form thereof, or physiologically tolerable salt of any of these.

4. A compound as claimed in claim 1 of formula Ia,

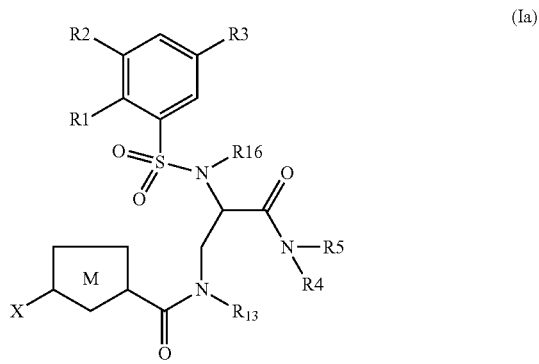

(Ia)

wherein

is a thiophenyl residue,

X is halogen, methyl or ethynyl,

R1 is —(C$_0$-C$_3$)-alkylene-C(O)—R10, —(C$_0$-C$_3$)-alkylene-C(O)—NH—R6, halogen, —(C$_0$-C$_3$)-alkylene-C(O)—O—R10, —O—(C$_1$-C$_4$)-alkyl, —O—(C$_1$-C$_3$)-fluoroalkyl, —(C$_0$-C$_4$)-alkylene-(C$_1$-C$_3$)-fluoroalkyl or —(C$_1$-C$_4$)-alkyl, wherein alkyl is unsubstituted or substituted one, two or three times by R8, R2 is —(C$_0$-C$_3$)-alkylene-C(O)—R10, —(C$_0$-C$_3$)-alkylene-C(O)—NH—R6, halogen, —(C$_0$-C$_3$)-alkylene-C(O)—O—R10, —O—(C$_1$-C$_4$)-alkyl, —O—(C$_1$-C$_3$)-fluoroalkyl, —(C$_0$-C$_4$)-alkylene-(C$_1$-C$_3$)-fluoroalkyl or —(C$_1$-C$_4$)-alkyl, wherein alkyl is unsubstituted or substituted one, two or three times by R8, —(C$_0$-C$_5$)-alkylene-(C$_3$-C$_8$)-cycloalkyl-R23, —(C$_0$-C$_4$)-alkylene-aryl, wherein aryl is selected out of the group phenyl, naphthyl, biphenylyl, anthryl or fluorenyl, wherein aryl is mono-, di- or trisubstituted independently of one another by R8, or —(C$_0$-C$_4$)-alkylene-heterocyclyl, wherein heterocyclyl is selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8, R3 is a hydrogen atom, —($C_0$-$C_3$)-alkylene-C(O)—R10, halogen, —($C_0$-$C_3$)-alkylene-C(O)—NH—R6, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl, —($C_0$-$C_5$)-alkylene-($C_3$-$C_8$)-cycloalkyl-R23, or —($C_1$-$C_4$)-alkyl, wherein alkyl is unsubstituted or substituted one, two or three times by R8, R4 and R5 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —$SO_t$—R10, wherein t is 1 or 2,
5) —($C_0$-$C_6$)-alkylene-aryl, wherein aryl is as defined above and alkylene and aryl independently from one another are unsubstituted or mono-, di- or trisubstituted by R7,
6) —($C_1$-$C_3$)-fluoroalkyl,
7) —O—($C_1$-$C_4$)-alkyl or
8) -($C_0$-$C_6$)-alkylene-heterocyclyl, wherein heterocyclyl is as defined above and alkylene and heterocyclyl independently from one another are unsubstituted or mono-, di- or trisubstituted by R7, provided that R4 and R5 are not each a hydrogen atom, or R4 and R5 together with the nitrogen atom to which they are bonded form a 4- to 10-membered mono- or bicyclic heterocyclic ring, which is selected from 2-oxa-5-azabicyclo[2.2.1]heptane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R7, R6 is 1) heterocyclyl, wherein heterocyclyl is as defined above and is un-substituted or mono-, di- or trisubstituted independently of one another by R8 or
2) aryl, which is as defined above wherein aryl is mono-, di- or trisubstituted independently of one another by R8, R7 is halogen, —$NO_2$, =O, —$CF_3$, —($C_0$-$C_3$)-alkylene-C(O)—O—R10, —C(O)—R10, —CN, —OH, —$NH_2$, —C(O)—N(R10)-R20, —N(R10)-R20, =$F_2$, —O—($C_1$-$C_3$)-fluoroalkyl, —($C_0$-$C_4$)-alkylene-($C_1$-$C_3$)-fluoroalkyl, —($C_1$-$C_8$)-alkyl, wherein alkyl is unsubstituted or mono-, di- or trisubstituted independently of one another by halogen, $NH_2$, —OH or —O—($C_1$-$C_6$)-alkyl, —($C_0$-$C_3$)-alkylene-($C_3$-$C_8$)-cycloalkyl, —O—($C_1$-$C_6$)-alkyl, wherein alkyl is unsubstituted or mono-, di- or trisubstituted independently of one another by halogen, $NH_2$, —OH or a methoxy residue, or —($C_0$-$C_3$)-alkylene-heterocyclyl, wherein heterocyclyl is as defined above and is unsubstituted mono-, di- or trisubstituted independently of one another by R10, R8 is halogen, —$NO_2$, —CN, =O, —OH, —$CF_3$, —C(O)—O—R10, —($C_3$-$C_8$)-cycloalkyl, —($C_0$-$C_3$)-alkylene-O—R10, —Si—($CH_3$)$_3$, —N(R10)-S(O)$_u$—R10, wherein u is 1 or 2, —S—R10, —$SO_r$—R10, wherein r is 1 or 2, —S(O)$_v$—N(R10)-R20, wherein v is 1 or 2, —C(O)—R10, —($C_1$-$C_8$)-alkyl, —($C_1$-$C_8$)-alkoxy, phenyl, phenyloxy-, —O—$CF_3$, —($C_1$-$C_3$)-fluoroalkyl, —NH—C(O)—NH—R6 or —NH—C(O)—O—R10, R10 and R20 are the same or different and are independently of one another hydrogen atom, halogen, —($C_1$-$C_6$)-alkyl, —($C_0$-$C_4$)-alkyl-OH, —($C_1$-$C_3$)-fluoroalkyl, —($C_0$-$C_4$)-alkyl-O—($C_1$-$C_4$)-alkyl, —($C_0$-$C_5$)-alkyl-($C_3$-$C_8$)-cycloalkyl, —($C_0$-$C_2$)-alkylene-aryl, wherein aryl is as defined above and aryl is unsubstituted or substituted one, two or three times independent of each other by —($C_1$-$C_6$)-alkyl, halogen or —($C_3$-$C_8$)-cycloalkyl, or —($C_0$-$C_2$)-alkylene-heterocyclyl, wherein heterocyclyl is as defined above and heterocyclyl is unsubstituted or substituted one, two or three times independent of each other by —($C_1$-$C_6$)-alkyl, halogen or —($C_3$-$C_8$)-cycloalkyl, R13 is hydrogen atom, —OH or —O—($C_1$-$C_4$)-alkyl,
R16 is hydrogen atom, —OH or —O—($C_1$-$C_4$)-alkyl, and
R23 is hydrogen atom, —OH or —O—($C_1$-$C_4$)-alkyl,
or a stereoisomeric form thereof, or a physiologically tolerable salt of any of these.

5. A compound of formula Ia as claimed in claim 4, wherein

is a thiophenyl residue,
X is halogen, methyl or ethynyl,
R1 is —($C_0$-$C_3$)-alkylene-C(O)—R10, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl or —($C_1$-$C_4$)-alkyl, wherein alkyl is unsubstituted or substituted one, two or three times by R8,
R2 is —($C_0$-$C_3$)-alkylene-C(O)—R10, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl or —($C_1$-$C_4$)-alkyl, wherein alkyl is unsubstituted or substituted one, two or three times by R8, —($C_0$-$C_4$)-alkylene-aryl, wherein aryl is selected out of the group phenyl, naphthyl, biphenylyl, anthryl or fluorenyl, wherein aryl is mono-, di- or trisubstituted independently of one another by R8, or
—($C_0$-$C_4$)-alkylene-heterocyclyl, wherein heterocyclyl is selected out of the group morpholinyl, oxadiazolyl, 1,2,4-oxadiazolyl, 1,3,4-oxadiazolyl, 1,4-oxazepanyl, piperidinyl, pyrazolyl, pyridyl, pyrrolidinyl or thiazolyl, and wherein said heterocyclyl is unsubstituted or mono-, di- or trisubstituted independently of one another by R8, R3 is a hydrogen atom, —($C_0$-$C_3$)-alkylene-C(O)—R10, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl or —($C_1$-$C_4$)-alkyl, wherein alkyl is unsubstituted or substituted one, two or three times by R8, R4 and R5 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —$SO_t$—R10, wherein t is 1 or 2,
5) —($C_0$-$C_6$)-alkylene-aryl, wherein aryl is as defined above and alkylene and aryl independently from one another are unsubstituted or mono-, di- or trisubstituted by R7,
6) —($C_1$-$C_3$)-fluoroalkyl,
7) —O—($C_1$-$C_4$)-alkyl or
8) —($C_0$-$C_6$)-alkylene-heterocyclyl, wherein heterocyclyl is as defined above and alkylene and heterocyclyl independently from one another are unsubstituted or mono-, di- or trisubstituted by R7, provided that R4 and R5 are not each a hydrogen atom, or R4 and R5 together with the nitrogen atom to which they are bonded form a 4- to 10-membered mono- or bicyclic heterocyclic ring, which is selected from 2-oxa-5-azabicyclo[2.2.1]heptane, azepine, azetidine, 2,5-diaza-bicyclo[2.2.1]heptane, 1,4-diazapane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R7, R7 is halogen, —$NO_2$, =O, —$CF_3$, —($C_0$-$C_3$)-alkylene-C(O)—O—R10, —C(O)—R10, —CN, —OH, —$NH_2$, —C(O)—N(R10)-R20, —N(R10)-R20, —$F_2$, —O—($C_1$-$C_3$)-fluoroalkyl, —($C_0$-$C_4$)-alkylene-($C_1$-$C_3$)-fluoroalkyl, —($C_1$-$C_8$)-alkyl, wherein alkyl is unsubstituted or mono-, di- or trisubstituted independently of one another by halogen, $NH_2$, —OH or —O—($C_1$-$C_6$)-alkyl, —($C_0$-$C_3$)-alkylene-($C_3$-$C_8$)-cycloalkyl, —O—($C_1$-$C_6$)-alkyl, wherein alkyl is unsubstituted or mono-, di- or trisubstituted independently of one another by halogen, $NH_2$, —OH or a methoxy residue, or —($C_0$-$C_3$)-alkylene-heterocyclyl, wherein heterocyclyl is as defined above and is unsubstituted mono-, di- or trisubstituted independently of one another by R10, R8 is halogen, —$NO_2$, —CN, =O, —OH, —$CF_3$, —C(O)—O—R10, —($C_3$-$C_8$)-cycloalkyl, —($C_0$-$C_3$)-alkylene-O—R10, —Si—$(CH_3)_3$, —N(R10)-$S(O)_u$—R10, wherein u is 1 or 2, —S—R10, —$SO_r$—R10, wherein r is 1 or 2, —$S(O)_v$—N(R10)-R20, wherein v is 1 or 2, —C(O)—R10, —($C_1$-$C_8$)-alkyl, —($C_1$-$C_8$)-alkoxy, phenyl, phenyloxy-, —O—$CF_3$, —($C_1$-$C_3$)-fluoroalkyl or —NH—C(O)—O—R10, R10 and R20 are the same or different and are independently of one another hydrogen atom, halogen, —($C_1$-$C_6$)-alkyl, —($C_0$-$C_4$)-alkyl-OH, —($C_1$-$C_3$)-fluoroalkyl, —($C_0$-$C_4$)-alkyl-O—($C_1$-$C_4$)-alkyl, —($C_0$-$C_5$)-alkyl-($C_3$-$C_8$)-cycloalkyl, —($C_0$-$C_2$)-alkylene-aryl, wherein aryl is as defined above and aryl is unsubstituted or substituted one, two or three times independent of each other by —($C_1$-$C_6$)-alkyl, halogen or —($C_3$-$C_8$)-cycloalkyl, or —($C_0$-$C_2$)-alkylene-heterocyclyl, wherein heterocyclyl is as defined above and heterocyclyl is unsubstituted or substituted one, two or three times independent of each other by —($C_1$-$C_6$)-alkyl, halogen or —($C_3$-$C_8$)-cycloalkyl, R13 is hydrogen atom, —OH or —O—($C_1$-$C_4$)-alkyl,
R16 is hydrogen atom, —OH or —O—($C_1$-$C_4$)-alkyl, and
R23 is hydrogen atom, —OH or —O—($C_1$-$C_4$)-alkyl,
or a stereoisomeric form thereof, or a physiologically tolerable salt of any of these.

6. A compound of formula Ia as claimed in claim 4, wherein

[M structure]

is a thiophenyl residue,
X is halogen,
R1 is —O—($C_1$-$C_4$)-alkyl, —O—($C_1$-$C_3$)-fluoroalkyl, —($C_0$-$C_3$)-alkylene-($C_1$-$C_3$)-fluoroalkyl or —($C_1$-$C_4$)-alkyl,
R2 is halogen or —($C_0$-$C_4$)-alkylene-heterocyclyl, wherein heterocyclyl is selected out of the group morpholinyl, oxadiazolyl, 1,2,4-oxadiazolyl, 1,3,4-oxadiazolyl, 1,4-oxazepanyl, piperidinyl, pyrazolyl, pyridyl, pyrrolidinyl or thiazolyl, and wherein said heterocyclyl is unsubstituted or mono-, di- or trisubstituted independently of one another by R8,
R3 is a hydrogen atom, halogen or —($C_1$-$C_4$)-alkyl,
R4 and R5 are the same or different and are independently of one another
1) hydrogen atom,
2) —($C_1$-$C_4$)-alkyl, wherein alkyl is unsubstituted or mono-substituted by R7, or
3) —($C_0$-$C_4$)-alkylene-($C_3$-$C_6$)-cycloalkyl,
provided that R4 and R5 are not each a hydrogen atom, or
R4 and R5 together with the nitrogen atom to which they are bonded form a 4- to 10-membered mono- or bicyclic heterocyclic ring, which is selected from 2-oxa-5-aza-bicyclo[2.2.1]heptane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydropyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R7, R7 is halogen, =O, —($C_0$-$C_3$)-alkylene-C(O)—O—R10, —C(O)—R10, —OH, —$NH_2$, =$F_2$, —O—($C_1$-$C_3$)-fluoroalkyl, —($C_0$-$C_3$)-alkylene-($C_1$-$C_3$)-fluoroalkyl, —($C_1$-$C_8$)-alkyl, wherein alkyl is unsubstituted or mono-, di- or trisubstituted independently of one another by halogen, $NH_2$, —OH or —O—($C_1$-$C_6$)-alkyl, —($C_0$-$C_3$)-alkylene-($C_3$-$C_8$)-cycloalkyl, —O—($C_1$-$C_6$)-alkyl, wherein alkyl is unsubstituted or mono-, di- or trisubstituted independently of one another by halogen, $NH_2$, —OH or a methoxy residue, or —($C_0$-$C_3$)-alkylene-heterocyclyl, wherein heterocyclyl is selected from morpholinyl, oxadiazolyl, piperidinyl or pyrrolidinyl and is unsubstituted or mono-substituted by R10, R8 is halogen, =O or —($C_1$-$C_4$)-alkyl, R10 and R20 are the same or different and are independently of one another hydrogen atom, halogen, —($C_1$-$C_6$)-alkyl or —($C_0$-$C_3$)-alkyl-($C_3$-$C_6$)-cycloalkyl, and R13 and R16 are each hydrogen atom, or a stereoisomeric form thereof, or a physiologically tolerable salt of any of these.

7. A process for the preparation of a compound of formula I as claimed in claim 1, comprising linking a compound of formula VII with a compound of formula III,

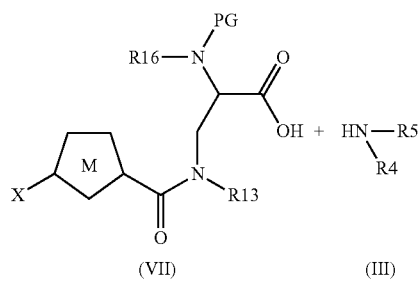

wherein X, M, R13, R16, R4 and R5 are as defined in claim 1 and PG is a protecting group, by forming an amide bond between a carboxylic acid group of formula VII and an amino group of formula III to form a compound of formula VIII,

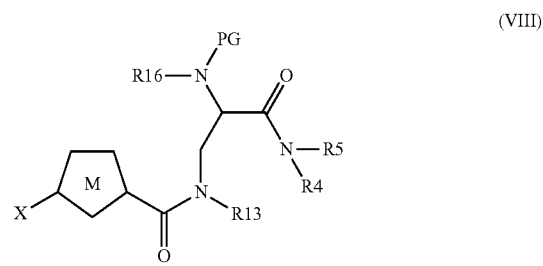

deprotecting a compound of formula VIII to form a compound of formula IX,

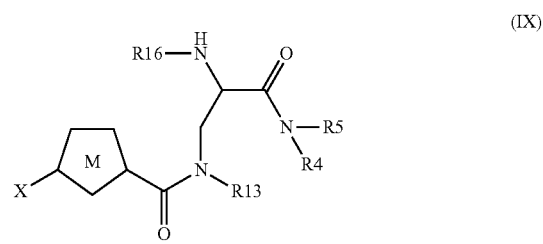

and linking a compound of the formula II with the compound of formula IX

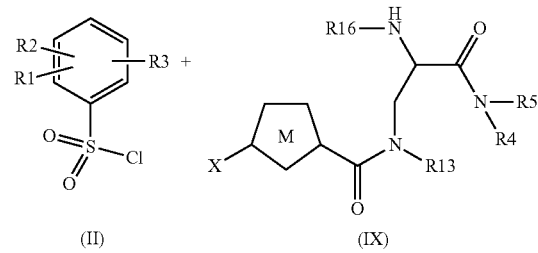

by forming a sulfonamide bond between a sulfonyl chloride group of the compound of formula II and an amino group of the compound of formula IX to form a compound of formula I.

8. A pharmaceutical composition, comprising at least one compound as claimed in claim 1 and a pharmaceutically acceptable carrier.

9. A combination preparation comprising a compound as claimed in claim 1, a pharmaceutically acceptable carrier and a marketed antiplatelet or anticoagulant agent.

* * * * *